United States Patent [19]

Hashimoto et al.

[11] Patent Number: 5,574,062
[45] Date of Patent: Nov. 12, 1996

[54] COUMARIN DERIVATIVE AND USE THEREOF

[75] Inventors: Koichi Hashimoto, Yokohama; Akio Yamada, Chigasaki; Hirokazu Hamano, Isehara; Shigehiro Mori, Zama; Hisako Moriuchi, Yokohama, all of Japan

[73] Assignee: Morinaga Milk Industry Co., Ltd., Tokyo, Japan

[21] Appl. No.: 347,467

[22] PCT Filed: Apr. 12, 1994

[86] PCT No.: PCT/JP94/00615

§ 371 Date: Dec. 13, 1994

§ 102(e) Date: Dec. 13, 1994

[87] PCT Pub. No.: WO94/24119

PCT Pub. Date: Oct. 27, 1994

[30] Foreign Application Priority Data

| Apr. 13, 1993 | [JP] | Japan | 5-108766 |
| Jun. 28, 1993 | [JP] | Japan | 5-182028 |
| Aug. 13, 1993 | [JP] | Japan | 5-222104 |
| Sep. 8, 1993 | [JP] | Japan | 5-247379 |

[51] Int. Cl.$^6$ ............ A61K 31/37; C07D 311/20
[52] U.S. Cl. ............................... 514/457; 549/289
[58] Field of Search ....................... 549/399, 401, 549/290, 289, 283, 273; 514/457

[56] References Cited

U.S. PATENT DOCUMENTS

| 2,857,401 | 10/1958 | Rorig | 549/290 |
| 3,351,482 | 11/1967 | Raue | 549/273 |
| 3,515,721 | 6/1970 | Ritter et al. | 549/289 |
| 3,585,214 | 6/1971 | Boschetti et al. | 549/290 |
| 3,644,413 | 2/1972 | Rao et al. | 549/290 |
| 3,733,338 | 5/1973 | Kimura et al. | 549/289 |
| 4,737,517 | 4/1988 | della Valle et al. | 549/289 |
| 4,918,092 | 4/1990 | Frenette et al. | 549/399 |
| 5,281,721 | 1/1994 | Powers et al. | 549/290 |
| 5,424,320 | 6/1995 | Fortin et al. | 549/290 |

FOREIGN PATENT DOCUMENTS 2317922  3/1977  France.

*Primary Examiner*—José G. Dees
*Assistant Examiner*—Deborah Lambkin
*Attorney, Agent, or Firm*—Oblon, Spivak, McClelland, Maier & Neustadt, P.C.

[57] ABSTRACT

The present invention provides compounds having 12-lipoxygenase inhibitory effect and medicines inhibiting 12-lipoxygenase selectively, and relates to novel coumarin derivatives and medicines containing the compounds as effective ingredients. Furthermore, this invention relates to compounds capable of converting to compounds inhibiting 12-lipoxygenase activities selectively according to the cleavage of modified moieties in vivo and medicines inhibiting 12-lipoxygenase selectively, and relates to novel coumarin derivatives having acyl groups as modified moieties and medicines containing the compounds as effective ingredients. The compounds of the present invention can inhibit 12-lipoxygenase strongly and selectively, and being useful as medicines for preventing and treating various circulatory diseases such as arteriosclerosis and vasospasm and for preventing of the metastasis of some kinds of cancers, and show low toxicity and few side effects.

12 Claims, No Drawings

COUMARIN DERIVATIVE AND USE THEREOF

This application is a 371 of PCT/JP94/00615 filed 12 Apr. 1994 and published as WO94/24119 Oct. 27, 1994.

TECHNICAL FIELD

The present invention relates to novel coumarin derivatives inhibiting 12-lipoxygenase selectively, and medicines containing these compounds as effective ingredients; and furthermore, the present invention relates to coumarin derivatives having a effect of inhibiting 12-lipoxygenase activities in the 12-lipoxygenase pathway selectively, and medicines containing the compounds as effective ingredients and having the effect of inhibiting 12-lipoxygenase selectively being useful as medicines for preventing and treating various circulatory diseases such as arteriosclerosis and vasospasm and for preventing the metastasis of some kinds of cancers (e.g., Lewis lung cancer).

In addition, the present invention relates to novel coumarin derivatives capable of forming substances inhibiting 12-lipoxygenase selectively through the cleavage of their modified moieties in vivo, and medicines containing these compounds as effective ingredients; and furthermore, the present invention relates to coumarin derivatives (hereinafter may be referred to as precursors) capable of converting to compounds inhibiting 12-lipoxygenase activities in the 12-lipoxygenase pathway, and medicines containing the precursors as effective ingredients and having a effect of inhibiting 12-lipoxygenase selectively being useful as medicines for preventing and treating various circulatory diseases such as arteriosclerosis and vasospasm and for preventing the metastasis of some kinds of cancers (e.g., Lewis lung cancer).

In the present specification, the indication of percentage means values by weight unless otherwise specified, and an $IC_{50}$ value means a mol concentration to produce 50% inhibition of 5-lipoxygenase or 12-lipoxygenase activities.

BACKGROUND ART

It is known that there exists a metabolic pathway called a 5-lipoxygenase pathway in the cascade of arachidonic acid and that arachidonic acid is converted to 5-hydroperoxyeicosatetraenoic acid (hereinafter may be referred to as 5-HPETE) by the function of 5-lipoxygenase ("Prostaglandin and Morbid States", edited by Seiitsu Murota, Tokyo Kagaku Dojin, 1984).

It is known that various leukotrienes can be synthesized by using this compound as an intermediate ("prostaglandin and Mobid States", edited by Seiitsu Murota, Tokyo Kagaku Dojin, 1984), and it is also known that, for example, leukotriene B4 of these leukotrienes has a strong activity of leukocyte migration and is a mediator for inflammation, and that leukotriene C4 and D4 are mediators for asthma ("Prostaglandin and Morbid States", edited by Seiitsu Murota, Tokyo Kagaku Dojin, 1984).

Hence, searches for medicines having an inhibitory effect on 5-lipoxygenase have been performed extensively from the view point that it may be anticipated to prevent and treat various diseases caused by the excess production of leukotrienes (e.g., allergic diseases, bronchial asthma, edema, various inflammatory diseases) by using medicines capable of inhibiting 5-lipoxygenase effectively, which is an incipient enzyme of a biosynthesis system of these leukotrienes.

On the other hand, there exists a metabolic pathway called a 12-lipoxygenase pathway in the cascade of arachidonic acid. 12-lipoxygenase is an enzyme present in platelets in a large amount and reacts with arachidonic acid to form 12-hydroperoxyeicosatetraenoic acid (hereinafter may be referred to as 12-HPETE), which is reduced to 12-hydroxyeicosatetraenoic acid (hereinafter may be referred to as 12-HETE).

The physiological meaning of metabolic products in the 12-lipoxygenase pathway has not been clear compared with that of the 5-lipoxygenase pathway, but recently various physiological activities of the metabolic products have become clear mainly on 12-HPETE and 12-HETE of its main metabolic products.

Physiological activities thereof may be exemplified as below. Namely, a possibility is pointed out that 12-lipoxygenase metabolic products may be concerned with arteriosclerosis by controling the function of the aggregation and adhesion of platelets and by enhancing the migration of vascular smooth muscle cells ("Gendai Iryo", Vol. 21, No. 11, pp. 3109–3113, 1989), and another possibility is also suggested that 12-HPETE may be an initiator for the occurrence of vasospasm after subarachnoid hemorrhage ("Gendai Iryo", Vol. 21, No. 11, pp. 3127–3130, 1989), and further it is shown that 12-HETE enhances the adhesion and metastasis of some kinds of cancer cells to vascular endothelial cells ("Gendai Iryo", Vol. 22, special issue, pp. 56–57, 1990). According to the above facts, it is anticipated that substances inhibiting 12-lipoxygenase may be used as medicines for preventing and treating various circulatory diseases such as arteriosclerosis and vasospasm and for preventing of the metastasis of some kinds of cancers effectively.

As a substance having a 12-lipoxygenase inhibitory effect is known baicalein, a kind of native flavonoid ("Biochemical and Biophysical Research Communications", Vol. 105, No. 3, pp. 1090–1095, 1982). In addition, a hydroxamic acid derivative (official gazette of Japanese Patent Kokai Publication No. 216961/1989, official gazette of Japanese Patent Kokai Publication No. 752/1990 and official gazette of Japanese Patent Kokai Publication No. 196767/1990) and a caffeic acid derivative (official gazette of Japanese Patent Kokai Publication No. 275552/1989 and official gazette of Japanese Patent Kokai Publication No. 235852/1990) are known.

On the other hand, coumarin derivatives are generally synthesized chemically or isolated from natural sources and purified, and as a prior art referred to a lipoxygenase inhibitory activity is known, for example, the following matter of 1):

1) Information about esculetin (6,7-dihydroxycoumarin) ("Biochimica et Biophysica Acta", Vol. 753, No. 1, pp. 130–132, 1983) is known, and it is reported that the compound showed $IC_{50}$ values of $4\times10^{-6}$M and $2.5\times10^{-6}$M to the 5-lipoxygenase and 12-lipoxygenase of mastocytoma cells respectively.

As will be described later, however, the $IC_{50}$ values shown by the compound are considerably large compared with those of the compounds of the present invention, and it is hard to say that it has a selectivity toward 12-lipoxygenase. In fact, comparative tests performed by the present inventors revealed that esculetin had considerably weaker inhibitory effect on 12-lipoxygenase than the compounds of the present invention and that esculetin showed inhibition activity also on 5-lipoxygenase to a similar extent, so that no selectivity was found.

Besides, as coumarin derivatives similar to the compounds of the present invention are known the following compounds 2)–10).

2) 6,7-dihydroxy-3-phenylcoumarin [(1) "Journal of the Chemical Society. C. Organic Chemistry", Vol. 16, pp. 2069–2070, 1969, and (2) "Zhurnal Prikladnoi Spektroskopii", Vol. 8, No. 6, pp. 1063–1066, 1968].

3) 7,8-dihydroxy-3-phenylcoumarin [(1) "Current Science", Vol. 35, No. 22, pp. 557–559, 1966, (2) "Zhurnal Prikladnoi Spektroskopii", Vol. 8, No. 6, pp. 1063–1066, 1968, (3) "Proceedings of the Indian Academy of Sciences, Section A", Vol. 56, pp. 71–85, 1962, (4) "Proceedings of the Indian Academy of Sciences, Section A", Vol. 59, No. 3, pp. 185–189, 1964, and (5) "Journal of Organic Chemistry", Vol. 19, pp. 1548–1552, 1954).

4) 6,7-dihydroxy-3-(furan-2-yl)coumarin, and 7,8-dihydroxy-3-(furan-2-yl)coumarin ["Zhurnal Prikladnoi Spektroskopii", Vol. 8, No. 6, pp. 1063–1066, 1968].

5) 6,7-dihydroxy-3-(3-nitrophenyl)coumarin ("Journal of the Chemical Society. C. Organic Chemistry", Vol. 16, pp. 2069–1070, 1969).

6) 7,8-dihydroxy-4-methyl-3-(4-nitrophenyl)coumarin ("Annales de la Societe Scientifique de Bruxelles. Series 1", Vol. 84, No. 3, pp. 383–388, 1971).

7) 6,7-dihydroxy-4-methyl-3-phenylcoumarin [(1) "Farmaco, II (Pavia), Edizione Scientifica", Vol. 12, pp. 691–694, 1957, and (2) "Atti della accademia nazionale dei Lincei. Rendiconti, Classe di scienze fisiche, matematiche e naturali", Vol. 10, pp. 230–235, 1951].

8) 6,7-dihydroxy-3,4-diphenylcoumarin [(1) Pubblicazioni del centro di studio per la citogenetica vegetale del consiglio nazionale delle ricerche", Vol. 182, pp. 350–387, 1955, and (2) "Atti della accademia nazionale dei Lincei. Rendiconti, Classe di scienze fisiche, matematiche e naturali", Vol. 10, pp. 645–649, 1954].

9) 6,7-dihydroxy-3-(pyridin-3-yl)coumarin ("Journal of the Chemical Society. C. Organic Chemistry", Vol. 16, pp. 2069–2070, 1969).

10) 7,8-dihydroxy-4-phenylcoumarin (Specification of U.S. Pat. No. 2,809,201).

It has never been known, however, that these compounds have not only 12-lipoxygenase inhibitory activities but also 5-lipoxygenase inhibitory activities.

Furthermore, as those which are not coumarin derivatives but relatively similar to the compounds of the present invention and which referred to 12-lipoxygenase inhibitory activities or 5-lipoxygenase inhibitory activities are known the following compounds 11)–13) including the above-mentioned baicalein:

11) Baicalein (5,6,7-trihydroxyflavone) ("Biochemical and Biophysical Research Communications", Vol. 105, No. 3, pp. 1090–1095, 1982).

12) 4',6,7-trihydroxyisoflavan ("Prostaglandins", Vol.28, No. 6, pp. 783–804, 1984).

13) 4',7,8-trihydroxyisoflavan, and 6,7-dihydroxy-3',4'-dimethoxyisoflavan ("International Journal of Tissue Reactions", Vol. 11, No. 3, pp. 107–112, 1989).

Of the above, the compound of 12) inhibited the formation of 5-lipoxygenase metabolic products in human peripheral leukocytes at a concentration of 10 uM completely but inhibited only 25% of the formation of 12-lipoxygenase metabolic products in platelets at the same concentration; hence the compound is known to be selective toward 5-lipoxygenase ("Prostaglandins", Vol. 28, No. 6, pp. 783–804, 1984). Besides, it is reported with regard to the compound of 13) that while the 5-lipoxygenase inhibitory activity of the compound in human peritoneal macrophages is 1–2 μM based on an $IC_{50}$ value, the 12-lipoxygenase inhibitory activity of the compound is 16–20 μM based on the $IC_{50}$ value ("International Journal of Tissue Reactions", Vol. 11, No. 3, pp. 107–112, 1989).

The compounds of the present invention have a remarkably strong 12-lipoxygenase inhibitory activity, being of the order of $10^{-9}$ to $10^{-8}$M based on the $IC_{50}$ values as will be described later. On the other hand, the $IC_{50}$ values to 5-lipoxygenase are more than 10–60 times as large as those to 12-lipoxygenase, and hence they have a selective inhibitory activity against 12-lipoxygenase.

It could never been guessed from conventional information that the compounds of the present invention have such a activity.

DISCLOSURE OF INVENTION

Incidentally, 12-lipoxygenase is an enzyme having a relationship to 5-lipoxygenase, and a substance inhibiting either of the enzymes has a possibility of inhibiting the other. In fact, some substances are known which are reported to have 5-lipoxygenase inhibitory activities and also show inhibitory activities against 12-lipoxygenase, and most of hydroxamic acid derivatives may be mentioned as examples thereof.

Regarding the selectivity of such inhibitory activities, substances inhibiting 12-lipoxygenase strongly and selectively are preferable for preventing and treating diseases seemed to be caused by mainly 12-lipoxygenase metabolic products such as the above-mentioned circulatory diseases and the metastasis of cancers, although depending upon their objectives for use.

Standing on such situations, the present inventors have noted the fact that baicalein, a kind of native flavonoid, has relatively strong 12-lipoxygenase inhibitory activity and a relatively high selectivity, and succeeded in creating compounds having strong and highly selective 12-lipoxygenase inhibitory activities by using the compound as a lead compound and performing the modification of its partial structure, which has led to the accomplishment of the present invention.

Futhermore, when a compound is utilized for medicine, for example, oral medicine, it is one of important requisites that the compound is absorbed into the body efficiently. As important factors having influence upon efficient absorption can be mentioned hydrophobicity and polarity of the compound.

The degrees of hydrophobicity or polarity of the above compounds vary broadly as may be guessed from the variety of their substituents. Hence, in case of using these compounds, for example, as oral medicine, they do not always have hydrophobicity and polarity suitable for the absorption from the intestinal tract and the like.

Hence, the present inventors have examined so-called pro-drugs regarding various modified compounds of these compounds capable of being absorbed in vivo efficiently by imparting hydrophobicity and polarity suitable for medicine to them and capable of forming primary compounds by being cleaved the modified moieties of the compounds rapidly or slowly in accordance with objects by the function of an enzyme present in vivo after absorption, and as a result have found that the monoacyl compound and the diacyl compound of a catechol-type hydroxy group possessed by these compounds in common are the compounds suited for the above object, which has led to the accomplishment of the present invention.

The object of the present invention is to provide compounds capable of inhibiting 12-lipoxygenase strongly and selectively.

Another object of the present invention is to provide novel coumarin derivatives which are absorbed in vivo efficiently and can be converted to substances inhibiting 12-lipoxygenase according to the cleavage of modified moieties in vivo, namely, the derivatives having use as so-called pro-drugs.

Further, another object of the present invention is to provide medicine inhibiting 12-lipoxygenase selectively, being useful as medicines for preventing and treating various circulatory diseases such as arteriosclerosis and vasospasm caused by 12-lipoxygenase metabolic products and for preventing the metastasis of some kinds of cancers and having a low toxicity and few side effects.

A first embodiment of the present invention dissolving the above problems is coumarin derivatives of the following general formula 9:

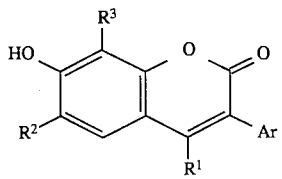

Formula 9

(wherein $R^1$ represents hydrogen or lower alkyl; $R^2$ and $R^3$ represent hydrogen or hydroxy ($R^2$ and $R^3$ being not hydrogen atoms at the same time); Ar is a group represented by the following general formula 10, 11 or 12:

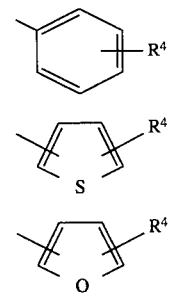

Formula 10

Formula 11

Formula 12 wherein $R^4$ represents lower alkyl, lower alkoxy, halogen, trifluoromethyl or cyano).

A second embodiment of the present invention dissolving the above problems is compounds selected from a group consisting of coumarin derivatives of the following general formula 13, or medicine containing mixtures thereof as effective components:

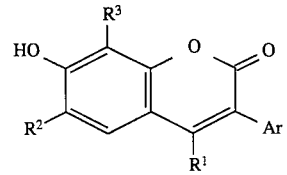

Formula 13

(wherein $R^1$ represents hydrogen or lower alkyl; $R^2$ and $R^3$ represent hydrogen or hydroxy ($R^2$ and $R^3$ being not hydrogen atoms at the same time); Ar is a group represented by the following general formula 14, 15 or 16:

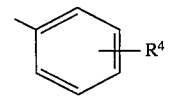

Formula 14

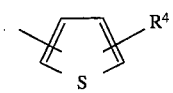

Formula 15

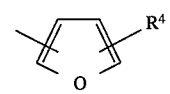

Formula 16 wherein $R^4$ represents hydrogen, lower alkyl, lower alkoxy, halogen, trifluoromethyl, cyano or nitro).

The compounds of the first embodiment of the present invention are coumarin derivatives of the following general formula 17:

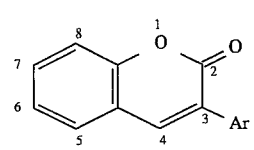

Formula 17 which are characterized by having at least two catechol-type hydroxy at the 6-, 7- and 8-positions of a coumarin ring and having an aromatic substituent at the 3-position of the coumarin ring; a method of producing them can be exemplified as below.

The compounds of the present invention of the following general formula 18:

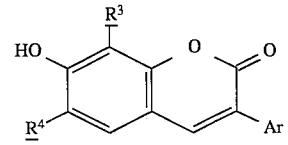

Formula 18

(wherein $\underline{R}^3$ and $\underline{R}^4$ represent hydrogen or hydroxy; Ar is a group represented by the following general formula 19, 20 or 21:

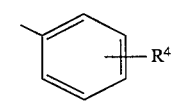

Formula 19

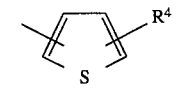

Formula 20

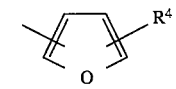

Formula 21 wherein $R^4$ represents hydrogen, lower alkyl, lower alkoxy, halogen, trifluoromethyl, cyano or nitro) can be synthesized according to the processes represented by the following chemical formulae 22 and 23:

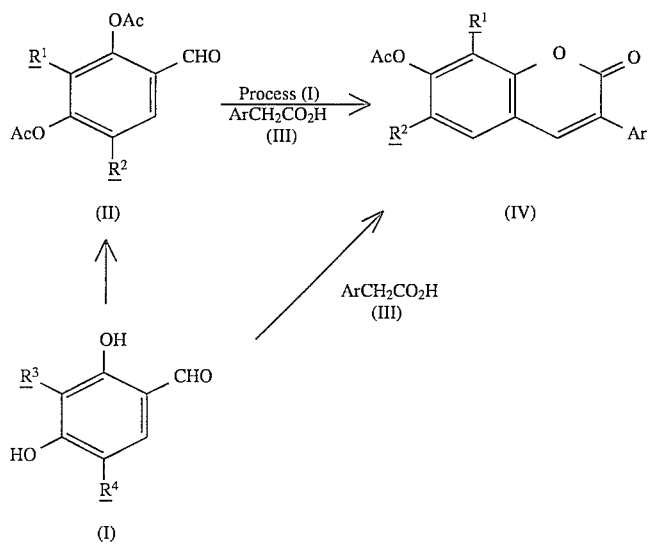

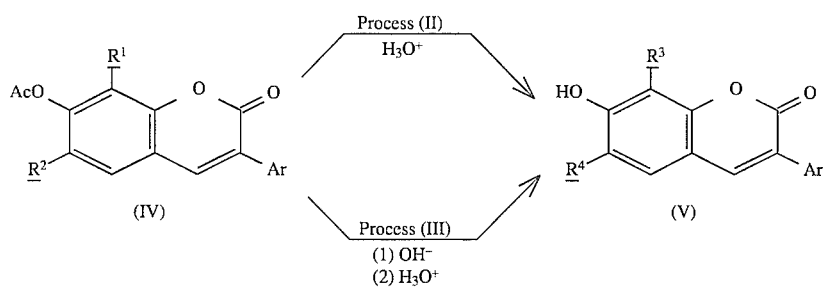

(wherein $R^1$ and $R^2$ represent hydrogen or acetoxy; and $R^3$ and $R^4$ represent hydrogen or hydroxy).

An acetylsalicylaldehyde derivative (II) and an appropriate arylacetic acid (III) are condensed under the reaction conditions known as the Perkin reaction. Namely, a compound (IV) can be obtained by refluxing them moderately in acetic anhydride in the presence of a base such as triethylamine usually at a temperature of about 120° C. for one to several hours (Process I).

An acetylsalicylaldehyde derivative (II) can be obtained by acetylating a corresponding salicylaldehyde derivative (I) using an acetylating agent such as acetic anhydride or acetyl chloride; or a compound (I) may be converted to a compound (IV) directly by acetylating a salicylaldehyde derivative (I) under ice-cooling or at room temperature in acetic anhydride in the presence of a base such as triethylamine, and transferring the formed acetylsalicylaldehyde derivative (II) to the above-mentioned Perkin reaction conditions directly. In this case, arylacetic acid (III) of the other raw material may be added at the time of the transferring to the Perkin reaction conditions or may be allowed to coexist at the stage of acetylation of a compound (I), namely, from the beginning of the reaction. Besides, alkali metal salts of the arylacetic acid may be used instead of a base such as triethylamine in the above reaction.

The obtained compound (IV) may be hydrolyzed (or ester-exchanged) under acid conditions or basic conditions and converted to the compound (V) of the present invention. First of all, in case of performing deacetylation under acid conditions, the object can be accomplished, for example, by refluxing the compound in a mixed solution of ethanol and hydrochloric acid for 30 minutes to 2 hours (Process II).

On the other hand, in case of performing deacetylation under basic conditions, the compound is reacted together with a base such as sodium hydroxide or lithium hydroxide with a mixed solution of ethanol and water as a solvent at room temperature for 1 to 3 hours.

It is thought that coumarin rings are open at this time, and the objective compound (V) may be obtained by closing the rings again according to an acid treatment by the addition of hydrochloric acid (Process III).

Besides, the compound of the present invention of the above general formula 18 may be synthesized according to the process of the reaction formulae 24 and 25:

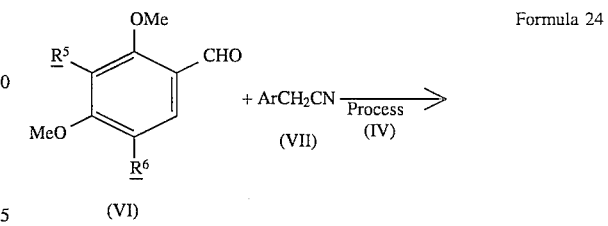

Formula 24

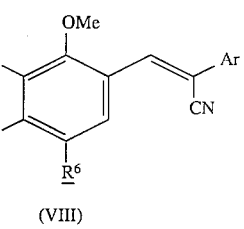

(wherein $R^5$ and $R^6$ represent hydrogen or methoxy)

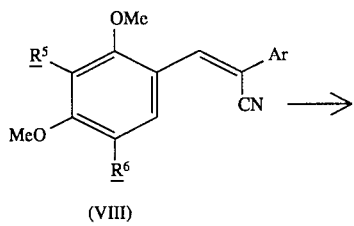

Formula 25

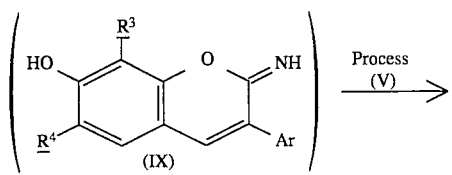

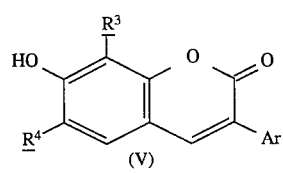

(wherein $R^5$ and $R^6$ represent hydrogen or methoxy; and $R^3$ and $R^4$ represent hydrogen or hydroxy).

Methyl ether of a salicylaldehyde derivative (VI) and an appropriate arylacetonitrile (VII) are condensed under the reaction conditions known as the Knoevenagel reaction. Namely, a compound (VIII) can be obtained by using, for example, ethanol as a solvent and heating both of them to dissolve, and stirring the solution after adding a base such as sodium hydroxide or piperidine in an amount of a catalyst (Process IV). Subsequently, the compound (V) of the present invention can be obtained by reacting the compound (VIII) with, for example, a demethylating agent such as pyridinium chloride, and treating imine (IX) thought to be formed as intermediate with an acid such as hydrochloric acid, and hydrolyzing it (Process V).

Besides, when an arylacetonitrile (VII) to be used in a condensation reaction is relatively rich in reactivity, the compound (V) of the present invention can be obtained directly through an intermediate (IX) by condensing the compound of the present invention of the above general formula 18 with a salicylaldehyde derivative (I) by the Knoevenagel reaction according to the process of the following reaction formula 26 (Process VI):

Formula 26

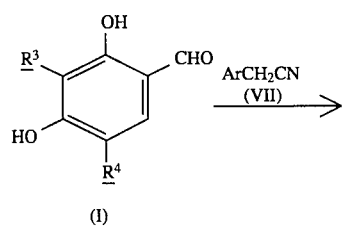

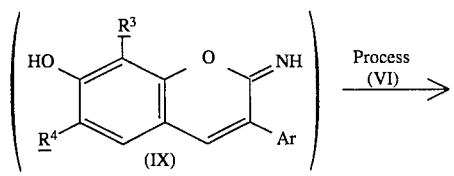

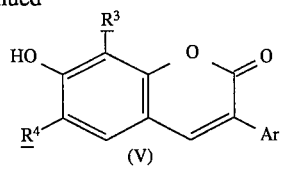

(wherein $R^3$ and $R^4$ represent hydrogen or hydroxy).

Futhermore, the compound of the following general formula 27:

Formula 27

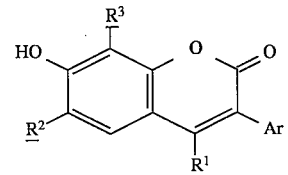

(wherein $R^1$ represents hydrogen or lower alkyl; and $R^2$ and $R^3$ represent hydrogen or hydroxy) can be synthesized according to the process of the following reaction formula 28:

Formula 28

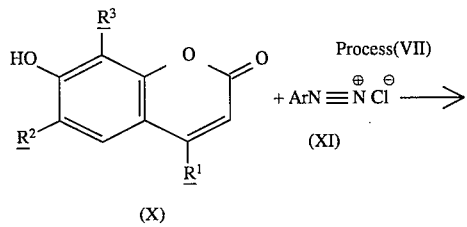

Process(VII)

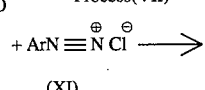

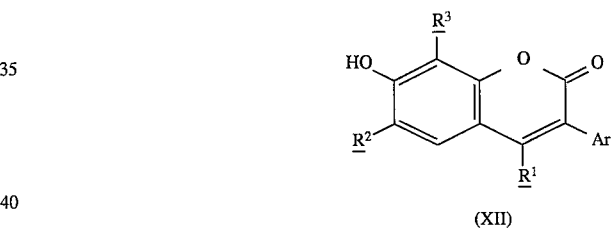

(wherein $R^1$ represents hydrogen or lower alkyl; and $R^2$ and $R^3$ represent hydrogen or hydroxy).

An aryl group is introduced to the 3-position of a coumarin derivative (X) according to the Meerwein arylation. Namely, the compound (XII) of the present invention can be obtained by reacting diazonium salt (XI) prepared from desired aromatic amine and sodium nitrite under acid conditions of hydrochloric acid with a coumarin derivative (X) in coexistence of cupric chloride.

The obtained compound of the present invention may be purified according to a known purification method such as recrystallization, chromatography and the like.

Since the above compound of the present invention has a selective inhibitory effect on 12-lipoxygenase activities, it has a function of inhibiting the formation of 12-lipoxygenase metabolic products such as 12-HPETE and 12-HETE in vivo; and the medicine of the present invention having a selective 12-lipoxygenase inhibitory effect, which contain the compound as an effective ingredient, can be utilized as medicines for treating or preventing various circulatory diseases caused by these metabolic products such as arteriosclerosis and vasospasm, further as medicines for preventing the metastasis of some kinds of cancers (e.g., Lewis lung cancer).

A third embodiment of the present invention dissolving the above problems is coumarin derivatives of the following general formula 15b:

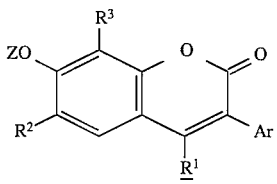

Formula 15b (wherein $R^1$ represents hydrogen or lower alkyl; $R^2$ and $R^3$ represent hydrogen or OZ ($R^2$ and $R^3$ being not hydrogen atoms at the same time); Ar is a group represented by the following general formula 16b, 17b or 18b:

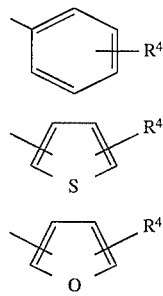

Formula 16b

Formula 17b

Formula 18b wherein $R^4$ is lower alkyl, lower alkoxy, halogen, trifluoromethyl, nitro or cyano; Z is independently hydrogen or a group represented by the following general formula 19b:

Formula 19b (all Z being not hydrogen atoms), wherein $R^5$ represents straight-chain alkyl group, branched-chain alkyl group, straight-chain alkenyl group or branched-chain alkenyl group which have carbon atoms from 1 to 20).

A fourth embodiment of the present invention dissolving the above problems is medicine containing a compound selected from a group consisting of coumarin derivatives of the following general formula 20b:

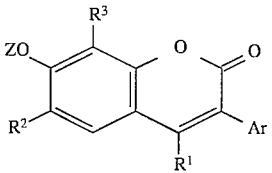

Formula 20b (wherein $R^1$ represents hydrogen or lower alkyl; $R^2$ and $R^3$ represent hydrogen or OZ ($R^2$ and $R^3$ being not hydrogen atoms at the same time); Ar is a group represented by the following general formula 21b, 22b or 23b:

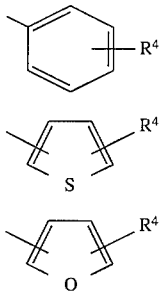

Formula 21b

Formula 22b

Formula 23b wherein $R^4$ is hydrogen, lower alkyl, lower alkoxy, halogen, trifluoromethyl, nitro or cyano; Z is independently hydrogen or a group represented by the following general formula 24b:

Formula 24b (all Z being not hydrogen atoms), wherein $R^5$ represents straight-chain alkyl group, branched-chain alkyl group, straight-chain alkenyl group or branched-chain alkenyl group which have carbon atoms from 1 to 20).

A method of producing the compound (precursor) of the third embodiment of the present invention can be exemplified as below. Namely, the compound of the present invention may be synthesized according to the process of the following reaction formula 25b:

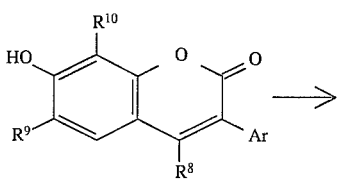

Formula 25b (a)

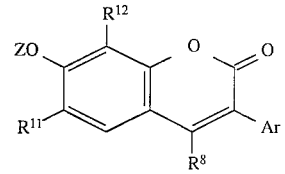

(b)

(wherein $R^8$ represents hydrogen or lower alkyl; $R^9$ and $R^{10}$ represent hydrogen or hydroxy; $R^{11}$ and $R^{12}$ represent hydrogen or OZ; Ar is a group represented by the following general formula 26b, 27b or 28b:

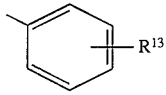

Formula 26b

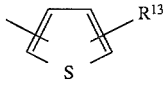

Formula 27b

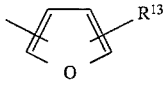

Formula 28b wherein $R^{13}$ represents hydrogen, lower alkyl, lower alkoxy, halogen, trifluoromethyl, cyano or nitro; Z is independently hydrogen or a group represented by the following general formula 29b:

Formula 29b wherein $R^{14}$ is straight-chain alkyl group, branched-chain alkyl group, straight-chain alkenyl group or branched-chain alkenyl group which have carbon atoms from 1 to 20).

Namely, the compound (b) of the present invention can be obtained by reacting a hydroxycoumarin derivative (a) with an acylating agent such as acid anhydride or acid chloride in the presence of a base of triethylamine. In this case, a compound partially acylated can be obtained by adjusting the equivalent of an acylating agent (Process A).

A hydroxycoumarin derivative (a) to be a raw material can be prepared according to the process of the following reaction formula 30b when $R^8$ is hydrogen:

When $R^8$ of hydroxycoumarin (a) to be a raw material is hydrogen or lower alkyl, it can be produced according to the process of the following reaction formula 31b:

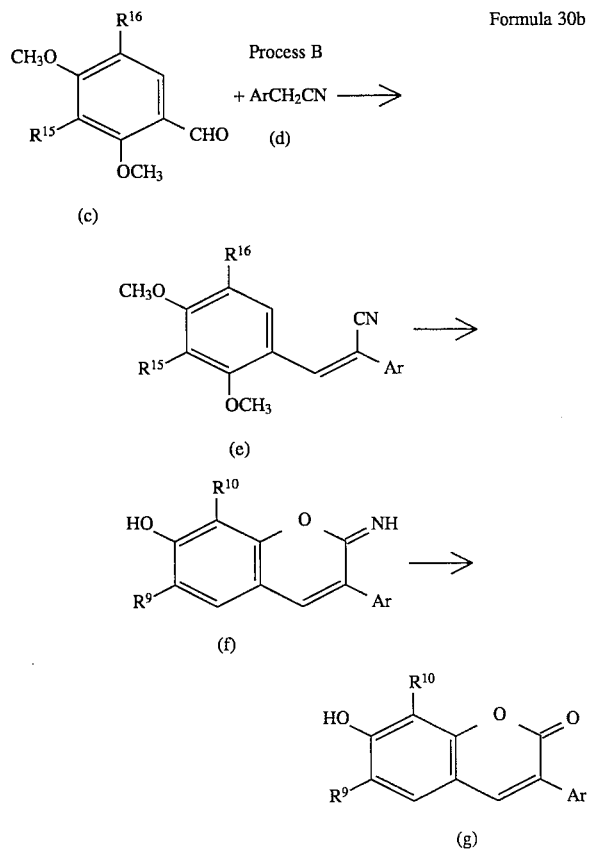

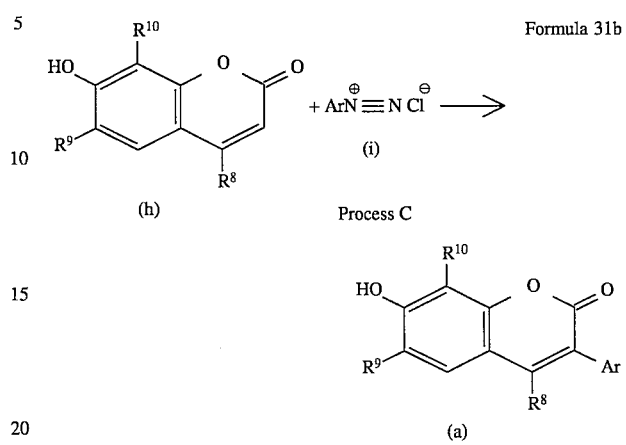

(wherein $R^{15}$ and $R^{16}$ represent hydrogen or methoxy; and $R^9$ and $R^{10}$ represent hydrogen or hydroxy.)

Namely, a hydroxycoumarin derivative (g) can be converted from a stilbene derivative (e) which is obtained by condensing methyl ether (c) of a salicylaldehyde derivative and an appropriate arylacetonitrile (d) according to the Knoevenagel condensation, demethylating it with, for example, pyridinium chloride, treating imine (f) formed as intermediate with an acid such as hydrochloric acid, and hydrolyzing it (Process B).

An aryl group is introduced to the 3-position of a coumarin derivative (h) according to the Meerwein arylation. Namely, a hydroxycoumarin derivative (a) can be obtained by reacting diazonium salt (i) prepared from desired aromatic amine and sodium nitrite under acid conditions of hydrochloric acid with a coumarin derivative (a) in coexistence of cupric chloride (Process C).

In addition, when Z is acetyl and $R^1$ is hydrogen in the general formula 1b of the objective compound of the present invention, it can be produced according to the process of the following reaction formula 32b (Process D):

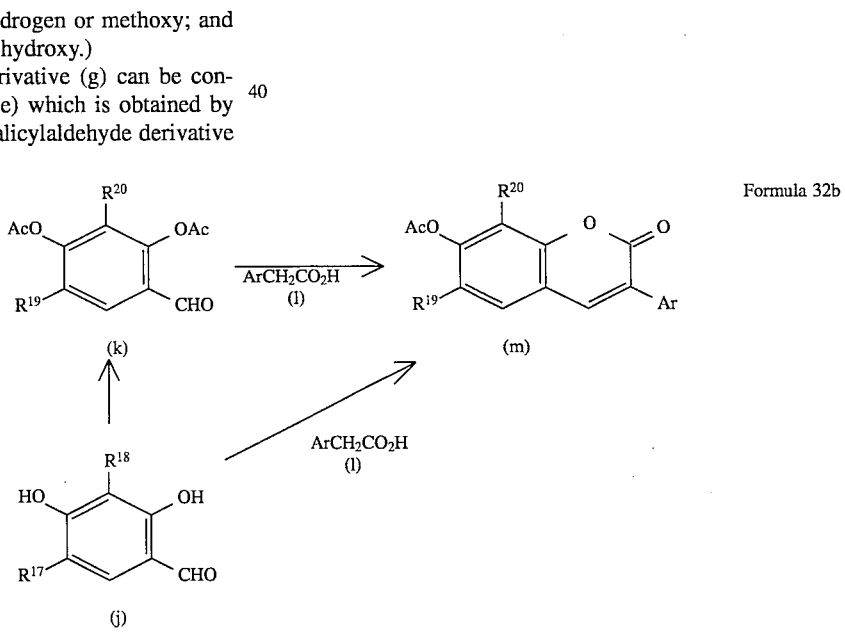

(wherein $R^{17}$ and $R^{18}$ represent hydrogen or hydroxy; and $R^{19}$ and $R^{20}$ represent hydrogen or acetoxy).

An acetylsalicylaldehyde derivative (k) and an appropriate arylacetic acid (l) are condensed under the reaction conditions known as the Perkin reaction. Namely, a compound (m) can be obtained by refluxing them moderately in acetic anhydride in the presence of a base such as triethylamine usually at a temperature of about 120° C. for one to several hours.

An acetylsalicylaldehyde derivative (k) can be obtained by acetylating a corresponding salicylaldehyde derivative (j) using an acetylating agent such as acetic anhydride or acetyl chloride; or a compound (j) may be converted to a compound (m) directly by acetylating a salicylaldehyde derivative (j) under ice-cooling or at room temperature in acetic anhydride in the presence of a base such as triethylamine, and transferring the formed acetylsalicylaldehyde derivative (k) to the above-mentioned Perkin reaction conditions directly. In this case, arylacetic acid (l) of the other raw material may be added at the time of the transferring to the Perkin reaction conditions or may be allowed to coexist at the stage of acetylation of a compound (j), namely, from the beginning of the reaction. Besides, alkali metal salts of arylacetic acid may be used instead of a base such as triethylamine in the above reaction.

The obtained compound (m) of the present invention may be deacetylated by reflux in a mixed solution of, for example, ethanol and hydrochloric acid, for 30 minutes to 4 hours according to the process of the following reaction formula 33b:

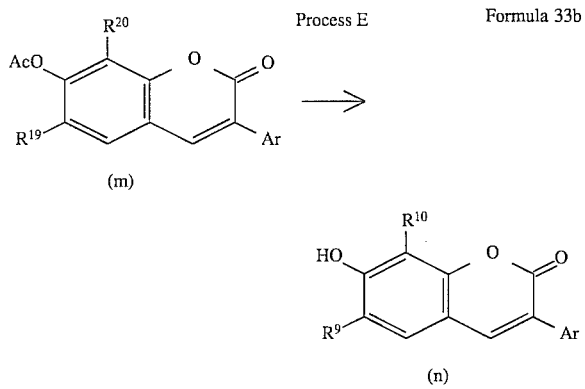

and the formed hydroxycoumarin derivative (n) may be used as a raw material in Process A (Process E).

As an acyl group as a modified moiety of the above compound of the present invention may be used those with various numbers of carbons such as monoacyl, diacyl and triacyl to prepare a compound with desired hydrophobicity and polarity. An acyl group is not particularly restricted so far as a free acid formed by the absorption and cleavage thereof in vivo may be accepted medically and pharmaceutically; however, when an acyl group is bulky, the decrease of a hydrolysis rate due to esterase or the like is observed. Hence, it is possible to control the cleavage of the above compound of the present invention in vivo by selecting an acyl group as a modified moiety.

The obtained compound of the present invention can be purified according to a known purification method such as recrystallization, chromatography and the like. The purified compound of the present invention is remarkably stable and may exist free from any change for many hours even if it comes into contact with an aqueous solution of pH 1–8.

The above compound of the present invention is absorbed in vivo and acyl groups of the compound are cleaved according to the function of an enzyme present in vivo to form a compound, which has a strong and selective 12-lipoxygenase inhibitory effect and hence has a function of inhibiting the formation of 12-lipoxygenase metabolic products such as 12-HPETE and 12-HETE and can be utilized effectively as medicines for treating or preventing various circulatory diseases caused by these metabolic products such as arteriosclerosis and vasospasm, further as medicines for preventing the metastasis of some kinds of cancers (e.g., Lewis lung cancer).

A fifth embodiment of the present invention dissolving the above problems is coumarin derivatives of the following general formula 11c:

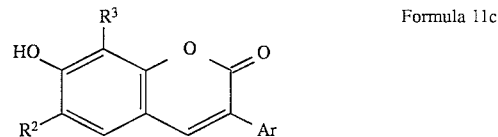

(wherein $R^2$ and $R^3$ represent hydrogen or hydroxy ($R^2$ and $R^3$ being not hydrogen atoms at the same time); and Ar is a group represented by the following general formula 12c or 13c:

wherein X represents oxygen or sulfur.)

A sixth embodiment of the present invention dissolving the above problems is medicine containing a compound selected from a group consisting of coumarin derivatives of the following general formula 14c or a mixture thereof as an effective ingredient:

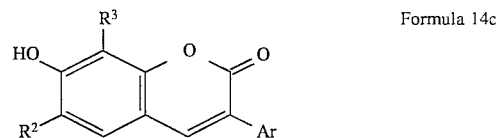

(wherein $R^2$ and $R^3$ represent hydrogen or hydroxy ($R^2$ and $R^3$ being not hydrogen atoms at the same time); and Ar is a group represented by the following general formula 15c or 16c:

wherein X represents oxygen or sulfur.)

A method of producing the compound of the fifth embodiment of the present invention can be exemplified as below. Namely, the compound of the present invention may be synthesized according to the process of the following reaction formula 17c:

Process A

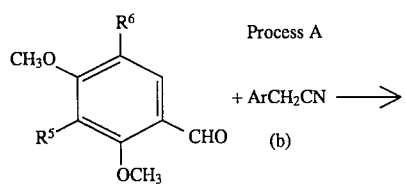

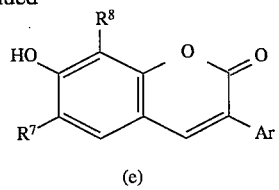

(wherein $R^5$ and $R^6$ represent hydrogen or methoxy; and $R^7$ and $R^8$ represent hydrogen or hydroxy).

Namely, the compound (e) of the present invention can be converted from an, α,β-diarylacrylonitrile derivative (c) which is obtained by condensing methyl ether (a) of a salicylaldehyde derivative and an arrpopriate arylacetonitrile (b) according to the Knoevenagel condensation, demethylating it with, for example, pyridinium chloride, treating imine (d) formed as intermediate with an acid such as hydrochloric acid, and hydrolyzing it (Process A).

In addition, it can be produced according to the process of the following reaction formulae 18c and 19c:

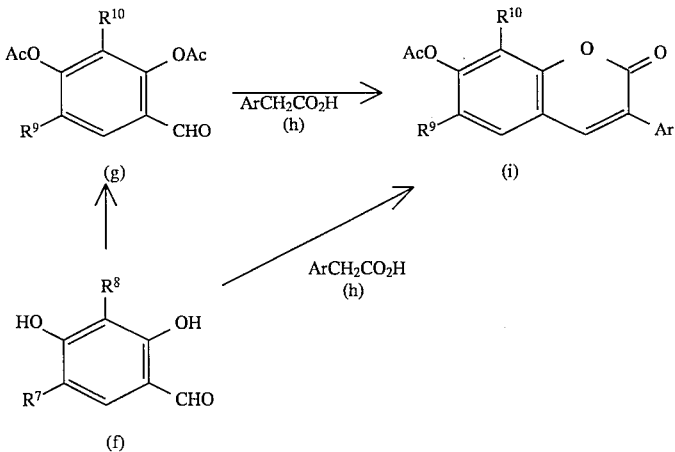

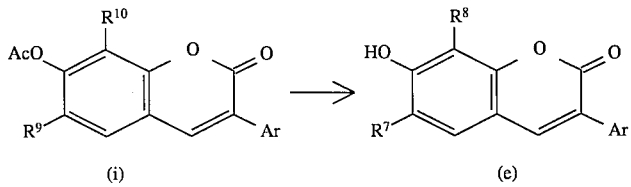

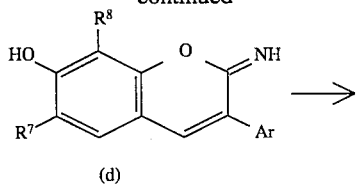

(wherein $R^7$ and $R^8$ represent hydrogen or hydroxy; and $R^9$ and $R^{10}$ represent hydrogen or acetoxy).

An acetylsalicylaldehyde derivative (g) and an appropriate arylacetic acid (h) are condensed under the reaction conditions known as the Perkin reaction. Namely, a compound (i) can be obtained by refluxing them moderately in acetic anhydride in the presence of a base such as triethylamine usually at a temperature of about 120° C. for one to several hours (Process B).

An acetylsalicylaldehyde derivative (g) can be obtained by acetylating a corresponding salicylaldehyde derivative (f) using an acetylating agent such as acetic anhydride or acetyl chloride; or a compound (f) may be converted to a compound (i) directly by acetylating a salicylaldehyde derivative (f) under ice-cooling or at room temperature in acetic anhydride in the presence of a base such as triethylamine, and transferring the formed acetylsalicylaldehyde derivative (g) to the above-mentioned Perkin reaction conditions directly. In this case, arylacetic acid (h) of the other raw material may be added at the time of the transferring to the Perkin reaction conditions or may be allowed to coexist at the stage of acetylation of a compound (f), namely, from the beginning of the reaction. Besides, alkali metal salts of the arylacetic acid may be used instead of a base such as triethylamine in the above reaction.

The obtained compound (i) may be converted to a compound (e) of the present invention according to hydrolysis (or ester exchange) under acid conditions. The object may be accomplished by performing reflux in a mixed solution of, for example, ethanol and hydrochloric acid, for 30 minutes to several hours (Process C).

The obtained compound of the present invention can be purified according to a known purification method such as recrystallization, chromatography and the like.

Since the above compound of the present invention has a selective 12-lipoxygenase inhibitory activities, it has a function of inhibiting the formation of 12-lipoxygenase metabolic products such as 12-HPETE and 12-HETE in vivo; and the medicine of the present invention having a selective 12-lipoxygenase inhibitory effect, which contain the compound as an effective ingredient, can be utilized as medicines for treating or preventing various circulatory diseases caused by these metabolic products such as arteriosclerosis and vasospasm, further as medicines for preventing the metastasis of some kinds of cancers (e.g., Lewis lung cancer) effectively.

The compounds of the present invention can be used as medicines with proper forms such as tablets, capsules, injections, granules and suppositories as they are or in admixture with a pharmaceutically acceptable known carrier, excipient or the like.

The medicines with the compounds of the present invention as effective ingredients can be administered orally or parenterally according to injection, inhalation, coating or the like.

The administration dose of the medicine of the present invention having a selective 12-lipoxygenase inhibitory effect, which contain the compound as an effective ingredient, may vary according to targets for treatments, conditions of patients, ages, terms of treatments or the like; preferably, about 0.1–50 mg are administered 1–3 times per day usually.

Next, the present invention will be described further in detail according to Test Examples.

Test Example 1

The test was performed to examine the inhibitory effect of various compounds on 12-lipoxygenase activity.

1) Preparation of Enzyme Solution

A Sprague Dawley male rat was anesthetized with ether and bled from abdominal aorta using a syringe filled with about one-tenth volume of 3.8% sodium citrate. Blood was centrifuged at 180×g for 15 minutes at room temperature to pellet sanguineous platelet blood plasma. The resultant supernatant was again centrifuged at 1800×g for 10 minutes at 4° C. The pelleted platelets were rinsed twice with a washing buffer (50 mM Tris-hydrochloric acid buffer containing 154 mM sodium chloride and 2 mM EDTA, pH: 7.4). The platelets were then suspended in one-twentieth volume of a resuspension buffer (50 mM Tris-hydrochloric acid buffer containing 154 mM sodium chloride and 5.5 mM glucose, pH: 7.4). The platelets were then sonicated at 4° C. and centrifuged at 100,000×g for 30 minutes to obtain a supernatant as a 12-lipoxygenase enzyme solution.

2) Procedure for 12-lipoxygenase inhibition assay

The enzyme solution described above was diluted with the resuspension buffer above mentioned to prepare an assay solution so as to include about 2 mU/ml of 12-lipoxygenase. To an aliquot (300 µl) of the assay solution was added 1 µl of a 3 mM indomethacin-ethanol solution, 1 µl of an aqueous 300 mM reduced-glutathione solution, and 3 µl of varied concentrated test compounds solution in ethanol. The resultant mixture was incubated at 37° C. for 5 minutes. Subsequently, 3 µl of a 2.5 mM arachidonic acid solution in ethanol was added to incubate with for another 5 minutes at 37° C., then the reaction was ceased by the addition of 600 µl of methanol. After being centrifuged at 10,000×g for 5 minutes, 12-hydroxyeicosatetraenoic acid recovered in the supernatant was separated with a reverse phase high-performance liquid chromatography equipped with a C-18 column and measured the absorption of diene at 234 nm to quantify the activity of 12-lipoxygenase.

As test compounds were used the compounds of the present invention prepared in the same methods as in Example 4, Example 5 and Example 8 and the compounds prepared in the same methods as in Comparative Examples 1–5, and as a control was used esculetin (purchased from Tokyo Kasei), a known compound represented by the following formula:

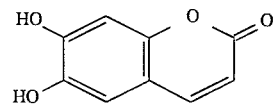

Formula 29 and the test was conducted at varied concentrations.

Values represent the concentration to produce 50% inhibition of 12-lipoxygenase activity were estimated from experimental data of each sample (hereinafter was described as the $IC_{50}$).

3) Results of the Test

The results of the test are as shown in Table 1. Table 1 showed 12-lipoxygenase $IC_{50}$ values of the compounds of Examples 4, 5 and 8 of the present invention and esculetin (purchased from Tokyo Kasei), a known compound used for a control, and 12-lipoxygenase inhibition ratios of the compounds of Comparative Examples 1–2 whose $IC_{50}$ values could not be obtained.

TABLE 1

| Results of the Test on Inhibitory Activity | |
|---|---|
| Compound | 12-lipoxygenase $IC_{50}$ value (M) |
| Example 4 | $7.6 \times 10^{-9}$ |
| Example 5 | $9.2 \times 10^{-9}$ |
| Example 8 | $7.0 \times 10^{-9}$ |
| Comp. Example 1 | * |
| Comp. Example 2 | ** |
| Comp. Example 3 | $2.6 \times 10^{-7}$ |
| Comp. Example 4 | $1.2 \times 10^{-7}$ |
| Comp. Example 5 | $1.1 \times 10^{-6}$ |
| Esculetin | $4.4 \times 10^{-6}$ |

Notes:
*: Though the $IC_{50}$ value was not obtained, the maximum inhibition ratio was 5% at a compound concentration of $10^{-5}$M.
**: Though the $IC_{50}$ value was not obtained, the maximum inhibition ratio was 7% at a compound concentration of $10^{-5}$M.

While the 12-lipoxygenase inhibitory activities of the compounds prepared in the same methods as in Example 4 and Example 8 of the present invention showed $IC_{50}$ values of $7.6 \times 10^{-9}$M and $7.0 \times 10^{-9}$M respectively, the compounds prepared in the same methods as in Comparative Example 1 and Comparative Example 2 were similar to the compounds of the present invention in chemical structures but the 12-lipoxygenase inhibitory activities thereof were very poor or not exhibited, and they exhibited an inhibition ratio of only less than 10% even at a concentration of $10^{-5}$M.

The results suggest that it is essential for the compounds of the present invention to have at least 2 catechol-type hydroxy groups at 6- to 8-positions of a coumarin ring so that they may express strong 12-lipoxygenase inhibitory activities.

The 12-lipoxygenase inhibitory activity of esculetin, which is a known compound used for a control and has been already reported upon its 12-lipoxygenase inhibitory activity, showed an $IC_{50}$ value of $4.4 \times 10^{-6}$M. On the other hand, the 12-lipoxygenase inhibitory activities of the compounds prepared in the same methods as in Example 4 and Example 8 of the present invention are very strong, all showing $IC_{50}$ values of the order of $10^{-9}$M.

The compounds of the present invention are characterized by having an aryl group at the 3-position of a coumarin ring. On the other hand, though the 12-lipoxygenase inhibitory activities of the compounds having an aryl group at the 4-position prepared in the same method as in Comparative Example 3 are relatively strong, showing $IC_{50}$ values of $2.6 \times 10^{-7}$, they can never be compared with the 12-lipoxygenase inhibitory activities of the compounds of the present invention.

In addition, though not shown in Table 1, the 5-lipoxygenase inhibitory activities of esculetin and the compound prepared in the same method as in Comparative Example 3 exhibited $IC_{50}$ values of $4.3 \times 10^{-6}$M and $6.4 \times 10^{-7}$M respectively and no selectivity was found in the inhibitory activities against 12-lipoxygenase and 5-lipoxygenase. On the contrary, the compounds of the present invention inhibit 12-lipoxygenase selectively as will be described later.

Hence, it is essential for the compounds of the present invention to have an aryl group at the 3-position of a coumarin ring so that they may express strong and selective 12-lipoxygenase inhibitory activities.

The 12-lipoxygenase inhibitory activity of the compound prepared in the same method as in Comparative Example 4 as an example of a compound having an aryl group at both 3-position and 4-position of a coumarin ring exhibited an $IC_{50}$ value of $1.2 \times 10^{-7}$M. On the other hand, the 12-lipoxygenase inhibitory activities of the compounds prepared in the same methods as in Example 4 and Example 8 and the compound of Example 5 having a methyl group at the 4-position of a coumarin ring were remarkably strong, exhibiting an $IC_{50}$ value of $9.2 \times 10^{-9}$M. The results suggest that it is preferable for the expression of strong 12-lipoxygenase inhibitory activities of the compounds of the present invention that the 4-position of a coumarin ring is non-substituted or has a three-dimensionally small substituent such as lower alkyl group.

As will be described later, those having a considerably voluminous substituent at the para-position or meta-position of the aryl group tended to show stronger 12-lipoxygenase inhibitory activities as compared with those non-substituted, as a characteristic of an aryl group at the 3-position of a coumarin ring of the compounds according to the present invention. Preferable substituents of them will be described later; as shown in the compound prepared in the same method as in Comparative Example 5, the 12-lipoxygenase inhibitory activity decreases greatly when the substituent of the para-position or meta-position of the aryl group is hydroxy.

Test Example 2

The test was carried out to examine the selectivity toward 12-lipoxygenase of the compounds of the first embodiment in the present invention.
1) Preparation of Enzyme Solution
① Preparation of 5-lipoxygenase enzyme solution
Rat basophilic leukemia cells (RBL-1, ATCC CRL1378) were cultured in Dulbecco modified Eagle's medium containing 10% new-born bovine serum.

Cultured cells were collected and washed twice with a 50 mM Tris-buffered saline (containing 154 mM sodium chloride, pH: 7.4, hereinafter described as TBS). The cell suspension ($4 \times 10^7$ cells/ml) was then sonicated and centrifuged at 10,000×g for 10 minutes.

The resultant supernatant was used to prepare an assay solution.
② Preparation of 12-lipoxygenase enzyme solution
The enzyme solution was prepared according to the same manner as in Test Example 1.
Method of Measurement of Enzymes Activity
① Procedure for 5-lipoxygenase inhibition assay
To an aliquot (15 µl) of the enzyme solution (40 mU/ml equivalent) was added 185 µl of TBS, 50 µl of a 2 mM adenosine triphosphate in TBS, 50 µl of a 12 mM calcium chloride in TBS, 1 µl of a 3 mM indomethacin in ethanol solution, 1 µl of an aqueous 300 mM reduced glutathione solution, and 3 µl of varied concentrated test compounds solution in ethanol. The resultant mixture was incubated at 37° C. for 5 minutes. Subsequently, 3 µl of a 2.5 mM arachidonic acid solution in ethanol was added to incubate the mixture for 2 minutes at 37° C. The reaction was ceased by the addition of 600 µl of methanol. After being centrifuged at 10,000×g for 5 minutes, 5-hydroxyeicosatetraenoic acid recovered in the supernatant was separated with a reverse phase high-performance liquid chromatography equipped with a C-18 column and measured the absorption of diene at 234 nm to quantify the activity of the enzyme.

Using the compounds of the present invention prepared in the same manner as in Examples 1–30, and Examples 33–36 as test samples and known baicalein (purchased from Wako Junyaku Kogyo) represented by the following formula 30 as a control:

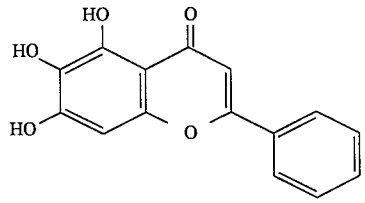

Formula 30 the tests were performed for dose dependent inhibition to estimate $IC_{50}$ values
② Procedure for 12-lipoxygenase inhibition assay
The inhibition assay was performed according to the same method as described in Test Example 1 except that the same samples used in measurement of the 5-lipoxygensase activity were used to estimate $IC_{50}$ values.
3) Results of the Test
The results of the test are as shown in Table 2. As is apparent from Table 2, the compounds of the present invention exhibited remarkably strong inhibitory activities against 12-lipoxygenase, showing $IC_{50}$ values of the order of $10^{-9}$M, which were equivalent to or more than that of known baicalein. On the other hand, the compounds of the present invention have inhibitory activities also against 5-lipoxygenase, and the $IC_{50}$ values thereof were 10 to more than 60 times those against 12-lipoxygenase. Hence, it was revealed that the compounds of the present invention have inhibitory activities against 12-lipoxygenase selectively.

In addition, of the compounds of the present invention, those having a substituent with a considerable size at the 3-position aryl group of a coumarin ring tend to exhibit stronger 12-lipoxygenase inhibitory activities; the para-position and the meta-position are preferable as the positions of substituents; and regarding kinds of substituents, fluorine, chlorine, bromine and iodine exhibited particularly remarkable 12-lipoxygenase inhibitory activities in case of halogen group, and methyl and ethyl, in case of alkyl group.

TABLE 2

Results of the Test on Selectivity of Inhibitory Effects

| Compound | $IC_{50}$ value of 12-lipoxygenase (M) | $IC_{50}$ value of 5-lipoxygenase (M) |
| --- | --- | --- |
| Example 1 | $4.4 \times 10^{-9}$ | $1.9 \times 10^{-7}$ |
| Example 4 | $7.6 \times 10^{-9}$ | $4.8 \times 10^{-7}$ |
| Example 5 | $9.2 \times 10^{-9}$ | $4.1 \times 10^{-7}$ |
| Example 6 | $1.6 \times 10^{-8}$ | $2.7 \times 10^{-7}$ |
| Example 7 | $8.0 \times 10^{-9}$ | $4.0 \times 10^{-7}$ |
| Example 8 | $7.0 \times 10^{-9}$ | $2.6 \times 10^{-7}$ |
| Example 9 | $4.3 \times 10^{-9}$ | $1.6 \times 10^{-7}$ |
| Example 10 | $5.8 \times 10^{-9}$ | $1.4 \times 10^{-7}$ |
| Example 11 | $1.1 \times 10^{-8}$ | $1.8 \times 10^{-7}$ |
| Example 12 | $1.1 \times 10^{-8}$ | $2.8 \times 10^{-7}$ |

TABLE 2-continued

Results of the Test on Selectivity of Inhibitory Effects

| Compound | $IC_{50}$ value of 12-lipoxygenase (M) | $IC_{50}$ value of 5-lipoxygenase (M) |
| --- | --- | --- |
| Example 14 | $1.3 \times 10^{-8}$ | $2.7 \times 10^{-7}$ |
| Example 15 | $2.1 \times 10^{-8}$ | $3.3 \times 10^{-7}$ |
| Example 16 | $2.2 \times 10^{-8}$ | $4.2 \times 10^{-7}$ |
| Example 19 | $1.4 \times 10^{-8}$ | $2.5 \times 10^{-7}$ |
| Example 22 | $9.6 \times 10^{-9}$ | $2.7 \times 10^{-7}$ |
| Example 23 | $3.4 \times 10^{-8}$ | $5.3 \times 10^{-7}$ |
| Example 25 | $1.3 \times 10^{-8}$ | $4.2 \times 10^{-7}$ |
| Example 27 | $2.7 \times 10^{-8}$ | $6.6 \times 10^{-7}$ |
| Example 33 | $1.2 \times 10^{-8}$ | $3.6 \times 10^{-7}$ |
| Example 34 | $5.2 \times 10^{-9}$ | $1.5 \times 10^{-7}$ |
| Example 35 | $1.5 \times 10^{-8}$ | $3.4 \times 10^{-7}$ |
| Example 36 | $1.4 \times 10^{-8}$ | $2.5 \times 10^{-7}$ |
| Baicalein | $4.2 \times 10^{-8}$ | $2.4 \times 10^{-6}$ |

The measured values of nuclear magnetic resonance spectra and infrared absorption spectra of the compounds according to the first embodiment of the present invention and the compounds for comparison were shown in Tables 3–10. The nuclear magnetic resonance spectra [$^1$H-NMR(500 MHz)] were measured in a DMSO-$d_6$ solvent and the infrared absorption spectra according to a KBr disk method respectively.

TABLE 3

| Example | Structural formula | $^1$H-NMR($\delta_{ppm}$) | IR($v_{cm}^{-1}$) |
| --- | --- | --- | --- |
| 1 | (structure: 6,7-dihydroxycoumarin with 3-(4-bromophenyl) substituent) | 6.78(1H, s), 7.07(1H, s), 7.62(2H, d), 7.68(2H, d), 8.15(1H, s) | 3500, 3070, 1680, 1665, 1630, 1615, 1570, 1515, 1490, 1420, 1375, 1345, 1300, 1230, 1180, 1160, 1080, 1000, 975, 830, 770, 710 |
| 2 | (structure: 7,8-dihydroxycoumarin with 3-(4-fluorophenyl) substituent) | 6.84(1H, d), 7.10(1H, d), 7.27(2H, t), 7.76(2H, dd), 8.12(1H, s) | 3560, 3540, 3200, 1680, 1620, 1580, 1510, 1475, 1415, 1385, 1360, 1345, 1315, 1300, 1245, 1220, 1190, 1165, 1140, 1090, 1030, 845, 830, 810, 775, 715, 695 |
| 3 | (structure: 7,8-dihydroxycoumarin with 3-(3-methylphenyl) substituent) | 2.36(3H, s), 6.83(1H, d), 7.10(1H, d), 7.19(1H, d), 7.32(1H, t), 7.49 (1H, d), 7.52(1H, s), 8.09(1H, s) | 3550, 3120, 1690, 1625, 1590, 1510, 1380, 1355, 1305, 1185, 1140, 1090, 1040, 795, 710 |
| 4 | (structure: 7,8-dihydroxycoumarin with 3-(4-chlorophenyl) substituent) | 6.84(1H, d), 7.11(1H, d), 7.50(2H, d), 7.75(2H, d), 8.17(1H, s) | 3470, 3250, 1685, 1605, 1590, 1570, 1490, 1470, 1410, 1295, 1240, 1215, 1205, 1175, 1095, 1080, 1030, 1010, 830, 770 |

TABLE 3-continued

| Example | Structural formula | $^1$H-NMR($\delta_{ppm}$) | IR($\nu_{cm}^{-1}$) |
|---|---|---|---|
| 5 | HO, HO substituted chromone with Me and 4-Cl-phenyl | 2.16(3H, s), 6.77(1H, s), 7.08(1H, s), 7.32(2H, d), 7.49(2H, d) | 3350, 1665, 1630, 1575, 1560, 1525, 1495, 1455, 1420, 1400, 1340, 1285, 1200, 1180, 1090, 1075, 1020, 980, 860, 765 |

TABLE 4

| Example | Structural formula | $^1$H-NMR($\delta_{ppm}$) | IR($\nu_{cm}^{-1}$) |
|---|---|---|---|
| 6 | HO, HO substituted chromone with phenyl | 6.78(1H, s), 7.07(1H, s), 7.37(1H, t), 7.43(2H, t), 7.69(2H, t), 8.09(1H, s) | 3500, 3200, 1670, 1620, 1600, 1580, 1560, 1500, 1460, 1425, 1360, 1300, 1260, 1240, 1210, 1175, 1150, 980, 960, 860, 790, 770, 720, 700 |
| 7 | HO, HO substituted chromone with 4-F-phenyl | 6.78(1H, s), 7.06(1H, s), 7.26(2H, t), 7.75(2H, dd), 8.10(1H, s) | 3530, 3430, 3170, 1690, 1620, 1575, 1510, 1420, 1355, 1300, 1255, 1200, 1160, 980, 860, 835, 810, 775, 730 |
| 8 | HO, HO substituted chromone with 4-Cl-phenyl | 6.78(1H, s), 7.06(1H, s), 7.49(2H, d), 7.74(2H, d), 8.15(1H, s) | 3400, 1695, 1660, 1625, 1580, 1520, 1495, 1455, 1415, 1295, 1200, 1155, 1095, 1015, 980, 860, 825, 770, 720 |
| 9 | HO, HO substituted chromone with 3-Cl-phenyl | 6.79(1H, s), 7.08(1H, s), 7.43(1H, d), 7.46(1H, t), 7.69(1H, d), 7.79(1H, s), 8.21(1H, s) | 3400, 1670, 1630, 1600, 1580, 1480, 1460, 1415, 1310, 1300, 1260, 1205, 1180, 1155, 790, 710 |
| 10 | HO, HO substituted chromone with 4-I-phenyl | 6.78(1H, s), 7.06(1H, s), 7.52(2H, d), 7.79(2H, d), 8.14(1H, s) | 3400, 1690, 1660, 1625, 1575, 1520, 1490, 1450, 1410, 1290, 1250, 1060, 1005, 980, 860, 820, 770, 730 |

TABLE 5

| Example | Structural formula | $^1$H-NMR($\delta_{ppm}$) | IR($\nu_{cm}^{-1}$) |
|---|---|---|---|
| 11 | HO, HO substituted chromone with 4-Me-phenyl | 2.34(3H, s), 6.77(1H, s), 7.06(1H, s), 7.24(2H, d), 7.60(2H, d), 8.06(1H, s) | 3530, 3200, 1695, 1640, 1580, 1515, 1455, 1420, 1390, 1345, 1300, 1250, 1220, 1200, 1175, 980, 860, 810, 775, 765, 730 |

TABLE 5-continued

| Example | Structural formula | ¹H-NMR($\delta_{ppm}$) | IR($\nu_{cm}^{-1}$) |
|---|---|---|---|
| 12 | 3,4-dihydroxybenzylidene-(3-methylphenyl) coumarin derivative | 2.35(3H, s), 6.78(1H, s), 7.06(1H, s), 7.18 (1H, d), 7.31(1H, t), 7.48(1H, d), 7.51(1H, s), 8.08(1H, s) | 3350, 1650, 1600, 1555, 1430, 1390, 1275, 1230, 1185, 1155, 840, 770, 700 |
| 13 | 3,4-dihydroxybenzylidene-(4-ethylphenyl) coumarin derivative | 1.20(3H, t), 2.64(2H, q), 6.76(1H, s), 7.05 (1H, s), 7.26(2H, d), 7.61(2H, d), 8.05 (1H, s) | 3300, 2960, 1660, 1625, 1580, 1570, 1450, 1420, 1300, 1230, 980, 930, 860, 830, 720 |
| 14 | 3,4-dihydroxybenzylidene-(4-trifluoromethylphenyl) coumarin derivative | 6.80(1H, s), 7.09(1H, s), 7.79(2H, d), 7.94 (2H, d), 8.25(1H, s) | 3400, 1700, 1660, 1625, 1575, 1520, 1460, 1420, 1410, 1340, 1330, 1300, 1240, 1180, 1170, 1140, 1070, 1020, 980, 870, 860, 780, 720, 695 |
| 15 | 3,4-dihydroxybenzylidene-(2-thienyl) coumarin derivative | 6.80(1H, s), 7.07(1H, s), 7.15(1H, dd), 7.59(1H, d), 7.76(1H, d), 8.42(1H, s) | 3420, 1675, 1625, 1610, 1570, 1515, 1455, 1410, 1335, 1295, 1260, 1200, 1150, 770, 700 |

TABLE 6

| Example | Structural formula | ¹H-NMR($\delta_{ppm}$) | IR($\nu_{cm}^{-1}$) |
|---|---|---|---|
| 16 | 3,4-dihydroxybenzylidene-(3-thienyl) coumarin derivative | 6.78(1H, s), 7.05(1H, s), 7.62(1H, dd), 7.67(1H, dd), 8.14(1H, dd), 8.33(1H, s) | 3450, 1670, 1620, 1570, 1510, 1450, 1410, 1330, 1290, 1205, 1150, 1090, 925, 860, 800, 760, 710 |
| 17 | 2,3-dihydroxybenzylidene-phenyl coumarin derivative | 6.83(1H, d), 7.10(1H, d), 7.38(1H, t), 7.44(2H, t), 7.70(2H, d), 8.11(1H, s) | 3550, 3120, 1690, 1620, 1585, 1510, 1475, 1450, 1390, 1370, 1325, 1250, 1215, 1190, 1140, 1090, 1040, 1025, 800, 795, 705, 700 |
| 18 | 2,3-dihydroxybenzylidene-(4-methylphenyl) coumarin derivative | 2.35(3H, s), 6.83(1H, d), 7.09(1H, d), 7.25(2H, d), 7.61(2H, d), 8.08(1H, s) | 3550, 3200, 1690, 1620, 1590, 1520, 1510, 1480, 1420, 1395, 1360, 1320, 1310, 1210, 1190, 1130, 1095, 1030, 1020, 830, 780, 720 |
| 19 | 2,3-dihydroxybenzylidene-(4-ethylphenyl) coumarin derivative | 1.21(3H, t), 2.64(2H, q), 6.81(1H, d), 7.07(1H, d), 7.27(2H, d), 7.62(2H, d), 8.07(1H, s) | 3550, 3400, 3200, 2970, 1690, 1620, 1590, 1520, 1390, 1360, 1320, 1180, 1090, 1040, 1020, 840 |

TABLE 6-continued

| Example | Structural formula | ¹H-NMR(δ_ppm) | IR(ν_cm⁻¹) |
|---|---|---|---|
| 20 | (3,4-dihydroxyphenyl coumarin with 4-CF₃ phenyl) | 6.85(1H, d), 7.13(1H, d), 7.80(2H, d), 7.95(2H, d), 8.26(1H, s) | 3430, 3330, 1700, 1610, 1590, 1500, 1470, 1415, 1340, 1325, 1295, 1240, 1180, 1120, 1070, 1030, 1015, 845, 770, 695 |

TABLE 7

| Example | Structural formula | ¹H-NMR(δ_ppm) | IR(ν_cm⁻¹) |
|---|---|---|---|
| 21 | (3,4-dihydroxyphenyl coumarin with 3-thienyl) | 6.85(1H, d), 7.09(1H, d), 7.63(1H, dd), 7.67(1H, dd), 8.15(1H, dd), 8.36(1H, s) | 3450, 3320, 3150, 1695, 1620, 1610, 1590, 1530, 1500, 1480, 1420, 1400, 1385, 1345, 1310, 1290, 1255, 1225, 1180, 1120, 1090, 1080, 1035, 925, 845, 815, 800, 700 |
| 22 | (3,4-dihydroxyphenyl coumarin with 3-Cl phenyl) | 6.85(1H, d), 7.12(1H, d), 7.44(1H, d), 7.47(1H, t), 7.69(1H, d), 7.80(1H, s), 8.23(1H, s) | 3550, 3250, 1695, 1620, 1595, 1515, 1425, 1395, 1360, 1340, 1315, 1140, 1090, 1030, 805, 785, 700, 685 |
| 23 | (3,4-dihydroxyphenyl coumarin with 4-NO₂ phenyl) | 6.87(1H, d), 7.16(1H, d), 8.03(2H, d), 8.30(2H, d), 8.36(1H, s) | 3475, 3200, 1675, 1615, 1600, 1590, 1510, 1345, 1320, 1215, 1095, 1030, 855, 780, 710, 690 |
| 25 | (3,4-dihydroxyphenyl coumarin with 4-Br phenyl) | 6.84(1H, d), 7.11(1H, d), 7.64(2H, d), 7.69(2H, d), 8.17(1H, s) | 3550, 3380, 1715, 1610, 1595, 1515, 1495, 1475, 1410, 1345, 1315, 1295, 1240, 1220, 1210, 1125, 1080, 1030, 1010, 910, 825, 780, 770, 710 |
| 27 | (3,4-dihydroxyphenyl coumarin with 4-OMe phenyl) | 3.80(3H, s), 6.81(1H, d), 7.00(2H, d), 7.07(1H, d), 7.66(2H, d), 8.04(1H, s) | 3320, 1705, 1615, 1595, 1525, 1480, 1315, 1290, 1260, 1240, 1190, 1140, 1090, 1040, 1020, 840, 780, 700 |

TABLE 8

| Example | Structural formula | $^1$H-NMR($\delta_{ppm}$) | IR($\nu_{cm}^{-1}$) |
|---|---|---|---|
| 29 | (3,4-dihydroxy coumarin with 2-thienyl substituent) | 6.86(1H, d), 7.13(1H, d), 7.16(1H, dd), 7.61 (1H, dd), 7.77(1H, dd), 8.44(1H, s) | 3540, 3420, 3330, 1680, 1605, 1580, 1515, 1480, 1430, 1320, 1310, 1300, 1220, 1210, 1185, 1090, 1030, 815, 775, 770, 710, 700 |
| 30 | (6,7-dihydroxy coumarin with Me and phenyl substituents) | 2.15(3H, s), 6.76(1H, s), 7.07(1H, s), 7.28 (2H, d), 7.37(1H, t), 7.44(2H, t) | 3490, 3180, 1650, 1620, 1560, 1450, 1420, 1345, 1290, 1200, 1175, 1150, 1075, 975, 865, 790, 705 |

TABLE 9

| Example | Structural formula | $^1$H-NMR($\delta_{ppm}$) | IR($\nu_{cm}^{-1}$) |
|---|---|---|---|
| 33 | (3,4-dihydroxy coumarin with 4-bromo-2-thienyl substituent) | 6.87(1H, d), 7.11(1H, d), 7.71(1H, d), 7.78(1H, d), 8.57(1H, s) | 3460, 3350, 3120, 1690, 1620, 1605, 1580, 1520, 1510, 1475, 1415, 1385, 1355, 1340, 1320, 1290, 1215, 1180, 1120, 1085, 1025, 730 |
| 34 | (6,7-dihydroxy coumarin with 4-bromo-2-thienyl substituent) | 6.79(1H, s), 7.05(1H, s), 7.69(1H, d), 7.76(1H, d), 8.55(1H, s) | 3350, 3120, 1665, 1620, 1580, 1520, 1460, 1415, 1370, 1345, 1270, 1255, 1235, 1200, 970, 930, 870, 830, 750 |
| 35 | (3,4-dihydroxy coumarin with 5-methyl-2-furyl substituent) | 2.36(3H, s), 6.24(1H, d), 6.83(1H, d), 6.98(1H, d), 7.17(1H, d), 8.12(1H, s) | 3500, 3400, 3200, 1705, 1630, 1590, 1500, 1400, 1390, 1345, 1320, 1255, 1225, 1210, 1160, 1095, 1050, 1030, 795, 780 |
| 36 | (6,7-dihydroxy coumarin with 5-methyl-2-furyl substituent) | 2.36(3H, s), 6.23(1H, d), 6.77(1H, s), 6.95(1H, d), 7.12(1H, s), 8.10(1H, s) | 3480, 3240, 1690, 1625, 1605, 1580, 1525, 1455, 1425, 1340, 1300, 1250, 1240, 1200, 1150, 1025, 920, 860, 810, 770, 720 |

TABLE 10

| Comparative Example | Structural formula | $^1$H-NMR($\delta_{ppm}$) | IR($\nu_{cm}^{-1}$) |
|---|---|---|---|
| 1 | (7,8-dimethoxy-3-phenyl coumarin) | 3.87(3H, s), 3.93(3H, s), 7.16(1H, d), 7.40(1H, t), 7.46(2H, t), 7.51(1H, d), 7.71 (2H, d), 8.20(1H, s) | 3020, 2940, 2850, 1720, 1610, 1505, 1470, 1450, 1430, 1370, 1310, 1290, 1250, 1210, 1190, 1175, 1130, 1100, 1080, 980, 820, 790, 700 |

TABLE 10-continued

| Comparative Example | Structural formula | $^1$H-NMR($\delta_{ppm}$) | IR($\nu_{cm}^{-1}$) |
|---|---|---|---|
| 2 | (structure: coumarin with HO- and 4-Cl-phenyl) | 6.76(1H, d), 6.83(1H, dd), 7.50(2H, d), 7.61(1H, d), 7.74(2H, d), 8.21(1H, s) | 3230, 1680, 1620, 1600, 1500, 1460, 1410, 1370, 1300, 1265, 1235, 1220, 1170, 1130, 1095, 995, 860, 780, 720 |
| 3 | (structure: dihydroxy coumarin with phenyl) | 6.13(1H, s), 6.76(1H, ABtype d), 6.79 (1H, ABtype d), 7.50(2H, m), 7.55 (3H, m) | 3380, 1670, 1600, 1570, 1510, 1470, 1450, 1380, 1310, 1290, 1275, 1250, 1220, 1185, 1075, 1035, 1025, 865, 820, 790, 780, 770, 730, 705, 700 |
| 4 | (structure: dihydroxy coumarin with two phenyl) | 6.37(1H, d), 6.74(1H, d), 7.10–7.18 (7H, m), 7.29(3H, m) | 3520, 3330, 2990, 1710, 1610, 1585, 1565, 1520, 1500, 1465, 1455, 1380, 1340, 1310, 1290, 1215, 1205, 1180, 1150, 1080, 1040, 795, 765, 705 |
| 5 | (structure: dihydroxy coumarin with 4-OH-phenyl) | 6.81(1H, d), 6.82(2H, d), 7.06(1H, d), 7.55(2H, d), 7.98(1H, s) | 3360, 1690, 1665, 1605, 1580, 1520, 1510, 1450, 1390, 1370, 1330, 1310, 1295, 1270, 1220, 1180, 1100, 1030, 1010, 930, 855, 840, 835, 810, 785, 780, 725, 700 |

Test Example 3

The test was performed to examine the 12-lipoxygenase inhibitory activities of the compounds which were formed by the absorption in vivo and deacylation of the compounds of the third embodiment of the present invention.

1) Preparation of Enzyme Solution

The enzyme solution was prepared in the same method as in Test Example 1.

2) Method of Measurement Enzymes Activity

They were measured in the same method as in Test Example 1 and $IC_{50}$ values were estimated from the measured values of test compounds.

3) Results of the Test

The results of the test are as shown in Table 11. Table 11 showed the 12-lipoxygenase $IC_{50}$ values of the compounds (the compounds of Comp.Ex.6–8,16, Ref.Ex.8,13 and Example 43) formed by the absorption in vivo and deacylation of the compounds of Examples 37–40, 43, 54, and 56–58 and baicalein (purchased from Wako Junyaku Kogyo), a known compound used for a control.

As is apparent from Table 11, it was revealed that the 12-lipoxygenase inhibitory activity of the compound of each Example according to the present invention is far more excellent than that of baicalein. As a result of performing a test about other compounds of the present invention, almost the same results were obtained.

TABLE 11

| Compounds of the Present invention (acylated compounds) | Deacylated compounds | 12-lipoxygenase inhibiting activities of deacylated compounds* |
|---|---|---|
| Example 37 (formula 37b) | Comp. Ex. 6 (formula 38b) | $7.6 \times 10^{-9}$ (M) |
| Example 38 (formula 39b) | Comp. Ex. 7 (formula 40b) | $7.0 \times 10^{-9}$ |
| Example 39 (formula 41b) | Comp. Ex. 8 (formula 42b) | $9.6 \times 10^{-9}$ |
| Example 40 (formula 43b) | Ref. Ex. 8 (formula 34b) | $4.3 \times 10^{-9}$ |
| Example 43 (formula 48b) | Example 43 (formula 47b) | $5.8 \times 10^{-9}$ |
| Example 54 (formula 69b) | Comp. Ex. 16 (formula 70b) | $5.2 \times 10^{-9}$ |
| Example 56 (formula 73b) | Ref. Ex. 13 (formula 35b) | $9.2 \times 10^{-9}$ |
| Example 57 (formula 74b) | Ref. Ex. 8 (formula 34b) | $4.3 \times 10^{-9}$ |
| Example 58 (formula 75b) | Ref. Ex. 8 (formula 34b) | $4.3 \times 10^{-9}$ |
| Baicalein | | $4.2 \times 10^{-8}$ |

Note:
*: $IC_{50}$ values

Test Example 4

The test was performed to examine whether or not deacylated compounds would be formed due to esterases present in the enzyme solution when the compounds in the third embodiment according to the present invention were treated with the same enzyme solution as in Test Example 3.

1) Preparation of Enzyme Solution

The enzyme solution was prepared according to the same procedure as described in Test Example 1.

2) Method of the Test

One ml of the above mentioned enzyme solution was diluted with 11 ml of a resuspension buffer. To an aliquot (300 μl) of this enzyme solution was added 3 μl of a $1.0 \times 10^{-3}$M test compound solution in dimethyl sulfoxide. The mixture was incubated at 37° C. for an indicated time, then the reaction was ceased by the addition of 1 ml of acetonitrile. Twenty μl of the above mixture was subjected to reverse phase high-performance liquid chromatography equipped with a C-18 column to quantify the amount of deacylated products. As a control, a test using 300 μl of the resuspension buffer solution mentioned above instead of the enzyme solution was also performed.

Conditions of reverse phase high-performance liquid chromatography:

Column: Superspher RP-18(e) (purchased from Merck), 4.0 mm in diameter, 125 mm in length Flow velocity: 1.0 ml/minute Eluent: Acetonitrile containing 50 mM $NaClO_4$ and 50 mM orthophosphate-water (55:45)

Column temperature: 30° C.

Calibration: Absorbance of 280 nm

3) Results of the Test

The results of the test upon the compounds of Example 40 (Formula 43b) and Example 57 (Formula 74b) of the compounds according to the present invention will be shown. Since both the compounds of Example 40 (Formula 43b) and Example 57 (Formula 74b) are thought to be converted into the compound of Referential Example 8 (Formula 34b) through deacylation, the retention time of the compound of Referential Example 8 was checked strictly under the employed conditions with reverse phase high-performance liquid chromatography mentioned above (retention time: 2.49 minutes) and a calibration curve of the compound was made using authentic sample of Referential Example 8.

As a case of using the resuspension buffer instead of the enzyme solution, no deacylated compound (Formula 34b) was formed from both compounds of Example 40 (Formula 43b) and Example 57 (Formula 74b).

When the similar test was performed using the above enzyme solution, the both compounds were deacylated with increasing times, and the deacylated compound (Formula 34b) was observed in the reaction solution as shown in Table 12.

These results clearly revealed that in the compounds of the present invention, modified moieties are cleaved relatively rapidly to form deacylated compound when contacted with an enzyme solution (maybe containing a kind of esterase in addition to 12-lipoxygenase) prepared from rat platelets.

On the other hand, the compounds formed through deacylation revealed a remarkably strong inhibitory activity against 12-lipoxygenase as shown in Test Example 3. The compounds described in the present invention were regarded as precursors to form compounds having inhibitory effect on 12-lipoxygenase and can be therefore utilized as so-called pro-drugs.

Although other compounds in the present invention were also tested, almost the same results were obtained.

TABLE 12

| Compound | Reaction time (minute) | |
|---|---|---|
| | 30 | 60 |
| Formula 43b | 70.7 | 72.8 |
| Formula 74b | 42.4 | 60.4 |

Note: Values show conversion ratios (%) from Formula 43b or Formula 74b to Formula 34b.

The measured values of nuclear magnetic resonance spectra and infrared absorption spectra of the compounds according to the third embodiment of the present invention and the compounds for comparison were shown in Tables 13–21. The nuclear magnetic resonance spectra [$^1$H-NMR (500 MHz)] were measured in a DMSO-$d_6$ solvent with tetramethylsilane as an internal standard and the infrared absorption spectra according to a KBr disk method respectively.

TABLE 13

| Compound | Structural formula | $^1$H-NMR(DMSO-$d_6$, $\delta_{ppm}$) | IR($v_{cm}^{-1}$) |
|---|---|---|---|
| Formula 37b | [structure with $CH_3COO$ groups, O, and Cl-phenyl] | 2.35(3H, s), 2.43(3H, s), 7.34(1H, d), 7.56(2H, d), 7.74(1H, d), 7.76 (2H, d), 8.35(1H, s) | 1790, 1740, 1720, 1630, 1620, 1500, 1460, 1375, 1270, 1250, 1200, 1170, 1090, 1080, 1060, 1015, 840, 770, 730 |
| Formula 39b | [structure with $CH_3COO$ groups, O, and Cl-phenyl] | 2.33(6H, s), 7.50(1H, s), 7.55(2H, d), 7.71(1H, s), 7.76(2H, d), 8.26 (1H, s) | 3070, 1770, 1730, 1630, 1580, 1495, 1430, 1380, 1290, 1265, 1210, 1190, 1170, 1130, 1090, 1020, 965, 830, 790, 750 |

TABLE 13-continued

| Compound | Structural formula | $^1$H-NMR(DMSO-$d_6$, $\delta_{ppm}$) | IR($\nu_{cm}^{-1}$) |
|---|---|---|---|
| Formula 41b | (3-acetoxy-4-acetoxy coumarin with 3-chlorophenyl) | 2.35(3H, s), 2.43(3H, s), 7.35(1H, d), 7.52(2H, m), 7.70(1H, m), 7.74 (1H, d), 7.80(1H, s), 8.39(1H, s) | 1780, 1740, 1615, 1600, 1580, 1560, 1500, 1460, 1375, 1360, 1300, 1260, 1245, 1210, 1170, 1080, 1040, 820, 800, 770, 725, 690 |
| Formula 43b | (6,7-diacetoxy coumarin with 3-chlorophenyl) | 2.33(6H, s), 7.51(1H, s), 7.49–7.54(2H, m), 7.68–7.72(1H, m), 7.71(1H, s), 7.80(1H, m), 8.31 (1H, s) | 3080, 1780, 1735, 1630, 1595, 1580, 1500, 1485, 1440, 1385, 1290, 1210, 1190, 1140, 1090, 1020, 910, 795, 750, 690 |
| Formula 44b | (3,4-diacetoxy coumarin with 4-fluorophenyl) | 2.35(3H, s), 2.43(3H, s), 7.32(2H, dd), 7.34(1H, d), 7.73(1H, d), 7.77(2H, dd), 8.31(1H, s) | 1780, 1725, 1620, 1515, 1495, 1465, 1380, 1300, 1265, 1250, 1210, 1080, 1040, 920, 840, 775, 770, 730 |

TABLE 14

| Compound | Structural formula | $^1$H-NMR(DMSO-$d_6$, $\delta_{ppm}$) | IR($\nu_{cm}^{-1}$) |
|---|---|---|---|
| Formula 45b | (3,4-diacetoxy coumarin with 4-bromophenyl) | 2.35(3H, s), 2.38(3H, s), 7.34 (1H, d), 7.69(4H, s), 7.74(1H, d), 8.35(1H, s) | 1780, 1735, 1620, 1500, 1460, 1375, 1310, 1270, 1250, 1200, 1170, 1080, 1070, 1040, 1010, 770, 730 |
| Formula 48b | (6,7-diacetoxy coumarin with 4-iodophenyl) | 2.33(6H, s), 7.49(1H, s), 7.53 (2H, d), 7.71(1H, s), 7.85(2H, d), 8.25(1H, s) | 1780, 1740, 1630, 1575, 1505, 1430, 1375, 1295, 1210, 1135, 1010, 970, 830, 790 |
| Formula 49b | (3,4-diacetoxy coumarin with 4-methylphenyl) | 2.35(3H, s), 2.36(3H, s), 2.42 (3H, s), 7.29(2H, d), 7.32(1H, d), 7.62(2H, d), 7.73(1H, d), 8.27(1H, s) | 1785, 1725, 1620, 1520, 1500, 1465, 1375, 1310, 1270, 1250, 1205, 1190, 1170, 1080, 1045, 925, 830, 775, 730 |
| Formula 51b | (3,4-diacetoxy coumarin with 3-methylphenyl) | 2.35(3H, s), 2.37(3H, s), 2.43 (3H, s), 7.26(1H, d), 7.33(1H, d), 7.36(1H, t), 7.51(2H, m), 7.74(1H, d), 8.28(1H, s) | 1790, 1770, 1750, 1620, 1500, 1480, 1380, 1255, 1210, 1190, 1170, 1110, 1080, 1040, 790, 720 |

TABLE 14-continued

| Compound | Structural formula | $^1$H-NMR(DMSO-$d_6$, $\delta_{ppm}$) | IR($\nu_{cm}^{-1}$) |
|---|---|---|---|
| Formula 54b | (CH$_3$COO, CH$_3$COO substituents on benzofuran-coumarin core with 4-C$_2$H$_5$-phenyl) | 1.21(3H, t), 2.33(6H, s), 2.66 (2H, q), 7.31(2H, d), 7.48(1H, s), 7.64(2H, d), 7.70(1H, s), 8.19(1H, s) | 3060, 2970, 1780, 1770, 1730, 1625, 1500, 1430, 1375, 1290, 1265, 1230, 1170, 1130, 1100, 1015, 965, 840 |

TABLE 15

| Compound | Structural formula | $^1$H-NMR(DMSO-$d_6$, $\delta_{ppm}$) | IR($\nu_{cm}^{-1}$) |
|---|---|---|---|
| Formula 56b | (CH$_3$COO, CH$_3$COO substituents; 4-CF$_3$-phenyl) | 2.33(3H, s), 2.34(3H, s), 7.53(1H, s), 7.74(1H, s), 7.85(2H, d), 7.95 (2H, d), 8.34(1H, s) | 3060, 1780, 1720, 1630, 1620, 1580, 1500, 1430, 1370, 1330, 1290, 1210, 1190, 1170, 1130, 1070, 1015, 855 |
| Formula 57b | (CH$_3$COO, CH$_3$COO substituents; 4-OCH$_3$-phenyl) | 2.35(3H, s), 2.42(3H, s), 3.81(3H, s), 7.04(2H, d), 7.32(1H, d), 7.69 (2H, d), 7.72(1H, d), 8.24(1H, s) | 1775, 1720, 1610, 1520, 1460, 1405, 1255, 1200, 1180, 1170, 1080, 1040, 1020, 920, 845, 770, 730 |
| Formula 59b | (CH$_3$COO, CH$_3$COO substituents; 4-NO$_2$-phenyl) | 2.36(3H, s), 2.44(3H, s), 7.37(1H, d), 7.79(1H, d), 8.02(2H, d), 8.34 (2H, d), 8.50(1H, s) | 1790, 1780, 1720, 1615, 1600, 1460, 1375, 1350, 1305, 1260, 1250, 1200, 1170, 1085, 1040, 860, 780, 720 |
| Formula 62b | (CH$_3$COO, CH$_3$COO substituents; phenyl) | 2.33(6H, s), 7.42–7.49(3H, m), 7.50(1H, s), 7.71(1H, s), 7.72(2H, d), 8.22(1H, s) | 3080, 1780, 1765, 1730, 1630, 1580, 1500, 1455, 1425, 1375, 1290, 1220, 1185, 1135, 1110, 1020, 915, 785, 700 |
| Formula 64b | (CH$_3$COO, CH$_3$COO substituents; 2-thienyl) | 2.330(3H, s), 2.333(3H, s), 7.21 (1H, dd), 7.51(1H, s), 7.71(1H, s), 7.72(1H, dd), 7.86(1H, dd), 8.54 (1H, s) | 1780, 1735, 1630, 1500, 1440, 1375, 1350, 1290, 1260, 1215, 1195, 1180, 1160, 1015, 940, 920, 730, 720 |

TABLE 16

| Compound | Structural formula | $^1$H-NMR(DMSO-$d_6$, $\delta_{ppm}$) | IR($\nu_{cm}^{-1}$) |
|---|---|---|---|
| Formula 65b | (3-thienyl coumarin diacetate) | 2.35(3H, s), 2.43(3H, s), 7.33(1H, d), 7.69(2H, m), 7.71(1H, d), 8.22(1H, m), 8.53(1H, s) | 3130, 1775, 1735, 1620, 1495, 1470, 1380, 1290, 1275, 1260, 1220, 1175, 1100, 1080, 1045, 820, 810, 770 |
| Formula 67b | (3-bromothienyl coumarin diacetate) | 2.35(3H, s), 2.43(3H, s), 7.37(1H, d), 7.72(1H, d), 7.83(1H, d), 7.88(1H, d), 8.74(1H, s) | 3100, 1790, 1725, 1610, 1510, 1490, 1460, 1415, 1380, 1345, 1265, 1210, 1165, 1080, 1040, 740 |
| Formula 69b | (3-bromothienyl coumarin diacetate isomer) | 2.33(3H, s), 2.34(3H, s), 7.54(1H, s), 7.67(1H, s), 7.84(1H, d), 7.87(1H, d), 8.66(1H, s) | 3125, 3090, 1780, 1725, 1625, 1570, 1500, 1435, 1375, 1340, 1285, 1210, 1190, 1140, 1100, 1015, 780, 750 |
| Formula 72b | (5-methylfuryl coumarin diacetate) | 2.32(3H, s), 2.33(3H, s), 2.39(3H, s), 6.31(1H, m), 7.12(1H, d), 7.47(1H, s), 7.79(1H, s), 8.24(1H, s) | 1780, 1740, 1630, 1530, 1500, 1420, 1375, 1300, 1210, 1190, 1170, 1140, 1120, 1020, 800, 775 |
| Formula 73b | (4-chlorophenyl methyl coumarin diacetate) | 2.23(3H, s), 2.32(3H, s), 2.33(3H, s), 7.37(2H, d), 7.49(1H, s), 7.53(2H, d), 7.80(1H, s) | 1780, 1720, 1630, 1580, 1570, 1500, 1430, 1390, 1380, 1290, 1210, 1190, 1165, 1140, 1100, 1075, 1020, 970, 910, 790 |

TABLE 17

| Compound | Structural formula | $^1$H-NMR(DMSO-$d_6$, $\delta_{ppm}$) | IR($\nu_{cm}^{-1}$) |
|---|---|---|---|
| Formula 74b | (3-chlorophenyl coumarin dipropanoate) | 1.15(6H, t), 2.65(4H, q), 7.51(1H, s), 7.49–7.54(2H, m), 7.67–7.71(1H, m), 7.71(1H, s), 7.80(1H, m), 8.31(1H, s) | 3080, 2980, 1780, 1735, 1620, 1575, 1500, 1430, 1360, 1290, 1280, 1220, 1180, 1135, 1100, 1080, 980, 910, 800, 680 |
| Formula 75b | (3-chlorophenyl coumarin dibutanoate) | 0.98(6H, t), 1.67(4H, hex), 2.60(4H, t), 7.51(1H, s), 7.49–7.54(2H, m), 7.67–7.72(1H, m), 7.71(1H, s), 7.80(1H, m), 8.31(1H, s) | 3080, 2950, 2940, 2880, 1780, 1760, 1740, 1620, 1575, 1500, 1425, 1360, 1290, 1275, 1220, 1160, 1130, 1100, 1070, 980, 800 |

TABLE 18

| Compound | Structural formula | $^1$H-NMR(DMSO-d$_6$, δ$_{ppm}$) | IR(ν$_{cm}^{-1}$) |
|---|---|---|---|
| Formula 38b | HO, HO-phenyl-O-C(=O)-CH=C-(4-Cl-phenyl) coumarin structure | 6.84(1H, d), 7.11(1H, d), 7.50(2H, d), 7.75 (2H, d), 8.17(1H, s) | 3470, 3250, 1685, 1605, 1590, 1570, 1490, 1470, 1410, 1295, 1240, 1215, 1205, 1175, 1095, 1080, 1030, 1010, 830, 770 |
| Formula 40b | HO, HO-phenyl coumarin with 4-Cl-phenyl | 6.78(1H, s), 7.06(1H, s), 7.49(2H, d), 7.74 (2H, d), 8.15(1H, s) | 3400, 1695, 1660, 1625, 1580, 1520, 1495, 1455, 1415, 1295, 1200, 1155, 1095, 1015, 980, 860, 825, 770, 720 |
| Formula 42b | HO, HO-phenyl coumarin with 3-Cl-phenyl | 6.85(1H, d), 7.12(1H, d), 7.44(1H, d), 7.47 (1H, t), 7.69(1H, d), 7.80(1H, s), 8.23(1H, s) | 3550, 3250, 1695, 1620, 1595, 1515, 1425, 1395, 1360, 1340, 1315, 1140, 1090, 1030, 805, 785, 700, 685 |
| Formula 34b | HO, HO-phenyl coumarin with 3-Cl-phenyl | 6.79(1H, s), 7.08(1H, s), 7.43(1H, d), 7.46 (1H, t), 7.69(1H, d), 7.79(1H, s), 8.21(1H, s) | 3400, 1670, 1630, 1600, 1580, 1480, 1460, 1415, 1310, 1300, 1260, 1205, 1180, 1155, 790, 710 |
| Formula 36b | HO, HO-phenyl coumarin with 4-F-phenyl | 6.84(1H, d), 7.10(1H, d), 7.27(2H, t), 7.76 (2H, dd), 8.12(1H, s) | 3560, 3540, 3200, 1680, 1620, 1580, 1510, 1475, 1415, 1385, 1360, 1345, 1315, 1300, 1245, 1220, 1190, 1165, 1140, 1090, 1030, 845, 830, 810, 775, 715, 695 |

TABLE 19

| Compound | Structural formula | $^1$H-NMR(DMSO-d$_6$, δ$_{ppm}$) | IR(ν$_{cm}^{-1}$) |
|---|---|---|---|
| Formula 46b | HO, HO-phenyl coumarin with 4-Br-phenyl | 6.84(1H, d), 7.11(1H, d), 7.64(2H, d), 7.69(2H, d), 8.17(1H, s) | 3550, 3380, 1715, 1610, 1595, 1515, 1495, 1475, 1410, 1345, 1315, 1295, 1240, 1220, 1210, 1125, 1080, 1030, 1010, 910, 825, 780, 770, 710 |
| Formula 47b | HO, HO-phenyl coumarin with 4-I-phenyl | 6.78(1H, s), 7.06(1H, s), 7.52(2H, d), 7.79(2H, d), 8.14(1H, s) | 3400, 1690, 1660, 1625, 1575, 1520, 1490, 1450, 1410, 1290, 1250, 1060, 1005, 980, 860, 820, 770, 730 |

TABLE 19-continued

| Compound | Structural formula | $^1$H-NMR(DMSO-d$_6$, $\delta_{ppm}$) | IR($\nu_{cm}^{-1}$) |
|---|---|---|---|
| Formula 50b | (3,4-dihydroxyphenyl structure with 4-methylphenyl) | 2.35(3H, s), 6.83(1H, d), 7.09(1H, d), 7.25(2H, d), 7.61(2H, d), 8.08(1H, s) | 3550, 3200, 1690, 1620, 1590, 1520, 1510, 1480, 1420, 1395, 1360, 1320, 1310, 1210, 1190, 1130, 1095, 1030, 1020, 830, 780, 720 |
| Formula 52b | (3,4-dihydroxyphenyl structure with 3-methylphenyl) | 2.36(3H, s), 6.83(1H, d), 7.10(1H, d), 7.19(1H, d), 7.32(1H, t), 7.49(1H, d), 7.52(1H, s), 8.09(1H, s) | 3550, 3120, 1690, 1625, 1590, 1510, 1380, 1355, 1305, 1185, 1140, 1090, 1040, 795, 710 |
| Formula 53b | (3,4-dihydroxyphenyl structure with 4-ethylphenyl) | 1.20(3H, t), 2.64(2H, q), 6.76(1H, s), 7.05(1H, s), 7.26(2H, d), 7.61(2H, d), 8.05(1H, s) | 3300, 2960, 1660, 1625, 1580, 1570, 1450, 1420, 1300, 1230, 980, 930, 860, 830, 720 |

TABLE 20

| Compound | 構造式 | $^1$H-NMR(DMSO-d$_6$, $\delta_{ppm}$) | IR($\nu_{cm}^{-1}$) |
|---|---|---|---|
| Formula 55b | (3,4-dihydroxyphenyl structure with 4-CF$_3$-phenyl) | 6.80(1H, s), 7.09(1H, s), 7.79(2H, d), 7.94(2H, d), 8.25(1H, s) | 3400, 1700, 1660, 1625, 1575, 1520, 1460, 1420, 1410, 1340, 1330, 1300, 1240, 1180, 1170, 1140, 1070, 1020, 980, 870, 860, 780, 720, 695 |
| Formula 58b | (3,4-dihydroxyphenyl structure with 4-methoxyphenyl) | 3.80(3H, s), 6.81(1H, d), 7.00(2H, d), 7.07(1H, d), 7.66(2H, d), 8.04(1H, s) | 3320, 1705, 1615, 1595, 1525, 1480, 1315, 1290, 1260, 1240, 1190, 1140, 1090, 1040, 1020, 840, 780, 700 |
| Formula 60b | (3,4-dihydroxyphenyl structure with 4-nitrophenyl) | 6.87(1H, d), 7.16(1H, d), 8.03(2H, d), 8.30(2H, d), 8.36(1H, s) | 3475, 3200, 1675, 1615, 1600, 1590, 1510, 1345, 1320, 1215, 1095, 1030, 855, 780, 710, 690 |
| Formula 61b | (3,4-dihydroxyphenyl structure with phenyl) | 6.78(1H, s), 7.07(1H, s), 7.37(1H, t), 7.43(2H, t), 7.69(2H, t), 8.09(1H, s) | 3500, 3200, 1670, 1620, 1600, 1580, 1560, 1500, 1460, 1425, 1360, 1300, 1260, 1240, 1210, 1175, 1150, 980, 960, 860, 790, 770, 720, 700 |

TABLE 20-continued

| Compound | 構造式 | $^1$H-NMR(DMSO-$d_6$, $\delta_{ppm}$) | IR($v_{cm}^{-1}$) |
|---|---|---|---|
| Formula 63b | [structure: HO, HO-substituted coumarin with thiophene] | 6.80(1H, s), 7.07(1H, s), 7.15(1H, dd), 7.59(1H, d), 7.76(1H, d), 8.42(1H, s) | 3420, 1675, 1625, 1610, 1570, 1515, 1455, 1410, 1335, 1295, 1260, 1200, 1150, 770, 700 |

TABLE 21

| Compound | Structural formula | $^1$H-NMR(DMSO-$d_6$, $\delta_{ppm}$) | IR($v_{cm}^{-1}$) |
|---|---|---|---|
| Formula 66b | [structure: dihydroxy coumarin with thiophene] | 6.85(1H, d), 7.09(1H, d), 7.63(1H, dd), 7.67(1H, dd), 8.15(1H, dd), 8.36(1H, s) | 3450, 3320, 3150, 1695, 1620, 1610, 1590, 1530, 1500, 1480, 1420, 1400, 1385, 1345, 1310, 1290, 1255, 1225, 1180, 1120, 1090, 1080, 1035, 925, 845, 815, 800, 700 |
| Formula 68b | [structure: dihydroxy coumarin with bromothiophene] | 6.87(1H, d), 7.11(1H, d), 7.71(1H, d), 7.78(1H, d), 8.57(1H, s) | 3460, 3350, 3120, 1690, 1620, 1605, 1580, 1520, 1510, 1475, 1415, 1385, 1355, 1340, 1320, 1290, 1215, 1180, 1120, 1085, 1025, 730 |
| Formula 70b | [structure: dihydroxy coumarin with bromothiophene] | 6.79(1H, s), 7.05(1H, s), 7.69(1H, d), 7.76(1H, d), 8.55(1H, s) | 3350, 3120, 1665, 1620, 1580, 1520, 1460, 1415, 1370, 1345, 1270, 1255, 1235, 1200, 970, 930, 870, 830, 750 |
| Formula 71b | [structure: dihydroxy coumarin with methylfuran] | 2.36(3H, s), 6.23(1H, d), 6.77(1H, s), 6.95(1H, d), 7.12(1H, s), 8.10(1H, s) | 3480, 3240, 1690, 1625, 1605, 1580, 1525, 1455, 1425, 1340, 1300, 1250, 1240, 1200, 1150, 1025, 920, 860, 810, 770, 720 |
| Formula 35b | [structure: dihydroxy coumarin with methyl and chlorophenyl] | 2.16(3H, s), 6.77(1H, s), 7.08(1H, s), 7.32(2H, d), 7.49(2H, d) | 3350, 1665, 1630, 1575, 1560, 1525, 1495, 1455, 1420, 1400, 1340, 1285, 1200, 1180, 1090, 1075, 1020, 980, 860, 765 |

Test Example 5

The test was performed to examine the 12-lipoxygenase and 5-lipoxygenase inhibitory activities of the compounds according to the fifth embodiment of the present invention.

1. Preparation of Samples
1) Samples

Samples were prepared in the same methods as in Examples 61–64. As controls were used known baicalein (purchased from Wako Junyaku Kogyo) represented by the following formula 20c:

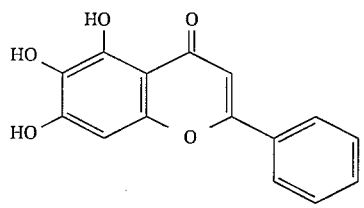

Formula 20c and known esculetin (purchased from Tokyo Kasei) represented by the following formula 21c:

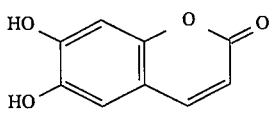

Formula 21c

2) Preparation of 12-Lipoxygenase Enzyme Solution
It was prepared in the same method as in Test Example 1.
3) Preparation of 5-Lipoxygenase Enzyme Solution
It was prepared in the same method as in Test Example 2.

2. Method of the Test

1) Method of Measurement of 12-Lipoxygenase Enzymes Activity

They were measured in the same method as in Test Example 1.

1) Method of Measurement of 5-Lipoxygenase Enzymes Activity

They were measured in the same method as in Test Example 2.

3) Measurement of Enzymes Activity

The enzymes activity of the compounds of the present invention prepared in the same methods as in Examples 61–64 and baicalein and esculetin as test compounds at varied concentrations were measured according to the above procedure and $IC_{50}$ values to 12-lipoxygenase and 5-lipoxygenase were estimated from the measured values of the test compounds.

3. Results of the Test

The results of the test are as shown in Table 22. As is apparent from Table 22, the compounds of the present invention exhibited remarkably strong inhibitory activities against 12-lipoxygenase, and $IC_{50}$ values thereof were of the order of $10^{-9}$M to the first half of $10^{-8}$, small values as compared with that of known baicalein ($4.2 \times 10^{-8}$M). On the other hand, though the compounds of the present invention exhibited inhibitory activities also against 5-lipoxygenase, $IC_{50}$ values thereof were about 7 to 20 times those against 12-lipoxygenase. Hence, it was revealed that the compounds of the present invention have selective inhibitory activities against 12-lipoxygenase.

TABLE 22

| Compound | 12-Lipoxygenase inhibiting activity $IC_{50}$ value (M) | 5-Lipoxygenase inhibiting activity $IC_{50}$ value (M) |
|---|---|---|
| Formula 22c (Example 61) | $3.4 \times 10^{-8}$ | $2.3 \times 10^{-7}$ |
| Formula 23c (Example 62) | $4.6 \times 10^{-9}$ | $6.5 \times 10^{-8}$ |
| Formula 24c (Example 63) | $1.1 \times 10^{-8}$ | $1.9 \times 10^{-7}$ |
| Formula 25c (Example 64) | $1.0 \times 10^{-8}$ | $1.8 \times 10^{-7}$ |
| Formula 20c Baicalein | $4.2 \times 10^{-8}$ | $2.4 \times 10^{-6}$ |
| Formula 21c Esculetin | $4.4 \times 10^{-6}$ | $4.3 \times 10^{-6}$ |

The measured values of nuclear magnetic resonance spectra and infrared absorption spectra of the compounds according to the fifth embodiment of the present invention were shown in Table 23. The nuclear magnetic resonance spectra [$^1$H-NMR (500 MHz)] were measured in a DMSO-$d_6$ solvent with tetramethylsilane as an internal standard and the infrared absorption spectra according to a KBr disk method respectively.

TABLE 23

| Compound | Structural formula | $^1$H-NMR(DMSO-$d_6$, $\delta_{ppm}$) | IR($v_{cm}^{-1}$) |
|---|---|---|---|
| Formula 22c | | 6.86(1H, d), 7.15(1H, d), 7.55(2H, m), 7.85(1H, dd), 7.95(2H, m), 7.97(1H, d), 8.28(1H, s), 8.31(1H, d) | 3550, 3100, 1685, 1620, 1580, 1510, 1380, 1345, 1310, 1250, 1210, 1180, 1090, 1035, 820, 750 |
| Formula 23c | | 6.81(1H, s), 7.11(1H, s), 7.54(2H, m), 7.84(1H, dd), 7.94(2H, m), 7.96(1H, d), 8.26(1H, s), 8.30(1H, d) | 3480, 1685, 1670, 1620, 1570, 1520, 1420, 1300, 1240, 1160, 750 |
| Formula 24c | | 6.85(1H, d), 7.13(1H, d), 7.42(2H, m), 7.78(1H, m), 7.94(1H, s), 8.05(1H, m), 8.13(1H, s) | 3420, 1710, 1620, 1595, 1495, 1475, 1430, 1345, 1310, 1280, 1260, 1180, 1090, 760 |

TABLE 23-continued

| Compound | Structural formula | $^1$H-NMR(DMSO-$d_6$, $\delta_{ppm}$) | IR($v_{cm}^{-1}$) |
|---|---|---|---|
| Formula 25c | (structure: 6,7-dihydroxy coumarin with benzothiophene substituent) | 6.83(1H, s), 7.09(1H, s), 7.41(2H, m), 7.77(1H, m), 7.92(1H, s), 8.05(1H, m), 8.12(1H, s) | 3500, 1660, 1620, 1580, 1425, 1270, 1215, 1180, 1155, 760 |

BEST MODE FOR CARRYING OUT THE INVENTION

Next, the present invention will be described further in detail according to Referential Examples (examples of production of intermediates for producing the compounds of the present invention), Comparative Examples (examples of production of compounds for comparison with the compounds of the present invention) and Examples; the present invention is not restricted to the following Examples.

Referential Example 1

A mixture of 1.96 g (10.0 mmol) of 2,4,5-trimethoxybenzaldehyde (purchased from Lancaster), and 1.96 g (10.0 mmol) of 4-bromophenylacetonitrile (purchased from Tokyo Kasei) in 5 ml of ethanol (purchased from Kokusan Kagaku) was heated to dissolve. Two drops of 20% aqueous sodium hydroxide solution was then added and the reaction mixture was stirred over night at ambient temperature. To the resultant reaction mass was added ethanol and crushed, and the precipitate was collected and washed with ethanol twice and with hexane twice, and dried to give 3.58 g (yield: 95.6%) of α-cyano-4-bromo-2',4',5'-trimethoxystilbene (as a yellow crystalline).

Referential Example 2

To a mixture of 771 mg (5.0 mmol) of 2,3,4-trihydroxybenzaldehyde (purchased from Aldrich) and 853 mg (5.0 mmol) of 4-chlorophenylacetic acid (purchased from Tokyo Kasei) in 10 ml of acetic anhydride (purchased from Tokyo Kasei) was added 5 ml of triethylamine (purchased from Kokusan Kagaku) under ice-cooling, and the mixture was stirred under the protection of a calcium chloride tube for 1 hour, and then refluxed in an oil bath heated at 120° C. for 4 hours. After being cooled, the resultant reaction mass was added to 100 ml of 10% ice-cooled hydrochloric acid and the mixture was stirred, and the precipitate was collected and washed with water. The obtained brown precipitate in ethanol was crushed, collected and washed with ethanol, and then recrystallized from a solution of chloroform and ethanol to give 1.17 g (yield: 62.9%) of 7,8-diacetoxy-3-(4-chlorophenyl)coumarin (as a light brown crystalline).

Referential Example 3

Synthesis of 4-iodophenylacetonitrile

A mixture of 4.36 g (20.0 mmol) of p-iodotoluene (purchased from Tokyo Kasei), 3.92 g (22.0 mmol) of N-bromosuccinimide (purchased from Tokyo Kasei) and 60 ml of carbon tetrachloride (purchased from Wako Junyaku Kogyo) was refluxed under irradiation by an incandescent lamp for 4 hours to give 2.67 g (yield: 45.0%) of 4-iodobenzyl bromide (as a white crystalline). Subsequently, to a solution of 0.49 g (10.0 mmol) of sodium cyanide (purchased from Kokusan Kagaku) in 10 ml of dimethyl sulfoxide (purchased from Aldrich) heated at 50° C. was added 1.48 g (5.0 mmol) of the above 4-iodobenzyl bromide, the mixture was stirred at ambient temperature for 3 hours, the resultant reaction mass was dissolved in water and extracted with hexane, and hexane was removed to give 0.84 g (yield: 68.9%) of 4-iodophenylacetonitrile as a white crystalline.

Referential Example 4

Synthesis of 4-ethylphenylacetonitrile

A mixture of 2.72 g (20.0 mmol) of 4-ethylbenzyl alcohol (purchased from Aldrich) and 50 ml of 47% hydrobromic acid (purchased from Wako Junyaku Kogyo) was stirred at room temperature for 30 minutes vigorously and extracted with hexane to give 3.98 g of 4-ethylbenzyl bromide as a colorless oil. Subsequently, to a solution of 1.96 g (40.0 mmol) of sodium cyanide (purchased from Kokusan Kagaku) in 20 ml of dimethyl sulfoxide (purchased from Aldrich) heated at 50° C. was added 3.98 g of the above 4-ethylbenzylbromide, the solution was stirred at ambient temperature for 3 hours, the resultant reaction mass was dissolved in water and extracted with hexane, and hexane was removed to give 2.70 g (yield: 93.1%) of 4-ethylphenylacetonitrile as a light yellow oil.

Referential Example 5

Synthesis of 4-bromothiophene-2-acetic acid

To a suspension of 1.20 g (30 mmol) of sodium hydride (60% oily, purchased from Wako Junyaku Kogyo) in 12 ml of anhydrous dioxane (purchased from Aldrich) was added a solution of 9.94 g (30.0 mmol) of tetraethyl dimethylaminomethylene diphosphonate (purchased from Lancaster) in 9 ml of anhydrous dioxane, and the mixture was stirred at room temperature for 10 minutes. Subsequently, a solution of 5.73 g (30.0 mmol) of 4-bromo-2-thiophenecarboxaldehyde (purchased from Aldrich) in 9 ml of anhydrous dioxane was added thereto and the mixture was stirred at 60° C. for 1 hour. After being cooled, the resultant mixture was poured into 100 ml of water, extracted with ether three times and dried over anhydrous sodium sulfate, and the solvent was removed to give 14.85 g of substance as a black oil.

To the oily substance was added 15 ml of concentrated hydrochloric acid and the mixture was refluxed for 15 minutes, and then the resultant mixture was poured into 100 ml of cold water and extracted with ether three times. The extract solution was subjected to reverse extraction with a 2N sodium hydroxide solution twice to adjust its pH to 1 with 6N hydrochloric acid, and then extracted with ether three times. The organic layer was washed with brine and dried over anhydrous sodium sulfate, and the solvent was removed to give a substance as a brown oil. The oily substance was purified according to chromatography on silica gel (ethyl acetate:hexane=1:1 as an eluent) to give 1.29 g (yield: 19.5%) of 4-bromothiophene-2-acetic acid as a yellowish white crystalline.

Referential Example 6

Synthesis of 5-methylfuran-2-ylacetonitrile

A mixture of 5-methylfuran-2-carboxaldehyde (5.51 g, 50 mmol, purchased from Wako Junyaku Kogyo), rhodanine (6.66 g, 50 mmol, purchased from Tokyo Kase), and anhydrous sodium acetate (12.3 g, 150 mmol, purchased from Kokusan Kagaku) in 35 ml of acetic acid (purchased from Wako Junyaku Kogyo) was refluxed for 30 minutes. After being cooled, the reaction mixture was poured into 500 ml of water. The precipitate was collected and washed with water, with ethanol, and then with ether to give 10.04 g (yield: 89.1%) of (5-methylfurylidene)rhodanine as an orange-brown color crystalline.

A suspension of the above compound in 65 ml of 15% sodium hydroxide solution was heated at 100° C. for 30 minutes. After being cooled, the reaction mixture was poured into 500 ml of 10% hydrochloric acid. The precipitate was collected and washed with water to give 8.22 g of 3-(5-methylfuryl)-2-thioketopropionic acid as a yellow crystalline.

To a mixture of 8.22 g of the above compound, 45 ml of ethanol, and hydroxylamine hydrochloride (10.1 g, 146 mmol, purchased from Wako Junyaku Kogyo) was added 55 ml of sodium ethoxide-21% denatured alcohol solution (147 mmol equivalent, purchased from Aldrich) gradually and heated at 100° C. After being cooled, the mixture was concentrated under reduced pressure. To the residue was added 20 ml of 5% sodium hydroxide solution and then was added 20 ml of 10% hydrochloric acid carefully under ice-cooling. The mixture was extracted with ether three times and the combined organic layer was washed with brine, and dried over anhydrous sodium sulfate. The solvent was removed. The residue was dissolved in a small amount of ether and then toluene was added to the solution till the mixture became slightly cloudy and the mixture was allowed to stand. The precipitate was collected and washed with toluene to give 4.55 g (yield: 53.3%) of 3-(5-methyl-2-furyl)-2-hydroxyiminopropionic acid as a yellow crystalline.

To a solution of 4.55 g of the above compound in 60 ml of benzene was added 1,1'-carbonyldiimidazole (3.97 g, 24.8 mmol, purchased from Aldrich) gradually and the mixture was heated at 70° C. for 1 hour. After being cooled, the mixture was poured into 50 ml of ice-water, and extracted with benzene three times. The combined organic layer was washed with aqueous sodium bicarbonate, with brine, with 1% hydrochloric acid, and then with water in order and dried over anhydrous sodium sulfate. The solvent was removed under reduced pressure. The residual oil (2.4 g) was purified on silica gel chromatography (ethyl acetate-:hexane=1:4 as an eluent) to give 2.00 g (yield: 66.6%) of 5-methylfuran-2-ylacetonitrile as a colorless oil.

Comparative Example 1

To a mixture of 150 mg (0.59 mmol) of a compound represented by the formula 52 obtained in the same method as in Example 17 and 3 ml of acetone (purchased from Kanto Kagaku) was added 207 mg (1.5 mmol) of anhydrous potassium carbonate crushed, and then 0.14 ml (1.5 mmol) of dimethyl sulfate (purchased from Tokyo Kasei) was further added thereto, and the reaction solution was refluxed under atmosphere of nitrogen gas for 2 hours. After being cooled, the resultant mixture was added to 20 ml of diluted hydrochloric acid ice-cooled, and the precipitate was collected and washed with water and with a small amount of ethanol, and dried to give 130 mg (yield: 78.1%) of the compound as a white crystalline represented by the following formula:

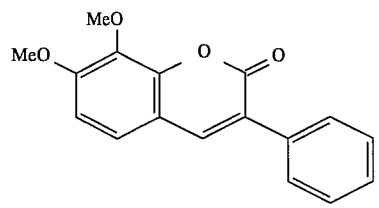

Formula 31 melting point of the obtained compound was 147°–148° C.

Comparative Example 2

7-acetoxy-3-(4-chlorophenyl)coumarin as a white crystalline, 988 mg (yield:62.8%), was obtained in the same method as in Referential Example 2 except that 691 mg (5.0 mmol) of 2,4-dihydroxybenzaldehyde (purchased from Tokyo Kasei) was used instead of 2,3,4-trihydroxybenzaldehyde, and 236 mg (yield: 86.5%) of the compound as a light yellow crystalline represented by the following formula was obtained in the same method as in Example 2 except that 314 mg (1.0 mmol) of the above 7-acetoxy-3-(4-chlorophenyl)coumarin was used instead of 7,8-diacetoxy-3-(4-fluorophenyl)coumarin:

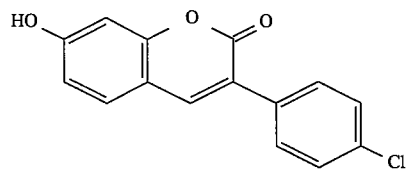

Formula 32 melting point of the obtained compound was 296°–297° C.

Comparative Example 3

A mixture of 1.26 g (10.0 mmol) of pyrogallol (purchased from Tokyo Kasei), 1.92 g (10.0 mmol) of ethyl benzoylacetate (purchased from Tokyo Kasei) and 10 ml of 75% sulfuric acid was stirred in an oil bath heated at 55° C. over night. After being cooled, 15 ml of ice water were added to the reaction mixture and the mixture was stirred, and the resultant reaction mass was crushed, and the precipitate was collected and washed with water. The precipitate as a yellowish brown powder was dissolved in ethyl acetate and dried over anhydrous sodium sulfate. Activated carbon was added to the filtrate, and the filtrate was heated and concentrated under reduced pressure. The residue was dissolved in ethyl acetate under heating, hexane was added thereto, and the mixture was stirred at ambient temperature. The precipitate was collected and dried to give 916 mg (yield: 36%) of the compound as a brown crystalline represented by the following formula:

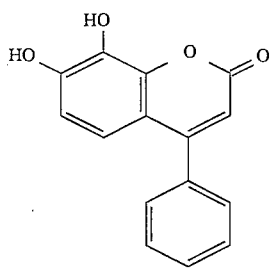

Formula 33 melting point of the obtained compound was 191.5°–192.5° C.

Comparative Example 4

To a solution of 821 mg (5.0 mmol) of ethyl phenylacetate (purchased from Tokyo Kasei) in 2 ml of ethanol (purchased from Kokusan Kagaku) was added a solution of 0.8 g of sodium hydroxide dissolved in 2 ml of water, and the mixture was stirred at room temperature for 2 hours. To the mixture was added 30 ml of about 10% hydrochloric acid, the mixture was extracted with ether three times, the organic layer was washed with brine and dried over anhydrous sodium sulfate, and the solvent was removed under reduced pressure. To the residue were added 1.15 g (5.0 mmol) of 2,3,4-trihydroxybenzophenone (purchased from Tokyo Kasei) and 10 ml of acetic anhydride (purchased from Wako Junyaku), and then 5 ml of triethylamine (purchased from Kokusan Kagaku) was added to the mixture under stirring and ice-cooling, and the mixture was stirred for 1 hour. Subsequently, the resultant mixture was refluxed for 2 hours in an oil bath heated at 120° C. After being cooled, the resultant mixture was added to 100 ml of 10% hydrochloric acid ice-cooled, stirred for a while and extracted with methylene chloride three times. The organic layer was washed with aqueous sodium hydrogencarbonate and subsequently with brine and dried over anhydrous sodium sulfate, and the solvent was removed under reduced pressure. The residue as an oil was purified by column chromatography on silica gel (ethyl acetate:hexane=1:2 as an eluent) to give 823 mg (yield: 39.8%) of 7,8-diacetoxy-3,4-diphenylcoumarin as a white crystalline. To 250 mg (0.6 mmol) of the above 7,8-diacetoxy-3,4-diphenylcoumarin were added 8 ml of ethanol, 1 ml of water and 1 ml of concentrated hydrochloric acid, and the mixture was refluxed for 4 hours. After being cooled, the resultant mixture was added to 60 ml of water, and the precipitate was collected, washed with water and dried to give 165 mg (yield: 82.8%) of the compound as a white crystalline represented by the following formula:

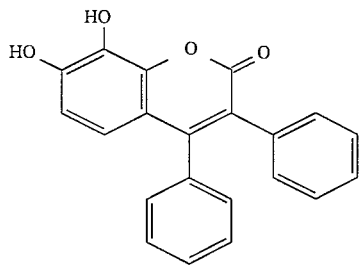

Formula 34 melting point of the obtained compound was 281°–282° C.

Comparative Example 5

7,8-diacetoxy-3-(4-acetoxyphenyl)coumarin as a semiopaque crystalline, 1.45 g (yield: 73.0%), was obtained in the same method as in Referential Example 2 except that 761 mg (5.0 mmol) of 4-hydroxyphenyl acetate (purchased from Tokyo Kasei) was used instead of 4-chlorophenylacetate, and 189 mg (yield: 70.0%) of the compound as an ocherous crystalline represented by the following formula was obtained in the same method as in Example 2 except that 396 mg (1.0 mmol) of the above 7,8-diacetoxty-3-(4-acetoxyphenyl)coumarin was used instead of 7,8-diacetoxy-3-(4-fluorophenyl)coumarin:

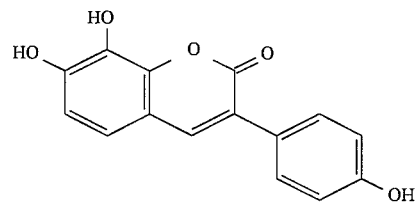

Formula 35 melting point of the obtained compound was 295° C. (decomposed).

EXAMPLE 1

A mixture of 748 mg (2.0 mmol) of α-cyano-4-bromo-2',4',5'-trimethoxystilbene obtained in the same method as in Referential Example 1 and 3.47 g (30.0 mmol) of pyridinium chloride (purchased from Aldrich) was melted to mix on an oil bath heated at 210° C. under atmosphere of argon gas and stirred at the same temperature for 1 hour. After being cooled, 20 ml of 2N hydrochloric acid was added to the resultant reaction mass, and then was crushed and stirred for 30 minutes. The precipitate was collected, and washed with water three times and dried, and then purified by column chromatography on silica gel (using ethyl acetate as an eluent) to give 551 mg (yield: 82.7%) of the compound as a yellow crystalline represented by the following formula:

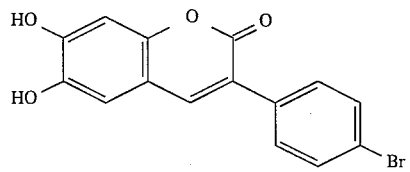

Formula 36 melting point of the obtained compound was 287°–288° C.

EXAMPLE 2

To a mixture of 356 mg (1.0 mmol) of 7,8-diacetoxy-3-(4-fluorophenyl)coumarin obtained in the same method as in Referential Example 2 except that 771 mg (5.0 mmol) of 4-fluorophenylacetic acid (purchased from Lancaster) was used instead of 4-chlorophenylacetic acid in 8 ml of ethanol (purchased from Kokusan Kagaku) was added 2 ml of 6N hydrochloric acid, and the mixture was refluxed for 1 hour. After being cooled, the resultant product was added to 60 ml of water, the mixture was stirred, and the precipitate was collected and washed with water. After drying, the residue was recrystallized from ethyl acetate and hexane to give 193 mg (yield: 70.9%) of the compound as a light yellow crystalline represented by the following formula:

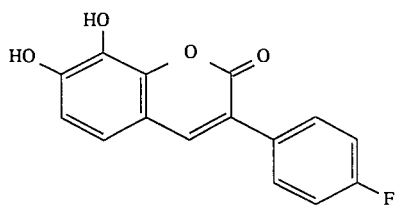

Formula 37 melting point of the obtained compound was 248°–249° C.

EXAMPLE 3

7,8-diacetoxy-3-(3-methylphenyl)coumarin, 352 mg (1.0 mmol), obtained in the same method as in Referential Example 2 except that 751 mg (5.0 mmol) of 3-methylphenylacetic acid (purchased from Tokyo Kasei) was used instead of 4-chlorophenylacetic acid was suspended into 8 ml of ethanol (purchased from Kokusan Kagaku), and a solution of 168 mg (4.0 mmol) of lithium hydroxide monohydrate in 4 ml of water was added to the suspension, and the mixture was stirred at room temperature for 1 hour. Subsequently, the mixture was acidified with 4 ml of about 10% hydrochloric acid, and concentrated and dried under reduced pressure. Ethyl acetate and water were added to the residue, and the organic layer was separated and washed with brined and dried over anhydrous sodium sulfate. The filtrate from which sodium sulfate was separated was purified by column chromatography on silica gel (using ethyl acetate as an eluent) to give 203 mg (yield: 75.7%) of the compound as a yellow crystalline represented by the following formula:

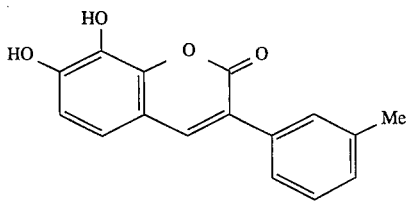

Formula 38 melting point of the obtained compound was 185.5°–186.5° C.

EXAMPLE 4

To a mixture of 771 mg (5.0 mmol) of 2,3,4-trihydroxybenzaldehyde (purchased from Aldrich) and 758 mg (5.0 mmol) of 4-chlorophenylacetonitrile (purchased from Tokyo Kasei) in 10 ml of ethanol was added 0.54 ml of piperidine (purchased from Wako Junyaku), and the mixture was refluxed for 6 hours. After being cooled, the reaction mixture was added to 100 ml of 1N hydrochloric acid and stirred, and the precipitate was collected and washed with water. The precipitate was dissolved in ethyl acetate, washed with 20% aqueous sodium bisulfite solution twice and with brine once, and dried over anhydrous sodium sulfate, and the solvent was removed to give about 300 mg of substance as a black brown solid. The substance was purified by column chromatography on silica gel (ethyl acetate:hexane=1:5~3:5 as an eluent) to give 227 mg (yield: 15.7%) of the compound as a light yellow crystalline represented by the following formula:

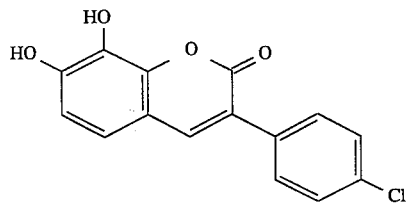

Formula 39 melting point of the obtained compound was 239°–241° C.

EXAMPLE 5

To a mixed solution of 25 ml of concentrated hydrochloric acid and 15 g of ice was added 3.83 g (30.0 mmol) of p-chloroaniline (purchased from Tokyo Kasei), and then 7 ml of 30% aqueous sodium nitrite (purchased from Wako Junyaku) solution was added, and the mixture was stirred at room temperature for 1 hour. An aqueous saturated sodium acetate (purchased from Wako Junyaku) solution was added to the mixture to adjust its pH to 4, and insoluble materials were filtrated. The filtrate was added to a suspension of 5.77 g (30 mmol) of 4-methylesculetin (purchased from Tokyo Kasei) in 90 ml of acetone, and 0.8 g of cupric chloride dihydrate (purchased from Kanto Kagaku) was further added thereto, and the mixture was stirred for 1 hour. The resultant mixture was concentrated under reduced pressure to remove most of the solvent, and 300 ml of ethyl acetate were added to the residue and mixed. After insoluble material (unreacted 4-methylesculetin) was filtrated, an organic layer was separated from the filtrate, the water layer was further extracted with ethyl acetate twice, and the combined organic layer was washed with brine and dried over anhydrous magnesium sulfate. The solvent was removed under reduced pressure, and the residue was purified by column chromatography on silica gel (ethyl acetate:hexane=1:1 as an eluent) to give 533 mg (yield: 5.9%) of the compound as a light yellow crystalline represented by the following formula:

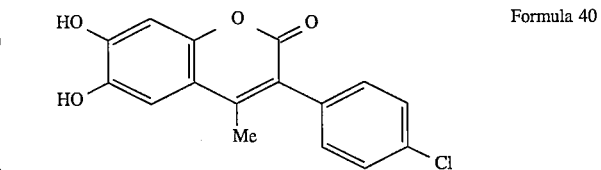

Formula 40 melting point of the obtained compound was 174°–175° C.

EXAMPLE 6

α-cyano-2',4',5'-trimethoxystilbene was obtained in the same method as in Referential Example 1 except that 586 mg (5.0 mmol) of phenylacetonitrile (purchased from Tokyo Kasei) was used instead of 4-bromophenylacetonitrile, and 444 mg (yield: 87.3%) of the compound as a yellowish brown crystalline represented by the following formula was obtained in the same method as in Example 1 except that 591 mg (2.0 mmol) of the above α-cyano-2',4',5'-trimethoxystilbene was used instead of α-cyano-4-bromo-2',4',5'-trimethoxystilbene:

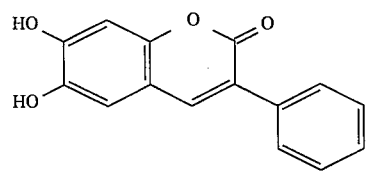

Formula 41 melting point of the obtained compound was 251°–253° C.

EXAMPLE 7

α-cyano-4-fluoro-2',4',5'-trimethoxystilbene was obtained in the same method as in Referential Example 1 except that 1.35 g (10.0 mmol) of 4-fluorophenylacetonitrile (purchased from Tokyo Kasei) was used instead of 4-bromophenylacetonitrile, and 364 mg (yield: 66.9%) of the compound as a yellowish brown crystalline represented by the following formula was obtained in the same method as in Example 1 except that 599 mg (2.0 mmol) of the above α-cyano-4-fluoro-2',4',5'-trimethoxystilbene was used instead of α-cyano-4-bromo-2',4',5'-trimethoxystilbene:

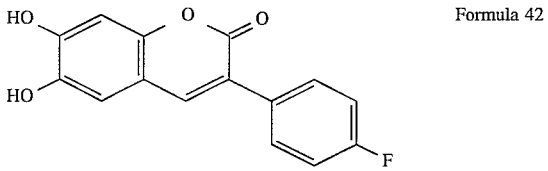

Formula 42 melting point of the obtained compound was 287°–288° C.

EXAMPLE 8

α-cyano-4-chloro-2',4',5'-trimethoxystilbene was obtained in the same method as in Referential Example 1 except that 1.52 g (10.0 mmol) of 4-chlorophenylacetonitrile (purchased from Tokyo Kasei) was used instead of 4-bromophenylacetonitrile, and 435 mg (yield: 75.3%) of the compound as a yellow crystalline represented by the following formula was obtained in the same method as in Example 1 except that 660 mg (2.0 mmol) of the above α-cyano-4-chloro-2',4',5'-trimethoxystilbene was used instead of α-cyano-4-bromo-2',4',5'-trimethoxystilbene:

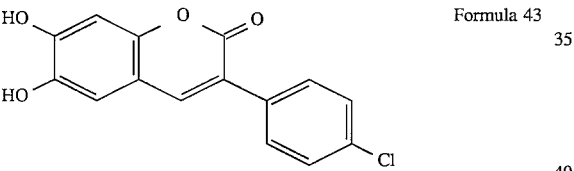

Formula 43 melting point of the obtained compound was 289°–291° C.

EXAMPLE 9

α-cyano-3-chloro-2',4',5'-trimethoxystilbene was obtained in the same method as in Referential Example 1 except that 1.52 g (10.0 mmol) of 3-chlorophenylacetonitrile (purchased from Tokyo Kasei) was used instead of 4-bromophenylacetonitrile, and 290 mg (yield: 50.2%) of the compound as a light yellow crystalline represented by the following formula was obtained in the same method as in Example 1 except that 660 mg (2.0 mmol) of the above a-cyano-3-chloro-2',4',5'-trimethoxystilbene was used instead of α-cyano-4-bromo-2',4',5'-trimethoxystilbene:

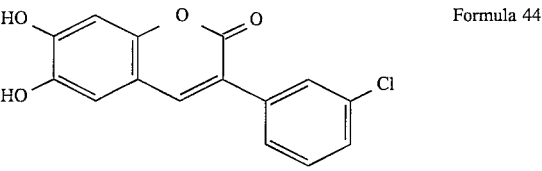

Formula 44 melting point of the obtained compound was 279°–281° C.

EXAMPLE 10

α-cyano-4-iodo-2',4',5'-trimethoxystilbene was obtained in the same method as in Referential Example 1 except that 392 mg (2.0 mmol) of 2,4,5-trimethoxybenzaldehyde (purchased from Lancaster) and 486 mg (2.0 mmol) of 4-iodophenylacetonitrile instead of 4-bromophenylacetonitrile were used. 4-iodophenylacetonitrile was obtained in the same method described in Referential Example 3. And 566 mg (yield: 74.4%) of the compound as a yellow crystalline represented by the following formula was obtained in the same method as in Example 1 except that 421 mg (1.0 mmol) of the above α-cyano-4-iodo-2',4',5'-trimethoxystilbene was used instead of α-cyano-4-bromo-2',4',5'-trimethoxystilbene:

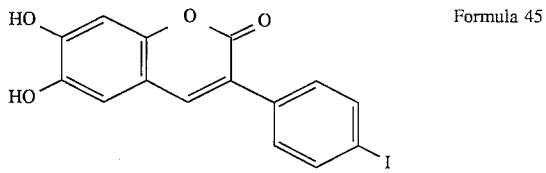

Formula 45 melting point of the obtained compound was 273°–276° C.

EXAMPLE 11

α-cyano-4-methyl-2',4',5'-trimethoxystilbene was obtained in the same method as in Referential Example 1 except that 1.31 g (10.0 mmol) of 4-methylphenylacetonitrile (purchased from Tokyo Kasei) was used instead of 4-bromophenylacetonitrile, and 435 mg (yield: 81.0%) of the compound as a yellow crystalline represented by the following formula was obtained in the same method as in Example 1 except that 619 mg (2.0 mmol) of the above α-cyano-4-methyl-2',4',5'-trimethoxystilbene was used instead of α-cyano-4-bromo-2',4',5'-trimethoxystilbene:

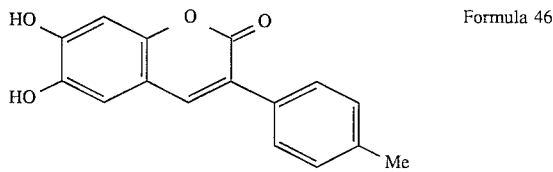

Formula 46 melting point of the obtained compound was 252.5°–253° C.

EXAMPLE 12

α-cyano-3-methyl-2',4',5'-trimethoxystilbene was obtained in the same method as in Referential Example 1 except that 1.31 g (10.0 mmol) of 3-methylphenylacetonitrile (purchased from Aldrich) was used instead of 4-bromophenylacetonitrile, and 493 mg (yield: 91.8%) of the compound as a yellow crystalline represented by the following formula was obtained in the same method as in Example 1 except that 619 mg (2.0 mmol) of the above α-cyano-3-methyl-2',4',5'-trimethoxystilbene was used instead of α-cyano-4-bromo-2',4',5'-trimethoxystilbene:

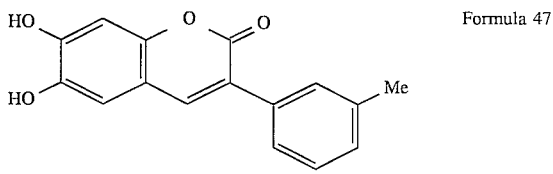

Formula 47 melting point of the obtained compound was 216°–218° C.

EXAMPLE 13

α-cyano-4-ethyl-2',4',5'-trimethoxystilbene was obtained in the same method as in Referential Example 1 except that 628 mg (3.20 mmol) of 2,4,5-trimethoxybenzaldehyde (purchased from Lancaster) and 465 mg (3.20 mmol) of 4-ethylphenylacetonitrile instead of 4-bromophenylacetonitrile were used. 4-ethylphenylacetonitrile was obtained in the same method described in Referential Example 4. And 493 mg (yield: 87.5%) of the compound as a yellow crystalline represented by the following formula was obtained in the same method as in Example 1 except that 485 mg (1.5 mmol) of the above α-cyano-4-bromo-2',4',5'-trimethoxystilbene was used instead of α-cyano-4-bromo-2',4',5'-trimethoxystilbene:

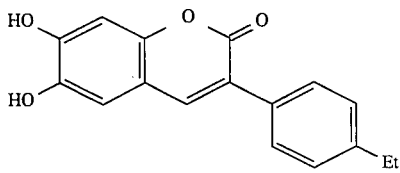

Formula 48 melting point of the obtained compound was 232°–234° C.

EXAMPLE 14

α-cyano-4-trifluoromethyl-2',4',5'-trimethoxystilbene was obtained in the same method as in Referential Example 1 except that 1.85 g (10.0 mmol) of 4-trifluoromethylphenylacetonitrile (purchased from Aldrich) was used instead of 4-bromophenylacetonitrile, and 594 mg (yield: 92.2%) of the compound as a light yellow crystalline represented by the following formula was obtained in the same method as in Example 1 except that 727 mg (2.0 mmol) of the above α-cyano-4-trifluoromethyl-2',4',5'-trimethoxystilbene was used instead of α-cyano-4-bromo-2',4',5'-trimethoxystilbene:

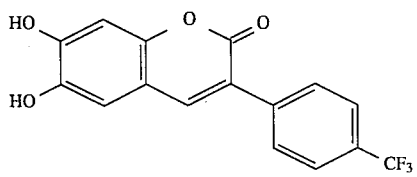

Formula 49 melting point of the obtained compound was 257°–258° C.

EXAMPLE 15

α-(2,4,5-trimethoxybenzylidene)thiophene-2-acetonitrile was obtained in the same method as in Referential Example 1 except that 1.23 g (10.0 mmol) of thiophen-2-ylacetonitrile (purchased from Tokyo Kasei) was used instead of 4-bromophenylacetonitrile, and 274 mg (yield: 52.6%) of the compound as a yellow crystalline represented by the following formula was obtained in the same method as in Example 1 except that 603 mg (2.0 mmol) of the above α-(2,4,5-trimethoxybenzylidene)thiophene-2-acetonitrile was used instead of α-cyano-4-bromo-2',4',5'-trimethoxystilbene:

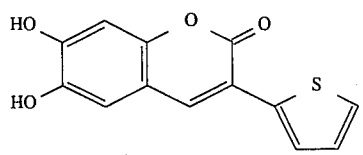

Formula 50 melting point of the obtained compound was 273° C. (decomposed).

EXAMPLE 16

α-(2,4,5-trimethoxybenzylidene)thiophene-3-acetonitrile was obtained in the same method as in Referential Example 1 except that 1.23 g (10.0 mmol) of thiophen-3-ylacetonitrile (purchased from Tokyo Kasei) was used instead of 4-bromophenylacetonitrile, and 315 mg (yield: 60.5%) of the compound as a yellow crystalline represented by the following formula was obtained in the same method as in Example 1 except that 603 mg (2.0 mmol) of the above α-(2,4,5-trimethoxybenzylidene)thiophene-3-acetonitrile was used instead of α-cyano-4-bromo-2',4',5'-trimethoxystilbene:

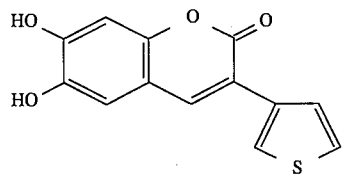

Formula 51 melting point of the obtained compound was 249°–250° C.

EXAMPLE 17

α-cyano-2',3',4'-trimethoxystilbene was obtained in the same method as in Referential Example 1 except that 1.96 g (10.0 mmol) of 2,3,4-trimethoxybenzaldehyde (purchased from Tokyo Kasei) was used instead of 2,4,5-trimethoxybenzaldehyde and that 1.17 g (10.0 mmol) of phenylacetonitrile was used instead of 4-bromophenylacetonitrile, and 474 mg (yield: 93.2%) of the compound as a yellow crystalline represented by the following formula was obtained in the same method as in Example 1 except that 591 mg (2.0 mmol) of the above α-cyano-2',3',4'-trimethoxystilbene was used instead of α-cyano-4-bromo-2',4',5'-trimethoxystilbene:

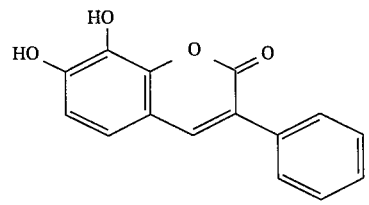

Formula 52 melting point of the obtained compound was 209°–210° C.

EXAMPLE 18

α-cyano-4-methyl-2',3',4'-trimethoxystilbene was obtained in the same method as in Referential Example 1 except that 1.96 g (10.0 mmol) of 2,3,4-trimethoxybenzaldehyde (purchased from Tokyo Kasei) was used instead of 2,4,5-trimethoxybenzaldehyde and that 1.31 g (10.0 mmol) of 4-methylphenylacetonitrile was used instead of 4-bromophenylacetonitrile, and 481 mg (yield: 89.7%) of the compound as a yellow crystalline represented by the following formula was obtained in the same method as in Example 1 except that 619 mg (2.0 mmol) of the above α-cyano-4-methyl-2',3',4'-trimethoxystilbene was used instead of α-cyano-4-bromo-2',4',5'-trimethoxystilbene:

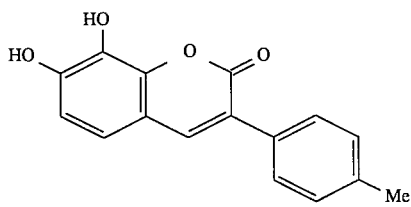

Formula 53 melting point of the obtained compound was 226°–227° C.

EXAMPLE 19

α-cyano-4-ethyl-2',3',4'-trimethoxystilbene was obtained in the same method as in Referential Example 1 except that 1.96 g (10.0 mmol) of 2,3,4-trimethoxybenzaldehyde (purchased from Tokyo Kasei) was used instead of 2,4,5-trimethoxybenzaldehyde and that 1.45 g (10.0 mmol) of 4-ethylphenylacetonitrile obtained in the method according to Referential Example 4 was used instead of 4-bromophenylacetonitrile, and 436 mg (yield: 77.2%) of the compound as a yellow crystalline represented by the following formula were obtained in the same method as in Example 1 except that 647 mg (2.0 mmol) of the above α-cyano-4-ethyl-2',3',4'-trimethoxystilbene was used instead of α-cyano-4-bromo-2',4',5'-trimethoxystilbene:

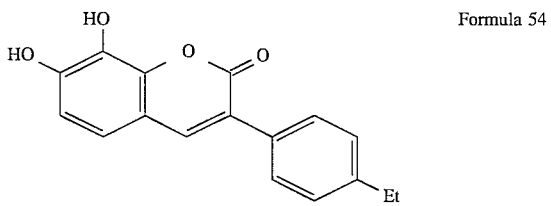

Formula 54 melting point of the obtained compound was 188.5°–190° C.

EXAMPLE 20

α-cyano-4-trifluoromethyl-2',3',4'-trimethoxystilbene was obtained in the same method as in Referential Example 1 except that 1.96 g (10.0 mmol) of 2,3,4-trimethoxybenzaldehyde (purchased from Tokyo Kasei) was used instead of 2,4,5-trimethoxybenzaldehyde and that 1.85 g (10.0 mmol) of 4-trifluoromethylphenylacetonitrile was used instead of 4-bromophenylacetonitrile, and 205 mg (yield: 31.8%) of the compound as a yellow crystalline represented by the following formula was obtained in the same method as in Example 1 except that 727 mg (2.0 mmol) of the above α-cyano-4-trifluoromethyl-2',3',4'-trimethoxystilbene was used instead of α-cyano-4-bromo-2',4',5'-trimethoxy stilbene:

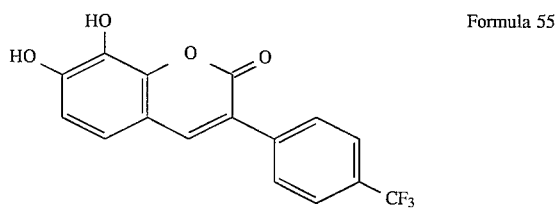

Formula 55 melting point of the obtained compound was 234°–234.5° C.

EXAMPLE 21

α-(2,3,4-trimethoxybenzylidene)thiophene-3-acetonitrile was obtained in the same method as in Referential Example 1 except that 1.96 g (10.0 mmol) of 2,3,4-trimethoxybenzaldehyde (purchased from Tokyo Kasei) was used instead of 2,4,5-trimethoxybenzaldehyde and that 1.23 g (10.0 mmol) of thiophen-3-ylacetonitrile (purchased from Tokyo Kasei) was used instead of 4-bromophenylacetonitrile, and 376 mg (yield: 72.3%) of the compound as a yellow crystalline represented by the following formula was obtained in the same method as in Example 1 except that 603 mg (2.0 mmol) of the above α-(2,3,4-trimethoxybenzylidene)thiophene-3-acetonitrile was used instead of α-cyano-4-bromo-2',4',5'-trimethoxystilbene:

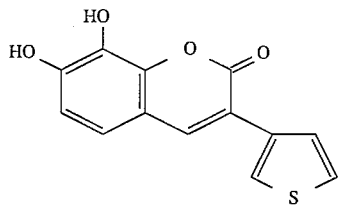

Formula 56 melting point of the obtained compound was 243°–245.5° C.

EXAMPLE 22

7,8-diacetoxy-3-(3-chlorophenyl)coumarin was obtained in the same method as in Referential Example 2 except that 853 mg (5.0 mmol) of 3-chlorophenylacetic acid (purchased from Tokyo Kasei) was used instead of 4-chlorophenylacetic acid, and 268 mg (yield: 92.8%) of the compound as a light yellow crystalline represented by the following formula was obtained in the same method as in Example 2 except that 373 mg (1.0 mmol) of the above 7,8-diacetoxy-3-(3-chlorophenyl)coumarin was used instead of 7,8-diacetoxy-3-(4-fluorophenyl)coumarin:

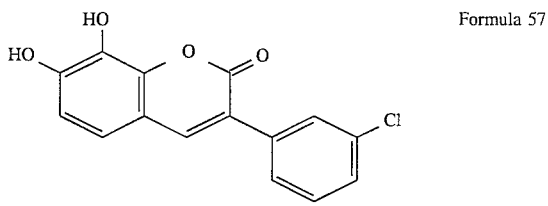

Formula 57 melting point of the obtained compound was 281°–282° C.

EXAMPLE 23

7,8-diacetoxy-3-(4-nitrophenyl)coumarin was obtained in the same method as in Referential Example 2 except that 906 mg (5.0 mmol) of 4-nitrophenylacetic acid (purchased from Tokyo Kasei) was used instead of 4-chlorophenylacetic acid, and 228 mg (yield: 76.2%) of the compound as an orange crystalline represented by the following formula was obtained in the same method as in Example 2 except that 383 mg (1.0 mmol) of the above 7,8-diacetoxy-3-(4-nitrophenyl)coumarin was used instead of 7,8-diacetoxy-3-(4-fluorophenyl)coumarin:

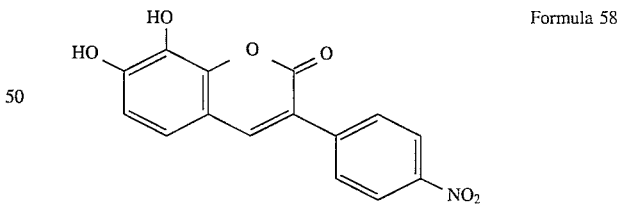

Formula 58 melting point of the obtained compound was 303°–304° C. (decomposed).

EXAMPLE 24

7,8-diacetoxy-3-(4-chlorophenyl)coumarin was obtained in the same method as in Referential Example 2, and 242 mg (yield: 83.9%) of the compound as a yellow crystalline represented by the following formula was obtained in the same method as in Example 2 except that 373 mg (1.0 mmol) of the above 7,8-diacetoxy-3-(4chlorophenyl)coumarin was used instead of 7,8-diacetoxy-3-(4-fluorophenyl) coumarin:

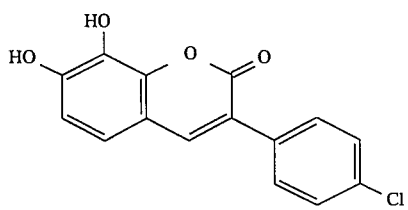

melting point of the obtained compound was 240°–241° C.
NMR and IR spectra were identical with those of the compounds obtained in Example 4.

EXAMPLE 25

7,8-diacetoxy-3-(4-bromophenyl)coumarin was obtained in the same method as in Referential Example 2 except that 1075 mg (5.0 mmol) of 4-bromophenylacetic acid (purchased from Tokyo Kasei) was used instead of 4-chlorophenylacetic acid, and 300 mg (yield: 90.2%) of the compound as a yellow crystalline represented by the following formula was obtained in the same method as in Example 2 except that 417 mg (1.0 mmol) of the above 7,8-diacetoxy-3-(4-bromophenyl)coumarin was used instead of 7,8-diacetoxy-3-(4-fluorophenyl)coumarin:

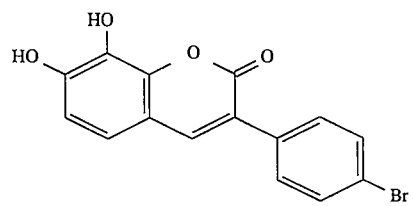

melting point of the obtained compound was 262°–264° C.

EXAMPLE 26

7,8-diacetoxy-3-(4-methylphenyl)coumarin was obtained in the same method as in Referential Example 2 except that 751 mg (5.0 mmol) of 4-methylphenylacetic acid (purchased from Tokyo Kasei) was used instead of 4-chlorophenylacetic acid, and 233 mg (yield: 86.9%) of the compound as a yellow crystalline represented by the following formula was obtained in the same method as in Example 2 except that 352 mg (1.0 mmol) of the above 7,8-diacetoxy-3-(4-methylphenyl)coumarin was used instead of 7,8-diacetoxy-3-(4-fluorophenyl)coumarin:

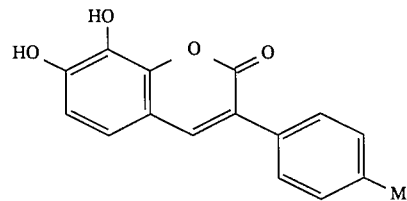

melting point of the obtained compound was 226°–227° C.
NMR and IR spectra were identical with those obtained in Example 18.

EXAMPLE 27

7,8-diacetoxy-3-(4-methoxyphenyl)coumarin was obtained in the same method as in Referential Example 2 except that 831 mg (5.0 mmol) of 4-methoxyphenylacetic acid (purchased from Tokyo Kasei) was used instead of 4-chlorophenylacetic acid, and 186 mg (yield: 65.5%) of the compound as an ocherous crystalline represented by the following formula was obtained in the same method as in Example 2 except that 368 mg (1.0 mmol) of the above 7,8-diacetoxy-3-(4-methoxyphenyl)coumarin was used instead of 7,8-diacetoxy-3-(4-fluorophenyl)coumarin:

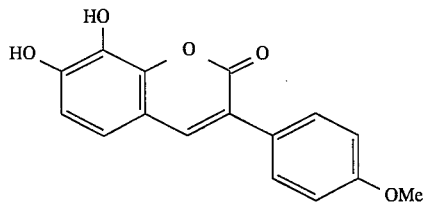

melting point of the obtained compound was 245°–246° C.

EXAMPLE 28

6,7-diacetoxy-3-(4-chlorophenyl)coumarin was obtained in the same method as in Referential Example 2 except that 771 mg (5.0 mmol) of 2,4,5-trihydroxybenzaldehyde (purchased from Lancaster) was used instead of 2,3,4-trihydroxybenzaldehyde, and 176 mg (yield: 60.9%) of the compound as a yellow crystalline represented by the following formula was obtained in the same method as in Example 3 except that 373 mg (1.0 mmol) of the above 6,7-diacetoxy-3-(4-chlorophenyl)coumarin was used instead of 7,8-diacetoxy-3-(3methylphenyl)coumarin:

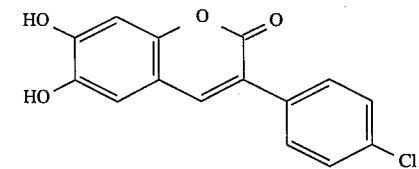

melting point of the obtained compound was 290°–291° C.
NMR and IR spectra were identical with those obtained in Example 8.

EXAMPLE 29

The compound as a yellow crystalline, 264 mg (yield: 20.3%), represented by the following formula was obtained in the same method as in Example 4 except that 616 mg (5.0 mmol) of thiophen-2-ylacetonitrile (purchased from Tokyo Kasei) was used instead of 4-chlorophenylacetonitrile:

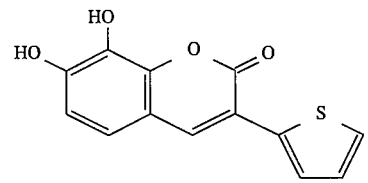

melting point of the obtained compound was 246°–247° C.

EXAMPLE 30

The compound as a yellow crystalline, 153 mg (yield: 1.9%), represented by the following formula was obtained in the same method as in Example 5 except that 3.89 g (30.0 mmol) of aniline hydrochloride (purchased from Wako Junyaku) was used instead of p-chloroaniline:

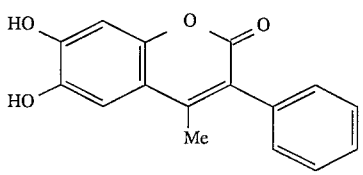

Formula 65 melting point of the obtained compound was 161°–162° C.

EXAMPLE 31

A mixture having the following composition per a tablet was prepared and tableted by a tableting machine according to an ordinary procedure to give a medicine of the present invention inhibiting 12-lipoxygenase selectively.

| Compound obtained in Example 1 | 30.0 (mg) |
|---|---|
| Lactose (purchased from Iwaki Seiyaku) | 40.0 |
| Cornstarch (purchased from Yoshida Seiyaku) | 15.0 |
| Magnesium stearate (purchased from Taihei Kagaku) | 0.4 |
| Carboxymethylcellulose calcium (purchased from Nichirin Kagaku Kogyo) | 20.0 |

EXAMPLE 32

A mixture having the following composition per a capsule was prepared and filled into a gelatin capsule according to an ordinary procedure to give a medicine of the present invention inhibiting 12-lipoxygenase selectively.

| Compound obtained in Example 5 | 30.0 (mg) |
|---|---|
| Lactose (purchased from Iwaki Seiyaku) | 40.0 |
| Fine powdered cellulose (purchased from Nippon Soda) | 30.0 |
| Magnesium stearate (purchased from Taihei Kagaku) | 3.0 |

EXAMPLE 33

7,8-diacetoxy-3-(4-bromothiophen-2-yl)coumarin as a light brown crystalline, 756 mg (yield: 71.4%), was obtained in the same method as in Referential Example 2 except that 385 mg (2.5 mmol) of 2,3,4-trihydroxybenzaldehyde (purchased from Aldrich) was used and that 553 mg (2.5 mmol) of 4-bromothiophene-2-acetic acid was used instead of 4-chlorophenylacetic acid.

The compound as a yellow crystalline, 310 mg (yield: 91.4%), represented by the following formula was obtained in the same method as in Example 2 except that 423 mg (1.0 mmol) of the above 7,8-diacetoxy-3-(4-bromothiophen-2-yl)coumarin was used instead of 7,8-diacetoxy-3-(4-fluorophenyl)coumarin:

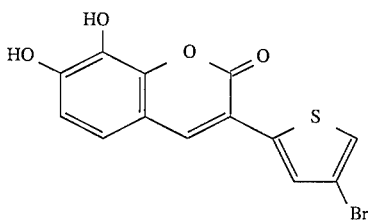

Formula 66 melting point of the obtained compound was 291° C. (decomposed).

EXAMPLE 34

6,7-diacetoxy-3-(4-bromothiophen-2-yl)coumarin as a light brown crystalline, 755 mg (yield: 71.4%), was obtained in the same method as in Referential Example 2 except that 385 mg (2.5 mmol) of 2,4,5-trihydroxybenzaldehyde (purchased from Lancaster) was used and that 553 mg (2.5 mmol) of 4-bromothiophene-2-acetic acid was used instead of 4-chlorophenylacetic acid.

The compound as a yellow crystalline, 287 mg (yield: 84.6%), represented by the following formula was obtained in the same method as in Example 2 except that 423 mg (1.0 mmol) of the above 6,7-diacetoxy-3-(4-bromothiophen-2-yl)coumarin was used instead of 7,8-diacetoxy-3-(4-fluorophenyl)coumarin:

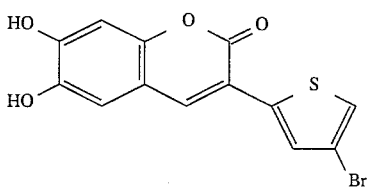

Formula 67 melting point of the obtained compound was more than 300° C.

EXAMPLE 35

5-methyl-α-(2,3,4-trimethoxybenzylidene)furan-2-acetonitrile as a green crystalline, 703 mg (yield: 47.1%), was obtained in the same method as in Referential Example 1 except that 0.98 g (5.0 mmol) of 2,3,4-trimethoxybenzaldehyde (purchased from Tokyo Kasei) was used instead of 2,4,5-trimethoxybenzaldehyde and that 1.21 g (5.0 mmol) of 5-methylfuran-2-ylacetonitrile was used instead of 4-bromophenylacetonitrile.

The compound as a yellow crystalline, 241 mg (yield: 46.7%), represented by the following formula was obtained in the same method as in Example 1 except that 597 mg (2.0 mmol) of the above 5-methyl-α-(2,3,4-trimethoxybenzylidene)furan-2-acetonitrile was used instead of α-cyano-4-bromo-2',4',5'-trimethoxystilbene:

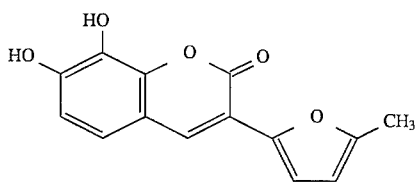

Formula 68 melting point of the obtained compound was 246.5°–247.0° C.

EXAMPLE 36

5-methyl-α-(2,4,5-trimethoxybenzylidene)furan-2-acetonitrile, 687 mg (yield: 46.1%) as a yellow crystalline, was obtained in the same method as in Referential Example 1 except that 0.98 g (5.0 mmol) of 2,4,5-trimethoxybenzaldehyde was used and that 1.21 g (5.0 mmol) of 5-methylfuran-2-ylacetonitrile was used instead of 4-bromophenylacetonitrile.

The compound as a yellowish brown crystalline, 140 mg (yield: 27.0%), represented by the following formula was obtained in the same method as in Example 1 except that 597 mg (2.0 mmol) of the above 5-methyl-α-(2,4,5-trimethoxybenzylidene)furan-2-acetonitrile was used instead of α-cyano-4-bromo-2',4',5'-trimethoxystilbene:

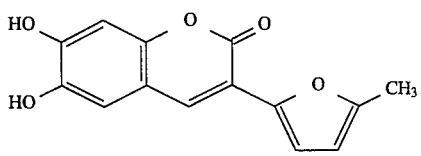

Formula 69 melting point of the obtained compound was 278° C. (decomposed).

Referential Example 7

Synthesis of α-cyano-3-chloro-2,4,5-trimethoxystilbene 3-chlorophenylacetonitrile (purchased from Tokyo Kasei), 1.96 g (10.0 mmol), and 1.96 g (10.0 mmol) of 2,4,5-trimethoxybenzaldehyde (purchased from Lancaster) were dissolved in 10 ml of ethanol (purchased from Kokusan Kagaku) under heating, 2 drops of 20% aqueous sodium hydroxide solution was added to the solution and stirred over night, and the precipitate was crushed, and washed with ethanol twice and hexane twice, and dried to give 3.05 g (yield: 92.5%) of α-cyano-3-chloro-2',4',5'-trimethoxystilbene (as a yellow crystalline).

Referential Example 8

Synthesis of 3-(3-chlorophenyl)-6,7-dihydroxycoumarin

A mixture of 660 mg (2.00 mmol) of α-cyano-3-chloro-2',4',5'-trimethoxystilbene obtained in the same method as in Referential Example 7 and 3.5 g (30 mmol) of pyridinium chloride (purchased from Wako Junyaku Kogyo) was melted to mix on an oil bath heated at 210° C., stirred at the same temperature for 1 hour. After being cooled, 20 ml of 2N hydrochloric acid was added to the resultant reaction mass, the resultant reaction mass was crushed and stirred for 30 minutes, and the precipitate was washed with water three times, dried and purified by short column chromatography on silica gel (using ethyl acetate as an effluent) to give 486 mg (yield: 84.2%) of 3-(3-chlorophenyl)-6,7-dihydroxycoumarin (as a yellow crystalline) represented by the following formula 34b:

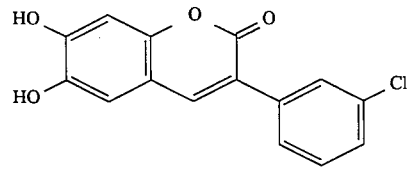

Formula 34b

Referential Example 9

Synthesis of 4-iodophenylacetonitrile

A mixture of 4.36 g (20.0 mmol) of p-iodotoluene (purchased from Tokyo Kasei), 3.9 g (22 mmol) of N-bromosuccinimide (purchased from Tokyo Kasei) and 60 ml of carbon tetrachloride (purchased from Wako Junyaku Kogyo) was refluxed under the irradiation by means of an incandescent lamp for 4 hours to give 2.67 g (yield: 45.0%) of 4-iodobenzyl bromide (as a white crystalline). Subsequently, to 0.49 g (10 mmol) of sodium cyanide (purchased from Kokusan Kagaku) in 10 ml of dimethyl sulfoxide (purchased from Aldrich) solution heated at 50° C. was added 1.48 g (5.00 mmol) of the above 4-iodobenzyl bromide, the mixture was stirred at ambient temperature for 3 hours, the resultant reaction mass was dissolved in water and extracted with hexane, and hexane was removed to give 0.84 g (yield: 68.9%) of 4-iodophenylacetonitrile as a white crystalline.

Referential Example 10

Synthesis of 4-ethylphenylacetonitrile

A mixture of 2.72 g (20.0 mmol) of 4-ethylbenzyl alcohol (purchased from Aldrich) and 50 ml of 47% hydrobromic acid (purchased from Wako Junyaku Kogyo) was stirred at room temperature for 30 minutes vigorously and extracted with hexane to give 3.98 g of 4-ethylbenzyl bromide as a colorless oil. Subsequently, to 20 ml of 1.96 g (40.0 mmol) of sodium cyanide (purchased from Kokusan Kagaku) in dimethyl sulfoxide (purchased from Aldrich) solution heated at 50° C. was added 3.98 g of the above 4-ethylbenzyl bromide, the mixture was stirred at ambient temperature for 3 hours, the resultant reaction mass was dissolved in water and extracted with hexane, and hexane was removed to give 2.70 g (yield: 93.1%) of 4-ethylphenylacetonitrile as a light yellow oil.

Referential Example 11

Synthesis of 4-bromothiophene-2-acetic acid

To 12 ml of suspension of 1.20 g (30 mmol) of sodium hydride (60% oily, purchased from Wako Junyaku Kogyo) in anhydrous dioxane (purchased from Aldrich) was added 9 ml of solution of 9.94 g (30 mmol) of tetraethyl dimethylaminomethylene diphosphate (purchased from Lancaster) in anhydrous dioxane, and the mixture was stirred at room temperature for 10 minutes. Subsequently, 9 ml of solution of 5.73 g (30.0 mmol) of 4-bromo-2-thiophenecarboxaldehyde (purchased from Aldrich) in anhydrous dioxane was added thereto, and the mixture was stirred at 60° C. for 1 hour. After being cooled, the mixture was added to 100 ml of water, extracted with ether three times and dried over anhydrous sodium sulfate, and the solvent was removed to give 14.85 g of substance as a black oil.

The substance was added to 15 ml of concentrated hydrochloric acid, and the mixture was refluxed for 15 minutes, and the resultant mixture was added to 100 ml of cooled water and extracted with ether three times. The extract solution was subjected to reverse extraction with a 2N sodium hydroxide solution twice, adjusted its pH to 1 with 6N hydrochloric acid and extracted with ether three times, and then washed with brine and dried over anhydrous sodium sulfate, and the solvent was removed to give substance as a brown oil. The oily substance was purified according to column chromatography on silica gel (ethyl acetate:hexane=1:1 as an eluent) to give 1.29 g (yield: 19.5%) of 4-bromothiophene-2-acetic acid as a yellow white crystalline.

Referential Example 12

Synthesis of 5-methylfuran-2-ylacetonitrile

A mixture of 5.51 g (50.0 mmol) of 5-methylfuran-2-carboxaldehyde (purchased from Wako Junyaku Kogyo), 6.66 g (50.0 mmol) of rhodanine (purchased from Tokyo Kasei) 12.3 g (150 mmol) of anhydrous sodium acetate (purchased from Kokusan Kagaku) in 35 ml of acetic acid (purchased from Wako Junyaku Kogyo) was refluxed for 30 minutes, cooled and added to 500 ml of water, and the precipitate was collected, washed with water, ethanol and ether in order and dried to give 10.04 g (yield: 89.1%) of of (5-methylfurfurylidene)rhodanine as an orange brown crystalline.

The total amount of the substance was suspended into 65 ml of 15% aqueous sodium hydroxide solution, the suspension was heated at 100° C. for 30 minutes, cooled and added to 500 ml of 10% hydrochloric acid. The precipitate was collected, washed with water and dried to give 8.22 g of 3-(5-methylfuryl)-2-thioketopropionic acid as a yellow crystalline.

To the total amount of the substance were added 45 ml of ethanol and 10.1 g (146 mmol) of hydrochloric acid hydroxylamine (purchased from Wako Junyaku Kogyo), 55 ml (147 mmol) of sodium ethoxide (purchased from Aldrich, 21% denatured ethanol solution) was further added thereto slowly, and the mixture was heated at 100° C. for 1 hour, cooled and concentrated under reduced pressure. Into the residue was suspended 20 ml of aqueous sodium hydroxide solution, and 20 ml of 10% hydrochloric acid was added thereto under ice-cooling carefully, the resultant product was extracted with ether three times, the ether layer was washed with brine, dried over anhydrous sodium sulfate, and then ether was removed.

The residue was dissolved in a small amount of ether, toluene was added thereto till cloudiness occurred, the resultant product was allowed to stand, and the precipitate was collected, washed with toluene sufficiently and dried to give 4.55 g (yield: 53.3%) of 3-(5-methyl-2-furyl)-2-hydroxyiminopropionic acid as a yellow crystalline.

The total amount of the substance was dissolved in 60 ml of benzene, 3.97 g (24.8 mmol) of 1,1'-carbonyldiimidazoll (purchased from Aldrich) was added thereto slowly, the mixture was heated at 70° C. for 1 hour, cooled, added into 50 ml of ice water and extracted with benzene three times. The benzene layer was washed with aqueous sodium hydrogencarbonate solution, brine, 1% hydrochloric acid and water in order and dried over anhydrous sodium sulfate, and the solvent was removed under reduced pressure to give 2.40 g of substance as an oil. The oily substance was purified by column chromatography on silica gel (ethyl acetate:hexane= 1:4 as an eluent) to give 2.00 g (yield: 66.6%) of substance of 5-methylfuran-2-ylacetonitrile as a colorless oil.

Referential Example 13

Synthesis of 3-(4-chlorophenyl)-4-methyl-6,7-dihydroxycoumarin

To a mixed solution of 25 ml of concentrated hydrochloric acid and 15 g of ice were added 3.83 g (30,0 mmol) of p-chloroaniline (purchased from Tokyo Kasei), 7 ml of a 30% aqueous solution of sodium nitrite (purchased from Wako Junyaku Kogyo) in order, and the mixture was stirred at room temperature for 1 hour. A saturated aqueous solution of sodium acetate (purchased from Wako Junyaku Kogyo) was added to the mixture to adjust its pH to 4, insoluble materials were filtrated, the filtrate was added to a suspension of 5.77 g (30.0 mmol) of 4-methylesculetin (purchased from Tokyo Kasei) in 90 ml of acetone, 0.8 g of cupric chloride dihydrate (purchased from Kanto Kagaku) was further added thereto, and the mixture was stirred for 1 hour. The resultant mixture was concentrated under reduced pressure, most of the solvent was removed, 300 ml of ethyl acetate was added to the residue and mixed, insoluble material (unreacted 4-methylesculetin) was filtrated, an organic layer was separated, the water layer was extracted with ethyl acetate twice, the combined organic layer was washed with brine and dried over anhydrous magnesium sulfate, the solvent was removed under reduced pressure, the residue was purified according to column chromatography on silica gel (ethyl acetate:hexane=1:1 as an eluent), the effluent fraction containing an objective compound was allowed to stand, and the precipitate was collected and dried to give 533 mg (yield: 5.9%) of 3-(4-chlorophenyl)-4-methyl-6,7-dihydroxycoumarin (as a light yellow crystalline) represented by the following formula 35b:

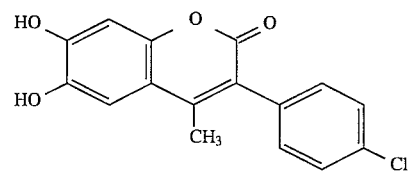

Formula 35b

Referential Example 14

Synthesis of 3-(4-fluorophenyl)-7,8-dihydroxycoumarin

To a mixture of 356 mg (1.00 mmol) of a compound represented by the formula 44b obtained in the same method as in Example 41 and 8 ml of ethanol (purchased from Kokusan Kagaku) was added 2 ml of 6N hydrochloric acid, the mixture was refluxed for 1 hour and cooled, the resultant product was added to 60 ml of water and stirred, and the precipitate was collected, washed with water, dried and recrystallized from ethyl acetate-hexane to give 193 mg (yield: 70.9%) of 3-(4-fluorophenyl)-7,8-dihydroxycoumarin (as a light yellow crystalline) represented by the following formula 36b:

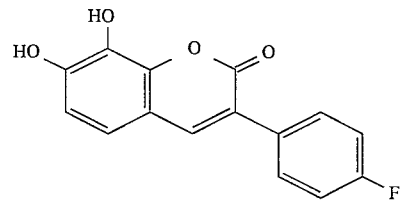

Formula 36b

EXAMPLE 37

To a mixture of 771 mg (5.00 mmol) of 2,3,4-trihydroxybenzaldehyde (purchased from Aldrich), 853 mg (5.00 mmol) of 4-chlorophenylacetic acid (purchased from Tokyo Kasei) and 10 ml of acetic anhydride (purchased from Wako Junyaku Kogyo) was added 5 ml of triethylamine (purchased from Kokusan Kagaku) under ice-cooling, and the mixture was stirred under the protection of a calcium chloride tube for 1 hour and refluxed in an oil bath heated at 120° C. for 4 hours. Subsequently, the resultant mixture was cooled, added to 100 ml of ice-cooled 10% hydrochloric acid and stirred vigorously, the precipitate was collected and washed with water and ethanol, and the precipitate as a light brown crystalline was recrystallized from chloroform and ethanol to give 1.17 g (yield: 62.9%) of the compound as a white crystalline represented by the following formula 37b:

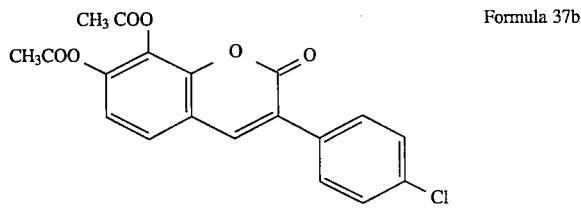

Formula 37b melting point of the obtained compound was 188.0°–188.5° C.

Comparative Example 6

3-(4-chlorophenyl)-7,8-dihydroxycoumarin (as a light yellow crystalline), 227 mg (yield: 78.6%), represented by the following formula 38b was obtained in the same method as in Referential Example 14 except that 373 mg (1.00 mmol) of the compound represented by the formula 37b obtained in Example 37 was used instead of the compound represented by the formula 44b:

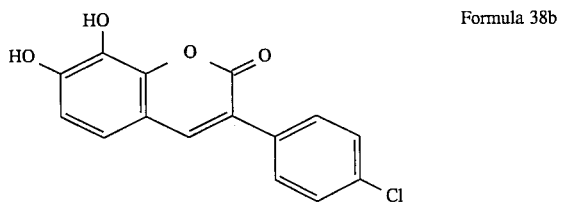

Formula 38b

EXAMPLE 38

To a mixture of 154 mg (1.00 mmol) of 2,4,5-trihydroxybenzaldehyde (purchased from Lancaster), 171 mg (1.00 mmol) of 4-chlorophenylacetic acid (purchased from Tokyo Kasei) and 2 ml of acetic anhydride (purchased from Wako Junyaku Kogyo) was added 1 ml of triethylamine (purchased from Kokusan Kagaku) under ice-cooling, and the mixture was stirred under the protection of a calcium chloride tube for 1 hour and refluxed in an oil bath heated at 120° C. for 4 hours. Subsequently, the resultant mixture was cooled, added to 20 ml of ice-cooled 10% hydrochloric acid and stirred vigorously, the precipitate was collected and washed with water, and dissolved in ethyl acetate and dried, the solvent was removed under reduced pressure, and the residue was recrystallized from ethyl acetate and hexane to give 280 mg (yield: 75.1%) of the compound as a white crystalline represented by the following formula 39b:

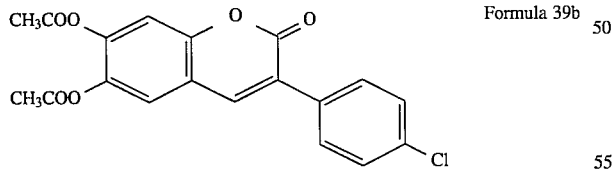

Formula 39b melting point of the obtained compound was 211.5°–212.5° C.

Comparative Example 7

3-(4-chlorophenyl)-6,7-dihydroxycoumarin (as a light yellow crystalline), 233 mg (yield: 80.6%), represented by the following formula 40b was obtained in the same method as in Referential Example 14 except that 373 mg (1.00 mmol) of the compound represented by the formula 39b obtained in Example 38 was used instead of the compound represented by the formula 44b:

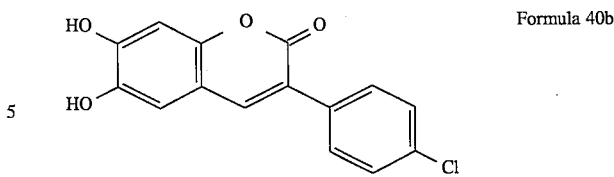

Formula 40b

EXAMPLE 39

The compound as a white crystalline, 853 mg (yield: 45.8%), represented by the following formula 41b was obtained in the same method as in Example 37 except that 853 mg (5.00 mmol) of 3-chlorophenylacetic acid (purchased from Tokyo Kasei) was used instead of 4-chlorophenylacetic acid and that ethyl acetate-hexane was used as a solvent for recrystallization:

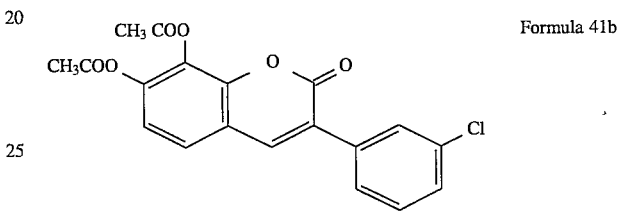

Formula 41b melting point of the obtained compound was 165°–167° C.

Comparative Example 8

3-(3-chlorophenyl)-7,8-dihydroxycoumarin (as a light yellow crystalline), 268 mg (yield: 92.8%), represented by the following formula 42b was obtained in the same method as in Referential Example 14 except that 373 mg (1.00 mmol) of the compound represented by the formula 41b and obtained in Example 39 was used instead of the compound represented by the formula 44b:

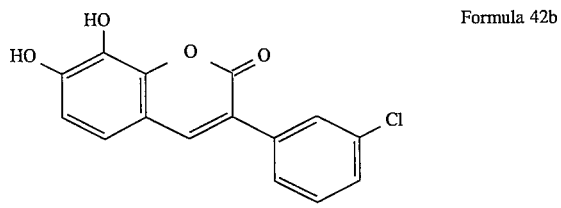

Formula 42b

EXAMPLE 40

To a suspension of 87 mg (0.30 mmol) of 3-(3-chlorophenyl)-6,7-dihydroxycoumarin obtained in the same method as in Referential Example 8 in 2 ml of methylene chloride (purchased from Kokusan Kagaku) was added 0.09 ml of triethylamine (purchased from Kokusan Kagaku) and to the resultant clear orange color solution was added 0.05 ml of acetyl chloride (purchased from Wako Junyaku Kogyo) under ice-cooling. The mixture was stirred under ice-cooling and then at room temperature for 30 minutes. The resultant mixture was diluted with 30 ml of ethanol (purchased from Kokusan Kagaku). The precipitate was collected and washed with ethanol and hexane in order and dried to give 96 mg (yield: 86%) of the compound as a white crystalline represented by the following formula 43b:

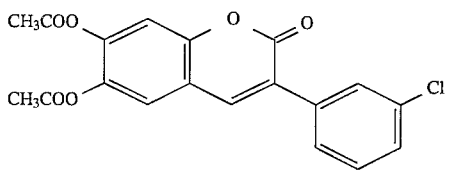

Formula 43b melting point of the obtained compound was 194°–195° C.

EXAMPLE 41

The compound as a white crystalline, 1.26 g (yield: 70.8%), represented by the following formula 44b was obtained in the same method as in Example 37 except that 771 mg (5.00 mmol) of 4-fluorophenylacetic acid (purchased from Lancaster) was used instead of 4-chlorophenylacetic acid:

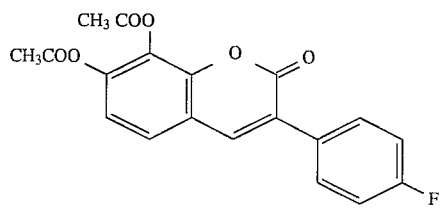

Formula 44b melting point of the obtained compound was 183.5°–184.0° C.

EXAMPLE 42

The compound as a white crystalline, 1.02 g (yield: 48.8%), represented by the following formula 45b was obtained in the same method as in Example 37 except that 1075 mg (5.00 mmol) of 4-bromophenylacetic acid (purchased from Tokyo Kasei) was used instead of 4-chlorophenylacetic acid:

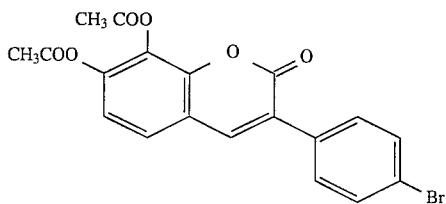

Formula 45b melting point of the obtained compound was 201.5°–202.5° C.

Comparative Example 9

The 3-(4-bromophenyl)-7,8-dihydroxycoumarin (as a yellow crystalline), 300 mg (yield: 90.2%), represented by the following formula 46b was obtained in the same method as in Referential Example 14 except that 417 mg (1.00 mmol) of the compound represented by the formula 45b obtained in Example 42 was used instead of the compound represented by the formula 44b:

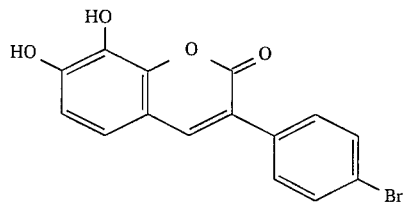

Formula 46b

EXAMPLE 43

α-cyano-4-iodo-2',4',5'-trimethoxystilbene was obtained in the same method as in Referential Example 7 except that 392 mg (2.00 mmol) of 2,4,5-trimethoxybenzaldehyde (purchased from Lancaster) was used and that 486 mg (2.00 mmol) of 4-iodophenylacetonitrile obtained in the same method as in Referential Example 9 was used instead of 3-chlorophenylacetonitrile.

3-(4-iodophenyl)-6,7-dihydroxycoumarin (yellow crystals), 566 mg (yield: 74.4%), represented by the following formula 47b was obtained in the same method as in Referential Example 8 except that 421 mg (1.00 mmol) of the above α-cyano-4-iodo-2',4',5'-trimethoxystilbene was used instead of α-cyano-3-chloro-2',4',5'-trimethoxystilbene:

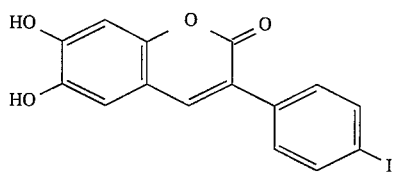

Formula 47b

The compound as a white crystalline, 100 mg (yield: 2.1%), represented by the following formula 48b was obtained in the same method as in Example 40 except that 114 mg (0.30 mmol) of the above 3-(4-iodophenyl)-6,7-dihydroxycoumarin was used instead of 3-(3-chlorophenyl)-6,7-hydroxycoumarin:

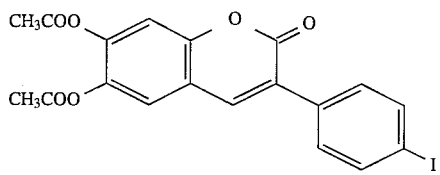

Formula 48b melting point of the obtained compound was 189.0°–190.0° C.

EXAMPLE 44

The compound as a white crystalline, 626 mg (yield: 35.3%), represented by the following formula 49b was obtained in the same method as in Example 37 except that 751 mg (5.00 mmol) of 4-methylphenylacetic acid (purchased from Tokyo Kasei) was used instead of 4-chlorophenylacetic acid:

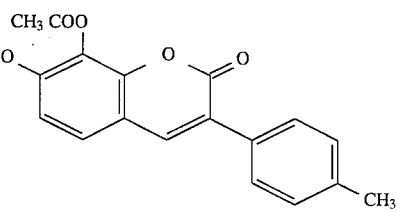

Formula 49b melting point of the obtained compound was 199°–200° C.

Comparative Example 10

3-(4-methylphenyl)-7,8-dihydroxycoumarin (as a yellow crystalline), 233 mg (yield: 86.9%), represented by the following formula 50b was obtained in the same method as in Referential Example 8 except that 352 mg (1.00 mmol) of the compound represented by the formula 49b obtained in Example 8 was used instead of the compound represented by the formula 44b:

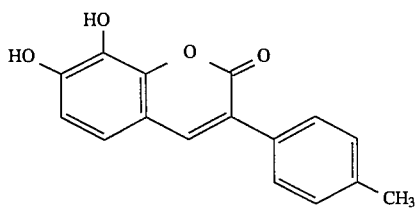

Formula 50b

EXAMPLE 45

The compound as a white crystalline, 684 mg (yield: 38.88%), represented by the following formula 51b was obtained in the same method as in Example 37 except that mg (5.00 mmol) of 3-methylphenylacetic acid (purchased from Tokyo Kasei) was used instead of 4-chlorophenylacetic acid and that ethyl acetate-hexane was used as a for solvent recrystallization:

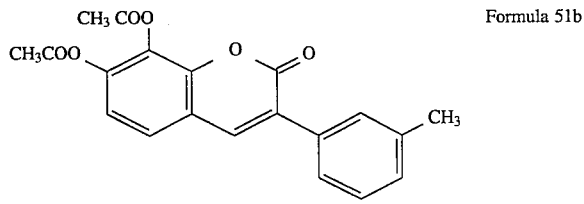

Formula 51b melting point of the obtained compound was 155°–156° C.

Comparative Example 11

3-(3-methylphenyl)-7,8-dihydroxycoumarin (as a yellow crystalline), 212 mg (yield: 79.2%), represented by the following formula 52b was obtained in the same method as in Referential Example 14 except that 352 mg (1.00 mmol) of the compound represented by the formula 51b obtained in Example 45 was used instead of the compound represented by the formula 44b:

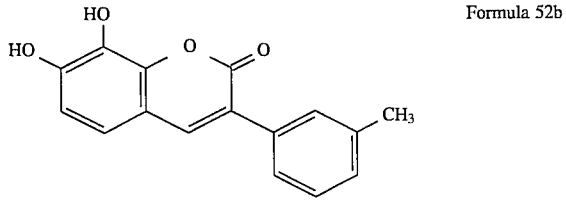

Formula 52b

EXAMPLE 46

α-cyano-4-ethyl-2',4',5'-trimethoxystilbene was obtained in the same method as in Referential Example 7 except that 628 mg (3.20 mmol) of 2,4,5-trimethoxybenzaldehyde (purchased from Lancaster) was used and that 465 mg (3.20 mmol) of 4-ethylphenylacetonitrile obtained in the same method as in Referential Example 10 was used instead of 3-chlorophenylacetonitrile.

3-(4-ethylphenyl)-6,7-dihydroxycoumarin (as a yellow crystalline), 493 mg (yield: 87.5%), represented by the following formula 53b was obtained in the same method as in Referential Example 8 except that 485 mg (1.50 mmol) of the above α-cyano-4-ethyl-2',4',5'-trimethoxystilbene was used instead of α-cyano-3-chloro-2',4',5'-trimethoxystilbene:

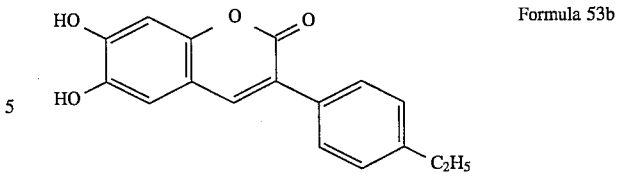

Formula 53b

The compound as a white crystalline, 46 mg (yield: represented by the following formula 54b was obtained in the same method as in Example 14 except that 85 mg (0.30 mmol) of the above 3-(4-ethylphenyl)-6,7-dihydroxycoumarin was used instead of 3-(3-chlorophenyl)-6,7-hydroxycoumarin:

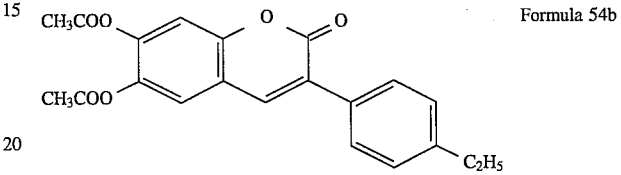

Formula 54b melting point of the obtained compound was 161.5°–162.0° C.

EXAMPLE 47

α-cyano-4-trifluoromethyl-2',4',5'-trimethoxystilbene was obtained in the same method as in Referential Example 7 except that 1.85 g (10.0 mmol) of 4-trifluoromethylphenylacetonitrile (purchased from Aldrich) was used instead of 3-chlorophenylacetonitrile.

3-(4-trifluoromethylphenyl)-6,7-dihydroxycoumarin (as a light yellow crystalline), 594 mg (yield: 92.2%) represented by the following formula 55b was obtained in the same method as in Referential Example 2 except that 727 mg (2.00 mmol) of the above α-cyano-4-trifluoromethyl-2',4', 5'-trimethoxystilbene was used instead of α-cyano-3-chloro-2',4',5'-trimethoxystilbene:

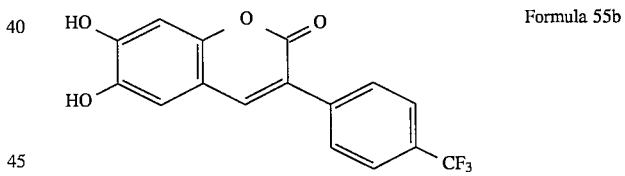

Formula 55b

The compound as a white crystalline, 95 mg (yield: 77.8%), represented by the following formula 56b was obtained in the same method as in Example 40 except that 97 mg (0.30 mmol) of the above 3-(4-trifluoromethylphenyl)-6,7-dihydroxycoumarin was used instead of 3-(3-chlorophenyl)-6,7-hydroxycoumarin:

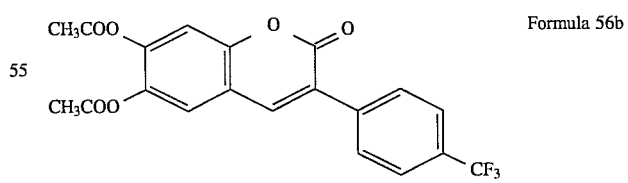

Formula 56b melting point of the obtained compound was 196.5°–197.5° C.

EXAMPLE 48

The compound as a white crystalline, 814 mg (yield: 44.2%), represented by the following formula 57b was obtained in the same method as in Example 37 except that 831 mg (5.00 mmol) of 4-methoxyphenylacetic acid (purchased from Tokyo Kasei) was used instead of 4-chlorophenylacetic acid:

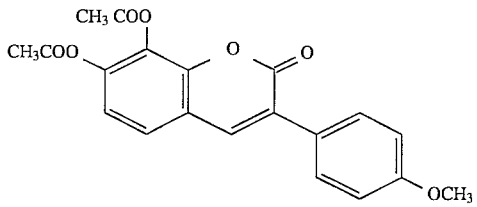

Formula 57b melting point of the obtained compound was 174.5°–175.5° C.

Comparative Example 12

3-(4-methoxyphenyl)-7,8-dihydroxycoumarin (as an ocherous crystalline), 186 mg (yield: 65.6%), represented by the following formula 58b was obtained in the same method as in Referential Example 14 except that 368 mg (1.00 mmol) of the compound represented by the formula 57b obtained in Example 48 was used instead of the compound represented by the formula 44b:

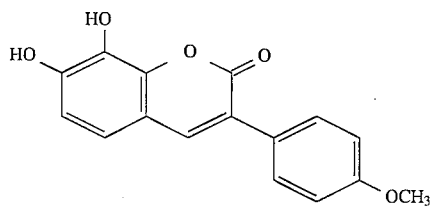

Formula 58b

EXAMPLE 49

The compound as a yellow crystalline, 827 mg (yield: 43.2%), represented by the following formula 59b was obtained in the same method as in Example 37 except that 906 mg (5.00 mmol) of 4-nitrophenylacetic acid (purchased from Tokyo Kasei) was used instead of 4-chlorophenylacetic acid:

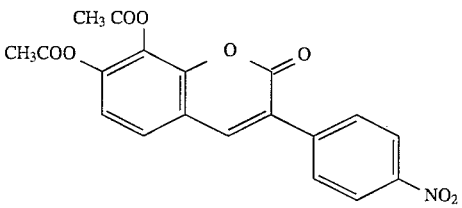

Formula 59b melting point of the obtained compound was 227.5°–228.5° C.

Comparative Example 13

3-(4-nitrophenyl)-7,8-dihydroxycoumarin (as an orange crystalline), 228 mg (yield: 76.2%), represented by the following formula 60b was obtained in the same method as in Referential Example 14 except that 383 mg (1.00 mmol) of the compound represented by the formula 59b obtained in Example 48 was used instead of the compound represented by the formula 44b:

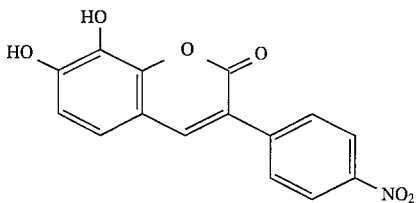

Formula 60b

EXAMPLE 50

α-cyano-2',4',5'-trimethoxystilbene was obtained in the same method as in Referential Example 7 except that 981 mg (5.00 mmol) of 2,4,5-trimethoxybenzaldehyde (purchased from Lancaster) was used and that 586 mg (5.00 mmol) of phenylacetonitrile (purchased from Tokyo Kasei) was used instead of 3-chlorophenylacetonitrile.

3-phenyl-6,7-dihydroxycoumarin (as a yellow brown crystalline), 444 mg (yield: 87.3%), represented by the following formula 61b was obtained in the same method as in Referential Example 8 except that 591 mg (2.00 mmol) of the above α-cyano-2',4',5'-trimethoxystilbene was used instead of α-cyano-2',4',5'-trimethoxystilbene:

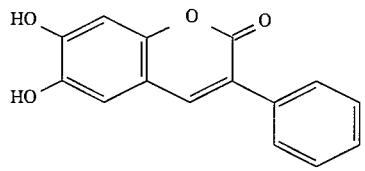

Formula 61b

The compound as a white crystalline, 48 mg (yield: 70%), represented by the following formula 62b was obtained in the same method as in Example 40 except that 76 mg (0.30 mmol) of the above 3-phenyl-6,7-dihydroxycoumarin was used instead of 3-(3-chlorophenyl)-6,7-hydroxycoumarin:

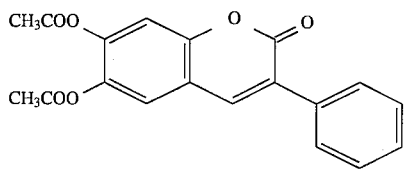

Formula 62b melting point of the obtained compound was 195.0°–195.5° C.

EXAMPLE 51

α-(2,4,5-trimethoxybenzylidene)thiophene-2-acetonitrile was obtained in the same method as in Referential Example 7 except that 1.23 g (10.0 mmol) of thiophen-2-ylacetonitrile (purchased from Tokyo Kasei) was used instead of 3-chlorophenylacetonitrile.

3-(thiophen-2-yl)-6,7-dihydroxycoumarin (as a yellow crystals), 274 mg (yield: 52.6%), represented by the following formula 63b was obtained in the same method as in Referential Example 8 except that 603 mg (2.00 mmol) of the above α-(2,4,5-trimethoxybenzylidene)thiophene-2-acetonitrile was used instead of α-cyano-3-chloro-2',4',5'-trimethoxystilbene:

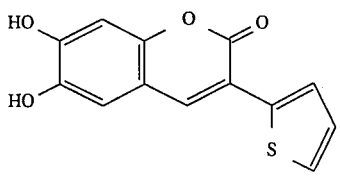

Formula 63b

The compound as a light brown crystalline, 63 mg (yield: 61%), represented by the following formula 64b was obtained in the same method as in Example 40 except that 78 mg (0.30 mmol) of the above 3-(thiophen-2-yl)-6,7-dihydroxycoumarin was used instead of 3-(3-chlorophenyl)-6,7-hydroxycoumarin:

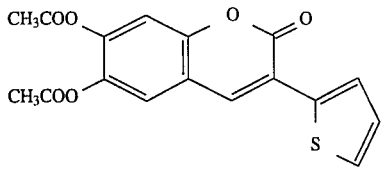

Formula 64b melting point of the obtained compound was 222°–224° C.

EXAMPLE 52

The compound as a light yellow crystalline, 960 mg (yield: 55.8%), represented by the following formula 65b was obtained in the same method as in Example 37 except that 711 mg (5.00 mmol) of thiophene-3-acetic acid (purchased from Tokyo Kasei) was used instead of 4-chlorophenylacetic acid:

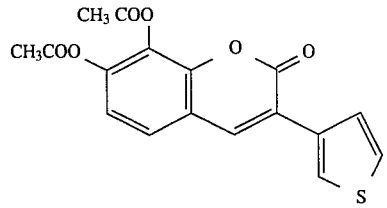

Formula 65b melting point of the obtained compound was 159.5°–160.5° C.

Comparative Example 14

3-(thiophen-3-yl)-7,8-dihydroxycoumarin (as a yellow crystalline), 165 mg (yield: 63.4%), represented by the following formula 66b was obtained in the same method as in Referential Example 14 except that 344 mg (1.00 mmol) of the compound represented by the formula 65b obtained in Example 52 was used instead of the compound represented by the formula 44b:

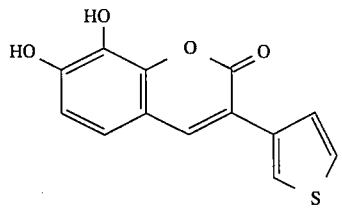

Formula 66b

EXAMPLE 53

The compound as a light brown crystalline, 756 mg (yield: 71.4%), represented by the following formula 67b was obtained in the same method as in Example 37 except that 385 mg (2.50 mmol) of 2,3,4-trihydroxybenzaldehyde (purchased from Aldrich) was used and that 553 mg (2.50 mmol) of 4-bromothiophene-2-acetic acid obtained in the same method as in Referential Example 11 was used instead of 4-chlorophenylacetic acid:

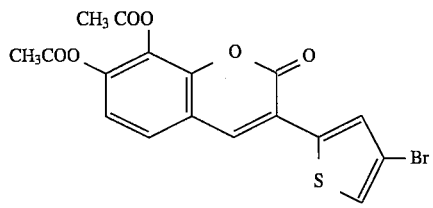

Formula 67b melting point of the obtained compound was 234.0°–235.0° C.

Comparative Example 15

3-(4-bromothiophen-2-yl)-7,8-dihydroxycoumarin (as a yellow crystalline), 310 mg (yield: 91.4%), represented by the following formula 68b was obtained in the same method as in Referential Example 14 except that 423 mg (1.00 mmol) of the compound represented by the formula 67b obtained in Example 53 was used instead of the compound represented by the formula 44b:

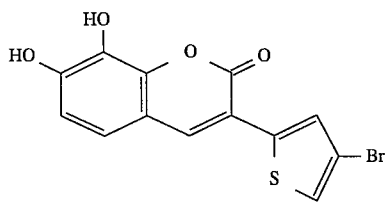

Formula 68b

EXAMPLE 54

The compound as a light brown crystalline, 755 mg (yield: 71.4%), represented by the following formula 69b was obtained in the same method as in Example 37 except that 385 mg (2.50 mmol) of 2,4,5-trihydroxybenzaldehyde (purchased from Lancaster) was used instead of 2,3,4-trihydroxybenzaldehyde and that 553 mg (2.50 mmol) of 4-bromothiophene-2-acetic acid obtained in the same method as in Referential Example 11 was used instead of 4-chlorophenylacetic acid:

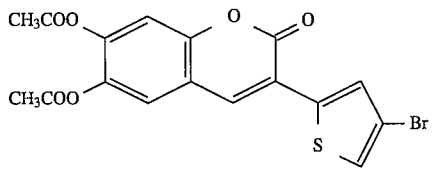

Formula 69b melting point of the obtained compound was 220.5°–221.5° C.

Comparative Example 16

3-(4-bromothiophen-2-yl)-6,7-dihydroxycoumarin (as a yellow crystalline), 287 mg (yield: 84.6%), represented by the following formula 70b was obtained in the same method as in Referential Example 14 except that 423 mg (1.00 mmol) of the compound represented by the formula 69b obtained in Example 54 was used instead of the compound represented by the formula 44b:

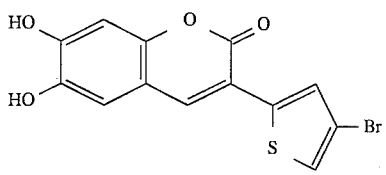

Formula 70b

EXAMPLE 55

5-methyl-α-(2,4,5-trimethoxybenzylidene)furan-2-acetonitrile was obtained in the same method as in Referential Example 7 except that 981 mg (5.00 mmol) of 2,4,5-trimethoxybenzaldehyde (purchased from Lancaster) was used and that 1.21 g (5.00 mmol) of 5-methylfuran-2-ylacetonitrile obtained in the same method as in Referential Example 12 was used instead of 3-chlorophenylacetonitrile.

3-(5-methylfuran-2-yl)-6,7-dihydroxycoumarin (as a yellow brown crystalline), 241 mg (yield: 46.7%), represented by the following formula 71b was obtained in the same method as in Referential Example 8 except that 597 mg (2.00 mmol) of the above 5-methyl-α-(2,4,5-trimethoxybenzylidene)furan-2-acetonitrile was used instead of α-cyano-3-chloro-2',4',5'-trimethoxystilbene:

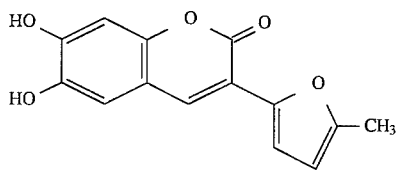

Formula 71b

The compound as a light yellow crystalline, 47 mg (yield: 46%), represented by the following formula 72b was obtained in the same method as in Example 40 except that 77 mg (0.30 mmol) of the above 3-(5-methylfuran-2-yl)-6,7-dihydroxycoumarin was used instead of 3-(3-chlorophenyl)-6,7-hydroxycoumarin:

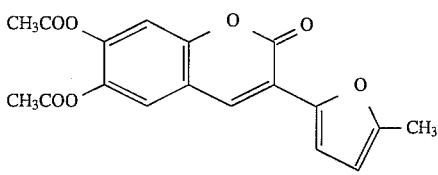

Formula 72b melting point of the obtained compound was 199.5°–200.0° C.

EXAMPLE 56

3-(4-chlorophenyl)-4-methyl-6,7-dihydroxycoumarin, 100 mg (0.33 mmol), obtained in the same method as in Referential Example 13 was suspended into 2 ml of methylene chloride (purchased from Kokusan Kagaku), 0.11 ml of triethylamine (purchased from Kokusan Kagaku) was added thereto and stirred, the obtained clear orange colored solution was ice-cooled, 0.06 ml of acetyl chloride (purchased from Wako Junyaku) were added thereto, and the mixture was stirred under ice-cooling and further stirred at room temperature for 30 minutes.

Ethyl acetate was added to the resultant mixed solution, an organic layer was separated, washed with 1N hydrochloric acid, with aqueous sodium hydrogencarbonate solution and with brine in order and dried over anhydrous sodium sulfate, the solvent was removed under reduced pressure, and the residue was recrystallized from ethyl acetate-hexane to give 104 mg (yield: 81.3%) of the compound as a light yellow crystalline represented by the following formula 73b:

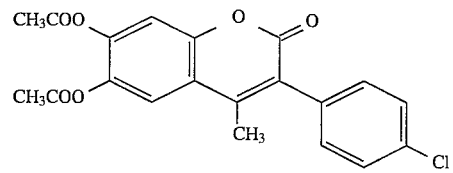

Formula 73b melting point of the obtained compound was 151.5°–152.5° C.

EXAMPLE 57

3-(3-chlorophenyl)-6,7-dihydroxycoumarin, 577 mg (2.00 mmol), obtained in the same method as in Referential Example 8 was suspended into 10 ml of methylene chloride (purchased from Kokusan Kagaku), and 0.69 ml of triethylamine (purchased from Kokusan Kagaku) was added thereto and stirred, the obtained clear orange colored solution was ice-cooled, 0.44 ml of propionyl chloride (purchased from Tokyo Kasei) was added thereto, and the mixture was stirred under ice-cooling and further stirred at room temperature for 30 minutes. Ethyl acetate was added to the resultant mixed solution, an organic layer was separated, washed with 1N hydrochloric acid, with aqueous sodium hydrogencarbonate solution and with brine in order and dried over anhydrous sodium sulfate, the solvent was removed under reduced pressure, and the residue was recrystallized from ethyl acetate-hexane to give 671 mg (yield: 83.7%) of the compound as a light yellow crystalline represented by the following formula 74b:

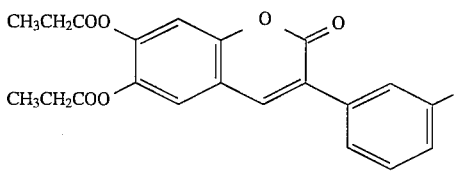

Formula 74b melting point of the obtained compound was 163°–165° C.

EXAMPLE 58

The compound as a white crystalline, 673 mg (yield: 8.4%), represented by the following formula 75b was obtained in the same method as in Example 57 except that 0.52 ml of butyryl chloride (purchased from Tokyo Kasei) was used instead of propionyl chloride:

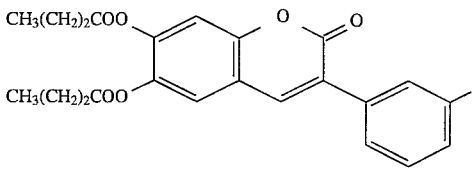

Formula 75b melting point of the obtained compound was 135°–136° C.

EXAMPLE 59

A mixture having the following composition per a tablet was prepared and tableted by a tableting machine according to an ordinary procedure to give a medicine of the present invention inhibiting 12-lipoxygenase selectively.

| | |
|---|---|
| Compound obtained in Example 37 | 20.0 (mg) |
| Lactose (purchased from Iwaki Seiyaku) | 40.0 |
| Cornstarch (purchased from Yoshida | 15.0 |

| | |
|---|---|
| Seiyaku) | |
| Magnesium stearate (purchased from Taihei Kagaku) | 0.4 |
| Carboxymethylcellulose calcium (purchased from Nichirin Kagaku Kogyo) | 20.0 |

EXAMPLE 60

A mixture having the following composition per a capsule was prepared and filled into a gelatin capsule according to an ordinary procedure to give a medicine of the present invention inhibiting 12-lipoxygenase selectively.

| | |
|---|---|
| Compound obtained in Example 37 | 20.0 (mg) |
| Lactose (purchased from Iwaki Seiyaku) | 40.0 |
| Fine powdered cellulose (purchased from Nippon Soda) | 30.0 |
| Magnesium stearate (purchased from Taihei Kagaku) | 3.0 |

EXAMPLE 61

To a suspension of 931 mg (5.00 mmol) of naphthalene-2-acetic acid (purchased from Tokyo Kasei) and 771 mg (5.00 mmol) of 2,3,4-trihydroxybenzaldehyde (purchased from Aldrich) in 10 ml of acetic anhydride (purchased from Wako Junyaku Kogyo) was added 5 ml of triethylamine (purchased from Kokusan Kagaku) under ice-cooling and the reaction mixture was stirred under ice-cooling for 1 hour. Subsequently, the reaction mixture was refluxed on an oil bath heated at 120° C., cooled, added to 100 ml of 1N hydrochloric acid and stirred. The precipitate was collected, washed with water and with ethanol (purchased from Kokusan Kagaku) three times and with hexane (purchased from Kokusan Kagaku) twice and dried to give 1.52 g (yield: 78.4%) of the compound as a cream-colored crystalline of 7,8-diacetoxy-3-(naphthalen-2-yl)coumarin.

A mixture of 388 mg (1.00 mmol) of the above 7,8-diacetoxy-3-(naphthalen-2-yl)coumarin, 8 ml of ethanol (purchased from Kokusan Kagaku), 1 ml of concentrated hydrochloric acid and 1 ml of water was refluxed for 4 hours, cooled and added to 100 ml of water, and the precipitate was collected, washed with water and dried.

The obtained resultant product was purified according to column chromatography on silica gel (ethyl acetate (purchased from Kokusan Kagaku):hexane (purchased from Kokusan Kagaku)=1:5~3:1 as an eluent) to give 1045 mg (yield: 86.2%) of the compound as a yellow crystalline represented by the following formula 22c:

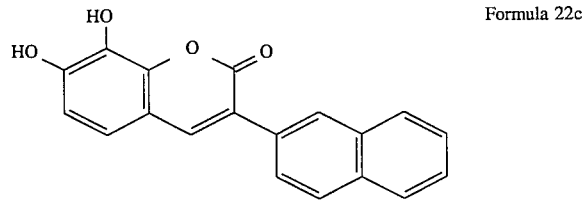

Formula 22c melting point of the obtained compound was 255°–256° C.

EXAMPLE 62

A mixture of 15 ml of 836 mg (5.00 mmol) of naphthalene-2-acetonitrile (purchased from Aldrich) and 981 mg (5.00 mmol) of 2,4,5-trimethoxybenzaldehyde (purchased from Lancaster) in ethanol (purchased from Kokusan Kagaku) was heated to dissolve, 2 drops of 20% aqueous sodium hydroxide solution was added thereto, the mixture was stirred under cooling over night, and the precipitate was collected, washed with ethanol (purchased from Kokusan Kagaku) and hexane (purchased from Kokusan Kagaku) in order and dried to give 1.48 g (yield: 85.9%) of the compound as a yellow crystalline of α-(naphthalen-2-yl)-β-(2,4,5-trimethoxyphenyl)acrylonitrile.

A mixture of 691 mg (2.00 mmol) of the above α-(naphthalen-2-yl)-β-(2,4,5-trimethoxyphenyl)acrylonitrile and 3.5 g (30 mmol) of pyridinium chloride (purchased from Wako Junyaku Kogyo) was melted to mix on an oil bath heated at 220° C., stirred for 1 hour and cooled, 20 ml of 10% hydrochloric acid was added to the resultant reaction mass, the obtained reaction mass was crushed and stirred for 30 minutes, and the precipitate was collected, washed with water and dried. The obtained reaction product was purified according to column chromatography on silica gel [using ethyl acetate (purchased from Kokusan Kagaku) as an effluent] to give 431 mg (yield: 70.8%) of the compound as a yellow crystalline represented by the following formula 23c:

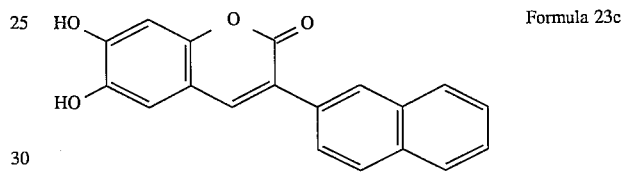

Formula 23c melting point of the obtained compound was 288°–289° C.

EXAMPLE 63

A mixture of 693 mg (4.00 mmol) of thianaphthene-3-acetonitrile (purchased from Lancaster) and 785 mg (4.00 mmol) of 2,3,4-trimethoxybenzaldehyde (purchased from Tokyo Kasei) in 5 ml of ethanol (purchased from Kokusan Kagaku) was heated to dissolve, 2 drops of a 20% aqueous sodium hydroxide solution was added thereto and stirred at ambient temperature over night, the reaction mixture was added to 100 ml of 1N hydrochloric acid, extracted with ethyl acetate twice, washed with aqueous sodium hydrogencarbonate solution and with brine in order and dried over anhydrous sodium sulfate, and the solvent was removed under reduced pressure to give 1.41 g (yield: quantitative) of the compound as a brown oil of α-(thianaphthen-3-yl)-β-(2,3,4-trimethoxyphenyl)acrylonitrile.

The compound as an ocherous crystalline, 343 mg (yield: 55.3%), represented by the following formula 24c was obtained in the same method as in Example 62 except that 703 mg (2.00 mmol) of the above α-(thianaphthen-3-yl)-β-(2,3,4-trimethoxyphenyl)acrylonitrile was used instead of α-(naphthalen-2-yl)-β-(2,4,5-trimethoxyphenyl)acrylonitrile:

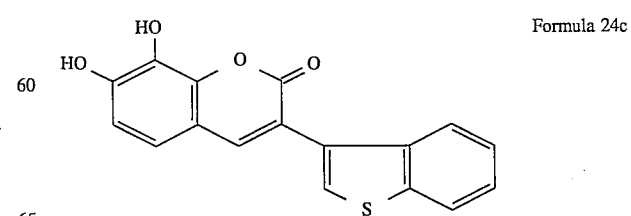

Formula 24c

The obtained compound did not show a clear melting point, and blackened and decomposed at about 140° C. (The measured values of the nuclear magnetic resonance spectrum and the infrared absorption spectrum of the present compound were shown in Table 23.)

EXAMPLE 64

The compound as a yellow crystalline, 579 mg (yield: 41.2%), of α-(thianaphthen-3-yl)-β-(2,4,5-trimethoxyphenyl)acrylonitrile was obtained in the same method as in Example 63 except that 785 mg (4.00 mmol) of 2,4,5-trimethoxybenzaldehyde (purchased from Lancaster) was used instead of 2,3,4-trimethoxybenzaldehyde. However, since the objective compound was separated out as precipitate from the reaction mixture, differing from the case of Example 63, the following procedure was performed according to the same method as in Example 62.

The compound as a green yellow crystalline, 127 mg (yield: 34.1%), represented by the following formula 25c was obtained in the same method as in Example 62 except that 422 mg (1.20 mmol) of the above α-(thianaphthen-3-yl)-β-(2,3,4-trimethoxyphenyl)acrylonitrile was used instead of α-(naphthalen-2-yl)-β-(2,4,5-trimethoxyphenyl)acrylonitrile and that 2.1 g (18 mmol) of pyridinium chloride (purchased from Wako Junyaku Kogyo) was used:

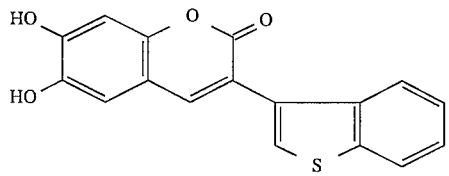

Formula 25c the obtained compound did not show a clear melting point, and colored and decomposed at about 220° C. (The measured values of the nuclear magnetic resonance spectrum and the infrared absorption spectrum of the present compound were shown in Table 23.)

EXAMPLE 65

A mixture having the following composition per a tablet was prepared and tableted by a tableting machine according to an ordinary procedure to give a medicine of the present invention inhibiting 12-lipoxygenase selectively.

| | |
|---|---|
| Compound obtained in Example 62 | 20.0 (mg) |
| Lactose (purchased from Iwaki Seiyaku) | 40.0 |
| Cornstarch (purchased from Yoshida Seiyaku) | 15.0 |
| Magnesium stearate (purchased from Taihei Kagaku) | 0.4 |
| Carboxymethylcellulose calcium (purchased from Nichirin Kagaku Kogyo) | 20.0 |

EXAMPLE 66

A mixture having the following composition per a capsule was prepared and filled into a gelatin capsule according to an ordinary procedure to give a medicine of the present invention inhibiting 12-lipoxygenase selectively.

| | |
|---|---|
| Compound obtained in Example 62 | 20.0 (mg) |
| Lactose (purchased from Iwaki Seiyaku) | 40.0 |
| Fine powdered cellulose (purchased from Nippon Soda) | 30.0 |
| Magnesium stearate (purchased from Taihei Kagaku) | 3.0 |

Industrial Applicability

As described in detail above, the present invention relates to coumarin derivatives inhibiting 12-lipoxygenase selectively and medicines containing these compounds as effective ingredients; furthermore, the present invention relates to novel coumarin derivatives capable of forming substances inhibiting 12-lipoxygenase selectively according to the cleavage of modified moieties due to the function of enzymes in vivo and medicines containing these compounds as effective ingredients and having a selective 12-lipoxygenase inhibitory effect, and the industrial utilization of the present invention is as below:

1) The compounds of the present invention have a strong and selective 12-lipoxygenase inhibitory activity.
2) The medicines containing the compounds of the present invention are useful for the preventing and treating various circulatory diseases such as arteriosclerosis and vasospasm and for preventing the metastasis of some kinds of cancers.
3) The compounds of the present invention are low-toxic, show few side effects and are effective as effective ingredients of medicines inhibiting 12-lipoxygenase selectively.
4) The compounds of the present invention have a strong and selective function of inhibiting 12-lipoxygenase according to the cleavage of modified moieties due to the function of enzymes in vivo.
5) It is possible to control the cleavage in vivo of the compounds of the present invention by selecting the kinds of acyl groups of modified moieties of the compounds of the present invention.

What is claimed is:

1. A compound of the formula:

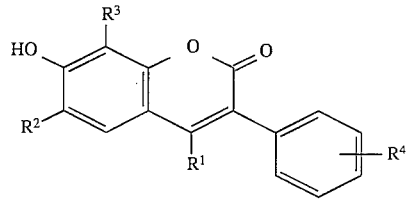

wherein $R^1$ is selected from this group consisting of hydrogen and lower alkyl, $R^2$ and $R^3$ are selected from the group consisting of hydrogen and hydroxy, wherein $R^2$ and $R^3$ are not hydrogen at the same time, and $R^4$ is selected from the group consisting of lower alkyl, lower alkoxy, halogen, trifluoromethyl and cyano.

2. A method for inhibiting 12-lipoxygenase comprising contacting 12-lipoxygenase with a compound of the formula:

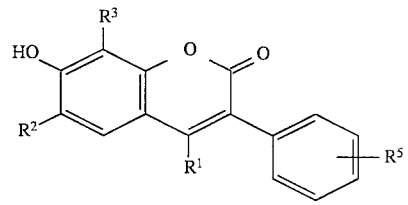

wherein R¹ is selected from the group consisting of hydrogen and lower alkyl, R² and R³ are selected from the group consisting of hydrogen and hydroxy, wherein R² and R³ are not hydrogen at the same time, and R⁵ is selected from the group consisting of hydrogen, lower alkyl, lower alkoxy, halogen, trifluoromethyl, cyano and nitro.

3. A compound of the formula:

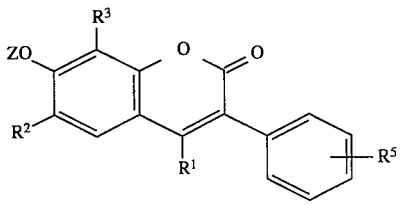

wherein R¹ is selected from the group consisting of hydrogen and lower alkyl, R² and R³ are selected from the group consisting of hydrogen and OZ, wherein R² and R³ are not hydrogen at the same time, and R⁵ is selected from the group consisting of hydrogen, lower alkyl, lower alkoxy, halogen, trifluoromethyl, cyano and nitro, and Z is independently hydrogen or a group represented by the following formula:

wherein none of Z are hydrogen atoms at the same time, and wherein R⁶ is selected from the group consisting of straight-chain alkyl groups having 1 to 20 carbon atoms, branched-chain alkyl groups having 1 to 20 carbon atoms, straight-chain alkenyl groups having 1 to 20 carbon atoms, and branched-chain alkenyl groups having 1 to 20 carbon atoms.

4. A method for inhibiting 12-lipoxygenase comprising contacting 12-lipoxygenase with a compound of the formula:

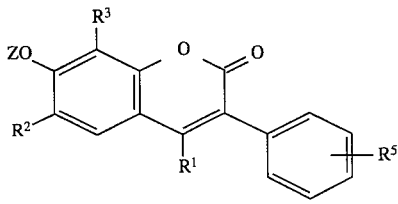

wherein R¹ is selected from the group consisting of hydrogen and lower alkyl, R² and R³ are selected from the group consisting of hydrogen and OZ, wherein R² and R³ are not hydrogen at the same time, and R⁵ is selected from the group consisting of hydrogen, lower alkyl, lower alkoxy, halogen, trifluoromethyl, cyano and nitro, and Z is independently hydrogen or a group represented by the following formula:

wherein none of Z are hydrogen atoms at the same time, and wherein R⁶ is selected from the group consisting of straight-chain alkyl groups having 1 to 20 carbon atoms, branched-chain alkyl groups having 1 to 20 carbon atoms, straight-chain alkenyl groups. having 1 to 20 carbon atoms, and branched-chain alkenyl groups having 1 to 20 carbon atoms.

5. A compound of the formula:

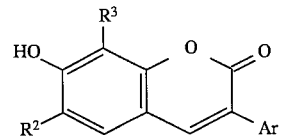

wherein R² and R³ are selected from the group consisting of hydrogen and hydroxy, wherein R² and R³ are not hydrogen at the same time, and Ar is naphthyl.

6. A method for inhibiting 12-lipoxygenase comprising contacting 12-lipoxygenase with a compound of the formula:

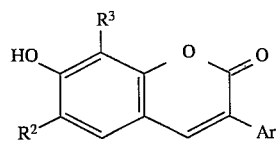

wherein R² and R³ are selected from the group consisting of hydrogen and hydroxy, wherein R² and R³ are not hydrogen at the same time, and Ar is naphthyl.

7. A pharmaceutical composition for inhibiting 12-lipoxygenase, comprising an effective amount of the compound of claim 1 and a pharmaceutically acceptable carrier or diluent.

8. A pharmaceutical composition for inhibiting 12-lipoxygenase, comprising an effective amount of the compound of claim 3 and a pharmaceutically acceptable carrier or diluent.

9. A pharmaceutical composition for inhibiting 12-lipoxygenase, comprising an effective amount of the compound of claim 5 and a pharmaceutically acceptable carrier or diluent.

10. The method of claim 2, wherein said contacting comprises administering an effective amount of said compound to a mammal in need thereof.

11. The method of claim 4, wherein said contacting comprises administering an effective amount of said compound to a mammal in need thereof.

12. The method of claim 6, wherein said contacting comprises administering an effective amount of said compound to a mammal in need thereof.

* * * * *